US011186590B2

(12) United States Patent
Han et al.

(10) Patent No.: US 11,186,590 B2
(45) Date of Patent: Nov. 30, 2021

(54) SOMATOSTATIN MODULATORS AND USES THEREOF

(71) Applicant: CRINETICS PHARMACEUTICALS, INC., San Diego, CA (US)

(72) Inventors: Sangdon Han, San Diego, CA (US);
Sun Hee Kim, San Diego, CA (US);
Yunfei Zhu, San Diego, CA (US)

(73) Assignee: CRINETICS PHARMACEUTICALS, INC., San Diego, CA (US)

(*) Notice: Subject to any disclaimer, the term of this patent is extended or adjusted under 35 U.S.C. 154(b) by 0 days.

(21) Appl. No.: 16/877,947

(22) Filed: May 19, 2020

(65) Prior Publication Data

US 2020/0283453 A1    Sep. 10, 2020

Related U.S. Application Data

(63) Continuation of application No. 16/572,921, filed on Sep. 17, 2019, now Pat. No. 10,696,689.

(60) Provisional application No. 62/732,735, filed on Sep. 18, 2018.

(51) Int. Cl.
| | |
|---|---|
| *C07D 211/06* | (2006.01) |
| *C07D 498/04* | (2006.01) |
| *A61K 9/08* | (2006.01) |
| *A61K 9/20* | (2006.01) |
| *C07D 401/14* | (2006.01) |
| *A61K 9/48* | (2006.01) |
| *A61K 9/06* | (2006.01) |

(52) U.S. Cl.
CPC .............. *C07D 498/04* (2013.01); *A61K 9/06* (2013.01); *A61K 9/08* (2013.01); *A61K 9/2013* (2013.01); *A61K 9/2054* (2013.01); *A61K 9/4825* (2013.01); *C07D 401/14* (2013.01)

(58) Field of Classification Search
CPC ... C07D 211/06; C07D 295/00; C07D 213/02
USPC ........................................................ 546/194
See application file for complete search history.

(56) References Cited

U.S. PATENT DOCUMENTS

| | | | |
|---|---|---|---|
| 6,025,372 A | 2/2000 | Yang et al. | |
| 6,127,343 A | 10/2000 | Ankersen et al. | |
| 7,754,744 B2 | 7/2010 | Binggeli et al. | |
| 8,778,925 B2 | 7/2014 | McDonald et al. | |
| 9,630,976 B2 | 4/2017 | Ishida et al. | |
| 9,643,951 B2 | 5/2017 | Ishida et al. | |
| 10,214,540 B2 | 2/2019 | Ishida et al. | |
| 10,696,689 B2 | 6/2020 | Han et al. | |
| 2006/0281764 A1 | 12/2006 | Gaul et al. | |
| 2011/0059971 A1 | 3/2011 | Thurieau et al. | |
| 2013/0040978 A1 | 2/2013 | Duffy et al. | |
| 2015/0232478 A1 | 8/2015 | Ishida et al. | |
| 2016/0311794 A1 | 10/2016 | Ishida et al. | |
| 2020/0000816 A1 | 1/2020 | Ishida et al. | |
| 2020/0010453 A1 | 1/2020 | Han et al. | |
| 2021/0040087 A1 | 2/2021 | Zhao et al. | |
| 2021/0047287 A1 | 2/2021 | Zhao et al. | |

FOREIGN PATENT DOCUMENTS

| | | |
|---|---|---|
| CA | 2925651 A1 | 4/2015 |
| EP | 3053916 A1 | 8/2016 |
| EP | 3053961 A1 | 8/2016 |
| EP | 3053916 B1 | 1/2019 |
| EP | 3581569 A1 | 12/2019 |
| WO | WO-2008051272 A2 | 5/2008 |
| WO | WO-2009051705 A1 | 4/2009 |
| WO | WO-2009158467 A2 | 12/2009 |
| WO | WO-2010041054 A1 | 4/2010 |
| WO | WO-2011027249 A2 | 3/2011 |
| WO | WO-2011144891 A1 | 11/2011 |
| WO | WO-2014007228 A1 | 1/2014 |
| WO | WO-2015046482 A1 | 4/2015 |
| WO | WO-2018013676 A1 | 1/2018 |
| WO | 2018170284 * | 3/2018 |
| WO | WO-2018147300 A1 | 8/2018 |
| WO | WO-2018170284 A1 | 9/2018 |
| WO | WO-2019023278 A1 | 1/2019 |
| WO | WO-2019157458 A1 | 8/2019 |
| WO | WO-2020061046 A1 | 3/2020 |
| WO | WO-2021030262 A1 | 2/2021 |

OTHER PUBLICATIONS

Abbott et al. MiRP1 forms IKr potassium channels with HERG and is associated with cardiac arrhythmia. Cell 97:175-187 (1999).
Berge et al. Pharmaceutical Salts. Journal of Pharmaceutical Sciences 66(1): 1-19 (Jan. 1977).
Brazeau et al. Hypothalamic polypeptide that inhibits the secretion of immunoreactive pituitary growth hormone. Science 179:77-79 (1973).
Bundgaard. Design and Application of Prodrugs. Textbook of Drug Design and Development. Krosgaard-Larsen and Bundgaard. Chapter 5, pp. 113-191 (1991).
Bundgaard. Means to Enhance Penetration: Prodrugs as a Means to Improve the Delivery of Peptide Drugs. Advanced Drug Delivery Review 8:1-38 (1992).
Crider. Somatostatin receptor agonists and antagonists. Expert Opinion on Therapeutic Patents 13(9):1427-1441 (2003).
Esch et al. Primary structure of ovine hypothalamic somatostatin-28 and somatostatin-25. PNAS USA 77:6827-6831 (1980).
Khlebnikov et al. A Novel Strategy for the Synthesis of 3-(N-Heteryl)pyrrole Derivatives. Org Lett 14(14):3768-71 (2012).
Mallinger et al. Discovery of Potent, Orally Bioavailable, Small-Molecule Inhibitors of WNT Signaling from a Cell-Based Pathway Screen. J Med Chem 58(4):1717-35 (2015).

(Continued)

*Primary Examiner* — Niloofar Rahmani
(74) *Attorney, Agent, or Firm* — Wilson Sonsini Goodrich & Rosati

(57) ABSTRACT

Described herein are compounds that are somatostatin modulators, methods of making such compounds, pharmaceutical compositions and medicaments comprising such compounds, and methods of using such compounds in the treatment of conditions, diseases, or disorders that would benefit from modulation of somatostatin activity.

11 Claims, No Drawings

(56) References Cited

OTHER PUBLICATIONS

Ortiz-Marciales et al. Catalytic enantioselective borane reduction of benzyl oximes: preparation of (S)-1-Pyridin-3-Yl-Ethylamine Bis Hydrochloride. Organic Synth. 87:36-52 (2010).
Patel et al. Somatostatin receptors. Trends Endocrinol Metab 8:398-405 (1997).
PCT/US2019/051514 International Search Report and Written Opinion dated Jan. 3, 2020.
Pradayrol et al. N-terminally extended somatostatin: the primary structure of somatostatin-28. FEBS Letters 109:55-58 (1980).
Reisine et al. Molecular biology of somatostatin receptors. Endocr Rev 16:427-442 (1995).
Sanguinetti et al. hERG potassium channels and cardiac arrhythmia. Nature 440(7083):463-469 (2006).
Science IP Report. Chemical Structure Search (May 24, 2016) (311 pgs.).
Stella. Prodrugs: Some Thoughts and Current Issues. J Pharm Sci 99(12):4755-4765 (2010).
Weckbecker et al. Opportunities in somatostatin research: biological, chemical and therapeutic aspects. Nat Rev Drug Discov 2(12):999-1017 (2003).
Widder et al. Section III: Prodrugs Kinetics. Method in Enzymology. 112:309-396 (1985).
Wolf et al. Cytochrome P450 CYP2D6. IARC Sci Publ 148:209-229 (1999).
Wolkenberg et al. Design, synthesis, and evaluation of novel 3,6-diaryl-4-aminoalkoxyquinolines as selective agonists of somatostatin receptor subtype 2. J Med Chem 54:2351-2358 (2011).

* cited by examiner

SOMATOSTATIN MODULATORS AND USES THEREOF

RELATED APPLICATIONS

This application is a Continuation of U.S. patent application Ser. No. 16/572,921 filed Sep. 17, 2019, which claims the benefit of U.S. Provisional Patent Application No. 62/732,735 filed on Sep. 18, 2018, both of which are herein incorporated by reference in their entireties.

STATEMENT AS TO FEDERALLY SPONSORED RESEARCH

This invention was made with government support under NS092231 awarded by the National Institutes of Health. The government has certain rights in this invention.

FIELD OF THE INVENTION

Described herein are compounds that are somatostatin modulators, methods of making such compounds, pharmaceutical compositions and medicaments comprising such compounds, and methods of using such compounds in the treatment of conditions, diseases, or disorders that would benefit from modulating somatostatin activity.

BACKGROUND OF THE INVENTION

Somatostatin is a peptide hormone that regulates the endocrine system and affects neurotransmission and cell proliferation via interaction with G-protein-coupled somatostatin receptors and inhibition of the release of numerous secondary hormones. Six subtype somatostatin receptor proteins have been identified (SSTR1, SSTR2a, SSTR2b, SSTR3, SSTR4, SSTR5) and are encoded by five different somatostatin receptor genes. Modulation of a particular subtype somatostatin receptor or combination thereof, is attractive for the treatment of conditions, diseases, or disorders that would benefit from modulating somatostatin activity.

SUMMARY OF THE INVENTION

Compounds described herein are somatostatin modulator compounds. In some embodiments, compounds described herein modulate one or more of the subtype somatostatin receptor proteins. In some embodiments, compounds described herein modulate one subtype somatostatin receptor. In some embodiments, compounds described herein modulate SSTR2 somatostatin receptor. Somatostatin peptide analogs, such as octreotide and pasireotide, formulated as depot injections, are routinely used to normalize hormone levels for the treatment of Growth Hormone (GH) secreting adenomas, pancreatic neuroendocrine tumors, and carcinoid tumors. Unfortunately, these analogs are only effective in about half of acromegalic patients with GH adenomas, and patients with carcinoid tumors frequently become resistant to therapy due to internalization and desensitization of the SST2a receptor. In addition, these peptide drugs are extremely expensive and require frequent doctor's office visits for painful injections that can lead to injection site reactions. Compounds described herein are molecules that are structurally different from peptide analogs. The compounds described herein are somatostatin modulators that are potent inhibitors of hormone secretion.

In one aspect, described herein is a compound of Formula (I), or a pharmaceutically acceptable salt, pharmaceutically acceptable solvate, diastereomeric mixture, or individual enantiomer thereof:

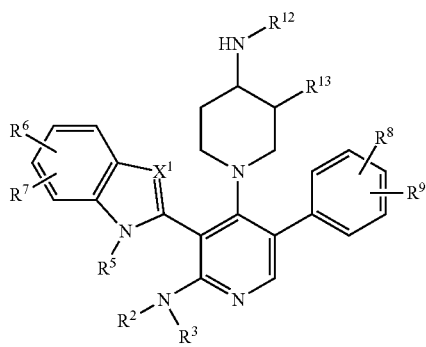

Formula (I)

wherein:

$R^2$ is hydrogen, substituted or unsubstituted $C_1$-$C_4$alkyl, substituted or unsubstituted $C_1$-$C_4$fluoroalkyl, substituted or unsubstituted $C_1$-$C_4$heteroalkyl, or substituted or unsubstituted $C_3$-$C_6$cycloalkyl;

$R^3$ is hydrogen, substituted or unsubstituted $C_1$-$C_4$alkyl, substituted or unsubstituted $C_1$-$C_4$fluoroalkyl, substituted or unsubstituted $C_1$-$C_4$heteroalkyl, or substituted or unsubstituted $C_3$-$C_6$cycloalkyl;

or $R^2$ and $R^3$ are taken together with the N atom to which they are attached to form a substituted or unsubstituted 4-membered, substituted or unsubstituted 5-membered or substituted or unsubstituted 6-membered N-containing heterocyclic ring;

$R^5$ is hydrogen, substituted or unsubstituted $C_1$-$C_4$alkyl, substituted or unsubstituted $C_1$-$C_4$fluoroalkyl, substituted or unsubstituted $C_2$-$C_4$alkenyl, or substituted or unsubstituted $C_3$-$C_6$cycloalkyl;

$R^6$ is substituted or unsubstituted $C_1$-$C_4$alkyl, substituted or unsubstituted $C_1$-$C_4$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted monocyclic carbocycle, substituted or unsubstituted monocyclic heterocycle, —CN, —$OR^{15}$, —$CO_2R^{15}$, —C(=O)N($R^{15}$)$_2$, —C(=O)N($R^{15}$)$OR^{15}$, —N($R^{15}$)$_2$, —$NR^{15}$C(=O)$R^{15}$, or —C($R^{15}$)=N—$OR^{15}$;

$R^7$ is —CN;

each $R^8$ and $R^9$ is independently hydrogen, halogen, substituted or unsubstituted $C_1$-$C_4$alkyl, substituted or unsubstituted $C_1$-$C_4$fluoroalkyl, substituted or unsubstituted $C_1$-$C_6$heteroalkyl, —CN, —OH, or substituted or unsubstituted $C_1$-$C_4$alkoxy; $X^1$ is N or C—$R^{10}$;

$R^{10}$ is hydrogen, F, Cl, Br, —CN, —N($R^{15}$)$_2$, substituted or unsubstituted $C_1$-$C_4$alkyl, substituted or unsubstituted $C_1$-$C_4$alkoxy, substituted or unsubstituted $C_1$-$C_4$fluoroalkyl, substituted or unsubstituted $C_1$-$C_4$fluoroalkoxy, substituted or unsubstituted $C_1$-$C_4$heteroalkyl, or substituted or unsubstituted $C_3$-$C_6$cycloalkyl;

$R^{12}$ is hydrogen, or substituted or unsubstituted $C_1$-$C_6$alkyl;

$R^{13}$ is hydrogen, $-N(R^{16})_2$, $-CN$, $-CO_2R^{14}$, $-C(=O)N(R^{15})_2$, $-OR^{16}$, substituted or unsubstituted $C_1$-$C_6$alkyl, substituted or unsubstituted $C_1$-$C_6$fluoroalkyl, or substituted or unsubstituted $C_1$-$C_6$heteroalkyl;

or $R^{12}$ and $R^{13}$ are taken together with the intervening atoms to which they are attached to form a substituted or unsubstituted N-containing heterocyclic ring;

or $R^{12}$ and $R^{16}$ are taken together with the intervening atoms to which they are attached to form a substituted or unsubstituted N-containing heterocyclic ring;

each $R^{14}$ is independently selected from substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;

each $R^{15}$ is independently selected from hydrogen, substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;

or two $R^{15}$ on the same N atom are taken together with the N atom to which they are attached to form a substituted or unsubstituted N-containing heterocycle;

each $R^{16}$ is independently selected from hydrogen, substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;

or two $R^{16}$ on the same N atom are taken together with the N atom to which they are attached to form a substituted or unsubstituted N-containing heterocycle.

In some embodiments, the compound of Formula (I) has the structure of Formula (Ia), or a pharmaceutically acceptable salt, pharmaceutically acceptable solvate, diastereomeric mixture, or individual enantiomer thereof:

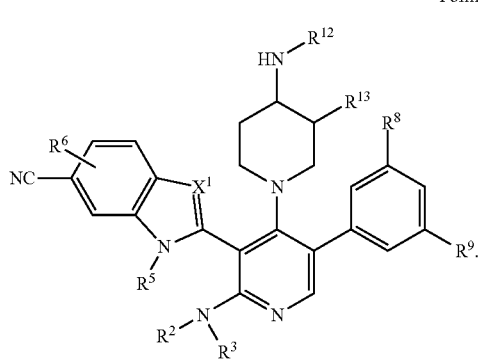

Formula (Ia)

In some embodiments, the compound of Formula (I) has the structure of Formula (Ib), or a pharmaceutically acceptable salt, pharmaceutically acceptable solvate, diastereomeric mixture, or individual enantiomer thereof:

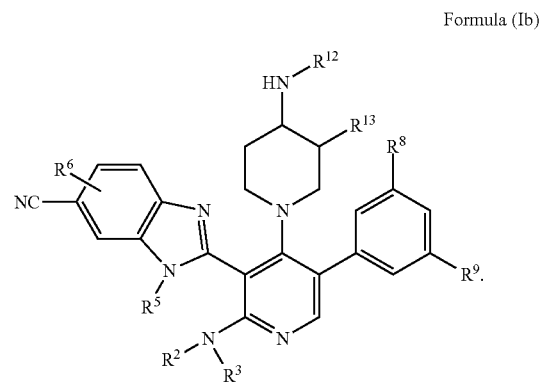

Formula (Ib)

In some embodiments, the compound of Formula (I) has the following structure of Formula (Ic), or a pharmaceutically acceptable salt, pharmaceutically acceptable solvate, diastereomeric mixture, or individual enantiomer thereof:

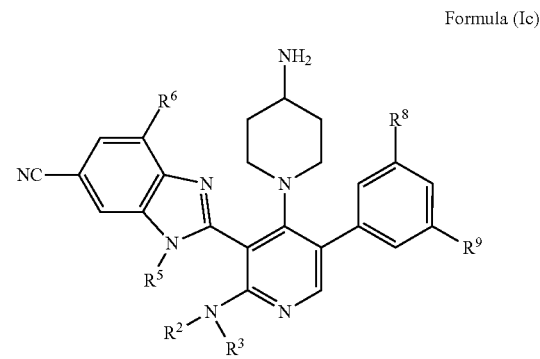

Formula (Ic)

wherein:

$R^2$ is hydrogen or substituted or unsubstituted $C_1$-$C_4$alkyl;

$R^3$ is hydrogen or substituted or unsubstituted $C_1$-$C_4$alkyl;

or $R^2$ and $R^3$ are taken together with the N atom to which they are attached to form a substituted or unsubstituted 5-membered or substituted or unsubstituted 6-membered N-containing heterocyclic ring;

$R^5$ is hydrogen or substituted or unsubstituted $C_1$-$C_4$alkyl;

$R^6$ is substituted or unsubstituted $C_1$-$C_4$alkyl, substituted or unsubstituted $C_1$-$C_4$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted monocyclic carbocycle, substituted or unsubstituted monocyclic heterocycle, $-CN$, $-OR^{15}$, $-CO_2R^{15}$, $-C(=O)N(R^{15})_2$, $-C(=O)N(R^{15})OR^{15}$, $-N(R^{15})_2$, $-NR^{15}C(=O)R^{15}$, or $-C(R^{15})=N-OR^{15}$;

each $R^8$ and $R^9$ is independently hydrogen, halogen, substituted or unsubstituted $C_1$-$C_4$alkyl, substituted or unsubstituted $C_1$-$C_4$fluoroalkyl, substituted or unsubstituted $C_1$-$C_6$heteroalkyl, $-CN$, $-OH$, or substituted or unsubstituted $C_1$-$C_4$alkoxy;

each $R^{15}$ is independently selected from hydrogen, substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;

or two R¹⁵ on the same N atom are taken together with the N atom to which they are attached to form a substituted or unsubstituted N-containing heterocycle.

In one aspect, described herein is a compound of Formula (II), or a pharmaceutically acceptable salt, pharmaceutically acceptable solvate, diastereomeric mixture, or individual enantiomer thereof:

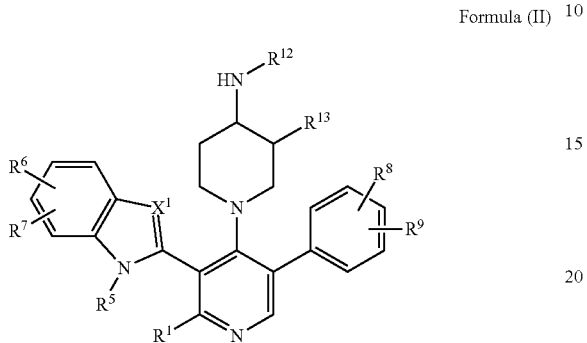

Formula (II)

wherein:
R¹ is —CN, —CO₂R¹⁵, —C(=O)N(R¹⁵)₂, —S(=O)₂R¹⁵, or —S(=O)₂N(R¹⁵)₂;
R⁵ is hydrogen, substituted or unsubstituted $C_1$-$C_4$alkyl, substituted or unsubstituted $C_1$-$C_4$fluoroalkyl, substituted or unsubstituted $C_2$-$C_4$alkenyl, or substituted or unsubstituted $C_3$-$C_6$cycloalkyl;
each R⁶ and R⁷ is independently halogen, substituted or unsubstituted $C_1$-$C_4$alkyl, substituted or unsubstituted $C_1$-$C_4$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted monocyclic carbocycle, substituted or unsubstituted monocyclic heterocycle, —CN, —OR¹⁵, —CO₂R¹⁵, —C(=O)N(R¹⁵)₂, —C(=O)N(R¹⁵)OR¹⁵, —N(R¹⁵)₂, —NR¹⁵C(=O)R¹⁵, or —C(R¹⁵)=N—OR¹⁵;
each R⁸ and R⁹ is independently hydrogen, halogen, substituted or unsubstituted $C_1$-$C_4$alkyl, substituted or unsubstituted $C_1$-$C_4$fluoroalkyl, substituted or unsubstituted $C_1$-$C_6$heteroalkyl, —CN, —OH, or substituted or unsubstituted $C_1$-$C_4$alkoxy; X¹ is N or C—R¹⁰;
R¹⁰ is hydrogen, F, Cl, Br, —CN, —N(R¹⁵)₂, substituted or unsubstituted $C_1$-$C_4$alkyl, substituted or unsubstituted $C_1$-$C_4$alkoxy, substituted or unsubstituted $C_1$-$C_4$fluoroalkyl, substituted or unsubstituted $C_1$-$C_4$fluoroalkoxy, substituted or unsubstituted $C_1$-$C_4$heteroalkyl, or substituted or unsubstituted $C_3$-$C_6$cycloalkyl;
R¹² is hydrogen, or substituted or unsubstituted $C_1$-$C_6$alkyl;
R¹³ is hydrogen, —N(R¹⁶)₂, —CN, —CO₂R¹⁴, —C(=O)N(R¹⁵)₂, —OR¹⁶, substituted or unsubstituted $C_1$-$C_6$alkyl, substituted or unsubstituted $C_1$-$C_6$fluoroalkyl, or substituted or unsubstituted $C_1$-$C_6$heteroalkyl;
or R¹² and R¹³ are taken together with the intervening atoms to which they are attached to form a substituted or unsubstituted N-containing heterocyclic ring;
or R¹² and R¹⁶ are taken together with the intervening atoms to which they are attached to form a substituted or unsubstituted N-containing heterocyclic ring;
each R¹⁴ is independently selected from substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;
each R¹⁵ is independently selected from hydrogen, substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;
or two R¹⁵ on the same N atom are taken together with the N atom to which they are attached to form a substituted or unsubstituted N-containing heterocycle;
each R¹⁶ is independently selected from hydrogen, substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;
or two R¹⁶ on the same N atom are taken together with the N atom to which they are attached to form a substituted or unsubstituted N-containing heterocycle.

In some embodiments, the compound of Formula (II) has the structure of Formula (IIa), or a pharmaceutically acceptable salt, pharmaceutically acceptable solvate, diastereomeric mixture, or individual enantiomer thereof:

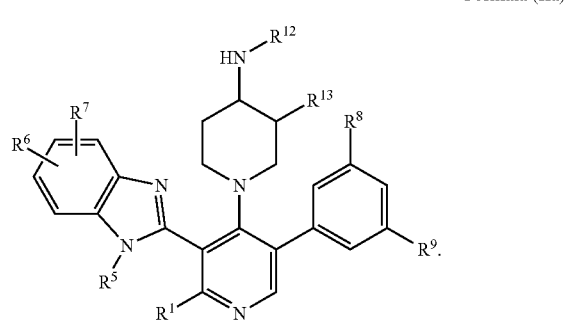

Formula (IIa)

In some embodiments, the compound of Formula (II) has the structure of Formula (IIb), or a pharmaceutically acceptable salt, pharmaceutically acceptable solvate, diastereomeric mixture, or individual enantiomer thereof:

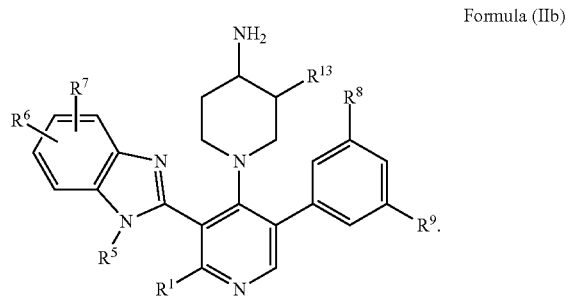

Formula (IIb)

In some embodiments, the compound of Formula (II) has the following structure of Formula (IIc), or a pharmaceutically acceptable salt, pharmaceutically acceptable solvate, diastereomeric mixture, or individual enantiomer thereof:

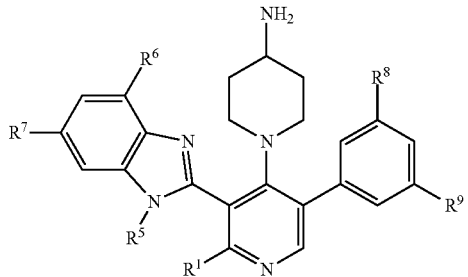

Formula (IIc)

wherein:
R$^1$ is —CN, —CO$_2$R$^{15}$, or —C(=O)N(R$^{15}$)$_2$;
R$^5$ is hydrogen or substituted or unsubstituted C$_1$-C$_4$alkyl;
each R$^6$ and R$^7$ is independently halogen, substituted or unsubstituted C$_1$-C$_4$alkyl, substituted or unsubstituted C$_1$-C$_4$fluoroalkyl, substituted or unsubstituted C$_2$-C$_4$alkenyl, substituted or unsubstituted C$_2$-C$_4$alkynyl, substituted or unsubstituted C$_1$-C$_6$heteroalkyl, substituted or unsubstituted monocyclic carbocycle, substituted or unsubstituted monocyclic heterocycle, —CN, —OR$^{15}$, —CO$_2$R$^{15}$, —C(=O)N(R$^{15}$)$_2$, —C(=O)N(R$^{15}$)OR$^{15}$, —N(R$^{15}$)$_2$, —NR$^{15}$C(=O)R$^{15}$, or —C(R$^{15}$)=N—OR$^{15}$;
each R$^8$ and R$^9$ is independently hydrogen, halogen, substituted or unsubstituted C$_1$-C$_4$alkyl, substituted or unsubstituted C$_1$-C$_4$fluoroalkyl, substituted or unsubstituted C$_1$-C$_6$heteroalkyl, —CN, —OH, or substituted or unsubstituted C$_1$-C$_4$alkoxy;
each R$^{15}$ is independently selected from hydrogen, substituted or unsubstituted C$_1$-C$_6$alkyl, substituted or unsubstituted C$_1$-C$_6$heteroalkyl, substituted or unsubstituted C$_3$-C$_7$cycloalkyl, substituted or unsubstituted monocyclic C$_2$-C$_6$heterocycloalkyl, substituted or unsubstituted phenyl, and substituted or unsubstituted monocyclic heteroaryl;
or two R$^{15}$ on the same N atom are taken together with the N atom to which they are attached to form a substituted or unsubstituted N-containing heterocycle.

In another aspect, described herein is a compound of Formula (III), or a pharmaceutically acceptable salt, pharmaceutically acceptable solvate, diastereomeric mixture, or individual enantiomer thereof:

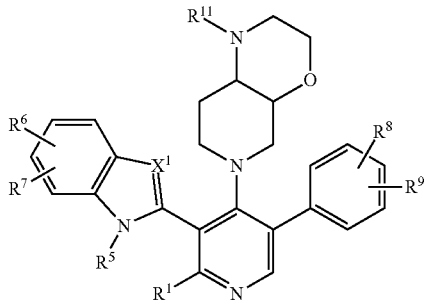

Formula (III)

wherein:
R$^1$ is —NR$^2$R$^3$, —OR$^2$, or R$^4$;
R$^2$ is hydrogen, substituted or unsubstituted C$_1$-C$_4$alkyl, substituted or unsubstituted C$_1$-C$_4$fluoroalkyl, substituted or unsubstituted C$_1$-C$_4$heteroalkyl, or substituted or unsubstituted C$_3$-C$_6$cycloalkyl;
R$^3$ is hydrogen, substituted or unsubstituted C$_1$-C$_4$alkyl, substituted or unsubstituted C$_1$-C$_4$fluoroalkyl, substituted or unsubstituted C$_1$-C$_4$heteroalkyl, or substituted or unsubstituted C$_3$-C$_6$cycloalkyl;
or R$^2$ and R$^3$ are taken together with the N atom to which they are attached to form a substituted or unsubstituted 4-membered, substituted or unsubstituted 5-membered or substituted or unsubstituted 6-membered N-containing heterocyclic ring;
R$^4$ is F, Cl, Br, —CN, substituted or unsubstituted C$_1$-C$_4$alkyl, substituted or unsubstituted C$_1$-C$_4$fluoroalkyl, substituted or unsubstituted C$_1$-C$_4$alkoxy, —SC$_1$-C$_4$alkyl, —S(=O)C$_1$-C$_4$alkyl, —S(=O)$_2$—C$_1$-C$_4$alkyl, substituted or unsubstituted C$_1$-C$_4$heteroalkyl, substituted or unsubstituted C$_3$-C$_6$cycloalkyl, —CO$_2$R$^{15}$, —C(=O)N(R$^{15}$)$_2$;
R$^5$ is hydrogen, substituted or unsubstituted C$_1$-C$_4$alkyl, substituted or unsubstituted C$_1$-C$_4$fluoroalkyl, substituted or unsubstituted C$_2$-C$_4$alkenyl, or substituted or unsubstituted C$_3$-C$_6$cycloalkyl;
each R$^6$ and R$^7$ is independently halogen, substituted or unsubstituted C$_1$-C$_4$alkyl, substituted or unsubstituted C$_1$-C$_4$fluoroalkyl, substituted or unsubstituted C$_2$-C$_4$alkenyl, substituted or unsubstituted C$_2$-C$_4$alkynyl, substituted or unsubstituted C$_1$-C$_6$heteroalkyl, substituted or unsubstituted monocyclic carbocycle, substituted or unsubstituted monocyclic heterocycle, —CN, —OR$^{15}$, —CO$_2$R$^{15}$, —C(=O)N(R$^{15}$)$_2$, —C(=O)N(R$^{15}$)OR$^{15}$, —N(R$^{15}$)$_2$, —NR$^{15}$C(=O)R$^{15}$, or —C(R$^{15}$)=N—OR$^{15}$;
each R$^8$ and R$^9$ is independently hydrogen, halogen, substituted or unsubstituted C$_1$-C$_4$alkyl, substituted or unsubstituted C$_1$-C$_4$fluoroalkyl, substituted or unsubstituted C$_1$-C$_6$heteroalkyl, —CN, —OH, or substituted or unsubstituted C$_1$-C$_4$alkoxy;
X$^1$ is N or C—R$^{10}$;
R$^{10}$ is hydrogen, F, Cl, Br, —CN, —N(R$^{15}$)$_2$, substituted or unsubstituted C$_1$-C$_4$alkyl, substituted or unsubstituted C$_1$-C$_4$alkoxy, substituted or unsubstituted C$_1$-C$_4$fluoroalkyl, substituted or unsubstituted C$_1$-C$_4$fluoroalkoxy, substituted or unsubstituted C$_1$-C$_4$heteroalkyl, or substituted or unsubstituted C$_3$-C$_6$cycloalkyl;
R$^{11}$ is hydrogen or substituted or unsubstituted C$_1$-C$_6$alkyl;
each R$^{15}$ is independently selected from hydrogen, substituted or unsubstituted C$_1$-C$_6$alkyl, substituted or unsubstituted C$_1$-C$_6$heteroalkyl, substituted or unsubstituted C$_3$-C$_7$cycloalkyl, substituted or unsubstituted monocyclic C$_2$-C$_6$heterocycloalkyl, substituted or unsubstituted phenyl, and substituted or unsubstituted monocyclic heteroaryl;
or two R$^{15}$ on the same N atom are taken together with the N atom to which they are attached to form a substituted or unsubstituted N-containing heterocycle.

In some embodiments, the compound of Formula (III) has the following structure of Formula (IIIa), or a pharmaceutically acceptable salt, pharmaceutically acceptable solvate, diastereomeric mixture, or individual enantiomer thereof:

Formula (IIIa)

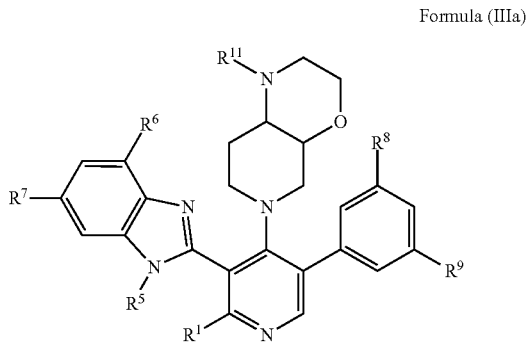

wherein:
R¹ is —NR²R³, —OR², F, Cl, Br, —CN, C₁-C₄alkyl, or C₁-C₄fluoroalkyl;
R² is hydrogen or substituted or unsubstituted C₁-C₄alkyl;
R³ is hydrogen or substituted or unsubstituted C₁-C₄alkyl;
or R² and R³ are taken together with the N atom to which they are attached to form a substituted or unsubstituted 5-membered or substituted or unsubstituted 6-membered N-containing heterocyclic ring;
R⁵ is hydrogen or substituted or unsubstituted C₁-C₄alkyl;
each R⁶ and R⁷ is independently halogen, substituted or unsubstituted C₁-C₄alkyl, substituted or unsubstituted C₁-C₄fluoroalkyl, substituted or unsubstituted C₂-C₄alkenyl, substituted or unsubstituted C₂-C₄alkynyl, substituted or unsubstituted C₁-C₆heteroalkyl, substituted or unsubstituted monocyclic carbocycle, substituted or unsubstituted monocyclic heterocycle, —CN, —OR¹⁵, —CO₂R¹⁵, —C(=O)N(R¹⁵)₂, —C(=O)N(R¹⁵)OR¹⁵, —N(R¹⁵)₂, —NR¹⁵C(=O)R¹⁵, or —C(R¹⁵)=N—OR¹⁵;
each R⁸ and R⁹ is independently hydrogen, halogen, substituted or unsubstituted C₁-C₄alkyl, substituted or unsubstituted C₁-C₄fluoroalkyl, substituted or unsubstituted C₁-C₆heteroalkyl, —CN, —OH, or substituted or unsubstituted C₁-C₄alkoxy;
R¹¹ is hydrogen or substituted or unsubstituted C₁-C₄alkyl;
each R¹⁵ is independently selected from hydrogen, substituted or unsubstituted C₁-C₆alkyl, substituted or unsubstituted C₁-C₆heteroalkyl, substituted or unsubstituted C₃-C₇cycloalkyl, substituted or unsubstituted monocyclic C₂-C₆heterocycloalkyl, substituted or unsubstituted phenyl, and substituted or unsubstituted monocyclic heteroaryl;
or two R¹⁵ on the same N atom are taken together with the N atom to which they are attached to form a substituted or unsubstituted N-containing heterocycle.

Any combination of the groups described above for the various variables is contemplated herein. Throughout the specification, groups and substituents thereof are chosen by one skilled in the field to provide stable moieties and compounds.

Also described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by oral administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule.

Also described herein is a method of treating a disease or condition in a mammal that would benefit from the modulation of somatostatin receptor activity comprising administering a small molecule non-peptidyl compound, or pharmaceutically acceptable salt, or solvate thereof, to the mammal in need thereof. In some embodiments, the small molecule non-peptidyl compound is orally administered. In some embodiments, the small molecule non-peptidyl compound is a compound as described herein, or a pharmaceutically acceptable salt or solvate thereof. In some embodiments, the small molecule non-peptidyl compound is a SSTR2 modulator as described herein, or a pharmaceutically acceptable salt or solvate thereof. In some embodiments, the disease or condition is acromegaly, a neuroendocrine tumor, an ophthalmic disease or condition, neuropathy, nephropathy, a respiratory disease or condition, cancer, pain, a neurodegenerative disease or condition, an inflammatory disease or condition, a psychiatric disease or condition, or combinations thereof.

In any of the aforementioned aspects are further embodiments in which the effective amount of the compound of Formula (I), Formula (II), or Formula (III), or a pharmaceutically acceptable salt thereof, is: (a) systemically administered to the mammal; and/or (b) administered orally to the mammal; and/or (c) intravenously administered to the mammal; and/or (d) administered by inhalation; and/or (e) administered by nasal administration; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the embodiments disclosed herein, the mammal is a human.

In some embodiments, compounds provided herein are orally administered to a human.

Articles of manufacture, which include packaging material, a compound of Formula (I), Formula (II), or Formula (III), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for modulating one or more subtype somatostatin receptor proteins, or for the treatment, prevention or amelioration of one or more symptoms of a disease or condition that would benefit from modulating one or more subtype somatostatin receptor proteins, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Somatostatin (SST), also known as somatotropin release inhibiting factor (SRIF) was initially isolated as a 14-amino acid peptide from ovine hypothalamii (Brazeau et al., *Science* 179, 77-79, 1973). An N-terminal extended 28-amino acid peptide with similar biological activity to 14-amino acid somatostatin was subsequently isolated (Pradayrol et, al., *FEBS Letters*, 109, 55-58, 1980; Each et al., *Proc. Natl. Acad. Sci. USA*, 77, 6827-6831, 1980). SST is a regulatory peptide produced by several cell types in response to other neuropeptides, neurotransmitters, hormones, cytokines, and growth factors. SST acts through both endocrine and paracrine pathways to affect its target cells. Many of these effects are related to the inhibition of secretion of other hormones, most notably growth hormone (GH). They are produced by a wide variety of cell types in the central nervous system (CNS) and gut and have multiple functions including modulation of secretion of growth hormone (GH), insulin, glucagon, as well as many other hormones that are anti-proliferative.

These pleotropic actions of somatostatins are mediated by six somatostatin receptor proteins (SSTR1, SSTR2a, SSTR2b, SSTR3, SSTR4, SSTR5). The six somatostatin receptor proteins are encoded by five different somatostatin receptor genes (Reisine and Bell, *Endocr Rev.* 16, 427-442, 1995; Patel and Srikant, *Trends Endocrinol Metab* 8, 398-405, 1997). All the receptors are members of the class-A subgroup of the GPCR superfamily. SST2a receptor is the most widely expressed subtype in human tumors and is the dominant receptor by which GH secretion is suppressed. Unless otherwise stated, the term SSTR2 means SSTR2a.

It is possible to selectively modulate any one of the somatostatin receptor subtypes, or combination thereof. In some embodiments, selectively modulating any one of the somatostatin receptor subtypes relative to the other somatostatin receptor subtypes reduces unwanted side effects in a variety of clinical applications.

For example, selective modulation of SSTR2 activity mediates the inhibition of growth hormone (GH) release from the anterior pituitary and glucagon release from pancreas. SSTR2 is also implicated in many other biological functions such as, but not limited to, cell proliferation, nociception, inflammation, and angiogenesis. In some embodiments, a selective SSTR2 modulator is used in the treatment of acromegaly, neuroendocrine tumors, pain, neuropathies, nephropathies, and inflammation, as well as retinopathies resulting from aberrant blood vessel growth. In some other embodiments, a selective SSTR2 modulator is used in the treatment of arthritis, pain, cancer, inflammatory bowel disease, irritable bowel syndrome, Crohn's disease, Cushing's disease, acute lung injury, acute respiratory distress syndrome, and ophthalmic disorders such as age-related macular degeneration (AMD), diabetic retinopathy, diabetic macular edema, and Graves ophthalmology, among others.

In one aspect, compounds described herein are modulators of SSTR2. In some embodiments, compounds described herein selectively modulate the activity of SSTR2 relative to the other somatostatin receptors.

In some embodiments, compounds described here are amenable to oral administration to a mammal in need of treatment with a somatostatin modulator.

In some embodiments, somatostatin receptor modulators described herein have utility over a wide range of therapeutic applications. In some embodiments, somatostatin receptor modulators described herein are used in the treatment of a variety of diseases or conditions such as, but not limited to acromegaly, neuroendocrine tumors, retinopathies and other ophthalmic disorders, neuropathy, nephropathy, respiratory diseases, cancers, pain, neurodegenerative diseases, inflammatory diseases, as well as psychiatric and neurodegenerative disorders. In some embodiments, somatostatin receptor modulators described herein are used in the treatment of acromegaly in a mammal.

In some embodiments, somatostatin receptor modulators described herein inhibit the secretion of various hormones and trophic factors in mammals. In some embodiments, the compounds are used to suppress certain endocrine secretions, such as, but not limited to GH, insulin, glucagon and prolactin. The suppression of certain endocrine secretions is useful in the treatment of disorders such as acromegaly; endocrine tumors such as carcinoids, VlPomas, insulinomas and glucagonomas; or diabetes and diabetes-related pathologies, including retinopathy, neuropathy and nephropathy. In some embodiments, somatostatin receptor modulators described herein are used to suppress exocrine secretions in the pancreas, stomach and intestines, for the treatment of disorders such as pancreatitis, fistulas, bleeding ulcers and diarrhea associated with such diseases as AIDS or cholera. Disorders involving autocrine or paracrine secretions of trophic factors such as IGF-1 (as well as some endocrine factors) which may be treated by administration of the compounds described herein include cancers of the breast, prostate, and lung (both small cell and non-small cell epidermoids), as well as hepatomas, neuroblastomas, colon and pancreatic adenocarcinomas (ductal type), chondrosarcomas, and melanomas, diabetic retinopathy, and atherosclerosis associated with vascular grafts and restenosis following angioplasty.

In some embodiments, somatostatin receptor modulators described herein are used to suppress the mediators of neurogenic inflammation (e.g. substance P or the tachykinins), and may be used in the treatment of rheumatoid arthritis; psoriasis; topical inflammation such as is associated with sunburn, eczema, or other sources of itching; inflammatory bowel disease; irritable bowel syndrome; allergies, including asthma and other respiratory diseases In some other embodiments, the somatostatin receptor modulators described herein function as neuromodulators in the central nervous system and are useful in the treatment of Alzheimer's disease and other forms of dementia, pain, and headaches. In some embodiments, somatostatin receptor modulators described herein provide cytoprotection in disorders involving the splanchnic blood flow, including cirrhosis and oesophagal varices.

Compounds

Compounds of Formula (I), Formula (II), or Formula (III), including pharmaceutically acceptable salts, prodrugs, active metabolites and pharmaceutically acceptable solvates thereof, are somatostatin receptor modulators. In some embodiments, the compounds of Formula (I), Formula (II), or Formula (III), including pharmaceutically acceptable salts, prodrugs, active metabolites and pharmaceutically acceptable solvates thereof, are SSTR2 modulators. In some embodiments, the somatostatin receptor modulators are somatostatin receptor agonists.

In some embodiments, compounds described herein are at least 2 times, at least 3 times, at least 4 times, at least 5 times, at least 6 times, at least 7 times, at least 8 times, at least 9 times, at least 10 times, at least 15 times, at least 20 times, at least 30 times, at least 40 times, at least 50 times, at least 100 times, at least 200 times more selective at modulating SSTR2 activity than SSTR4 receptor activity. In some embodiments, the $R^1$ group of the compounds described herein confers selectivity for modulating SSTR2 activity.

In some embodiments, it is desirable that SSTR2 modulators have increased water solubility and reduced possibility to be BBB penetrable by increasing hydrogen bond donors. In some embodiments, the $R^1$ group of the compounds described herein reduced liability associated BBB penetration. In some embodiments, the $R^1$ group of the compounds herein described increased water solubility.

In some embodiments, it is desirable that SSTR2 modulators have reduced metabolic instability. In some embodiments, the $R^1$ group of the compounds herein described reduce metabolic instability in human liver microsomes. In some embodiments, $R^1$ corresponds to —$NR^2R^3$ of Formula (I).

In one aspect, provided herein is a compound of Formula (I), or a pharmaceutically acceptable salt, pharmaceutically acceptable solvate, diastereomeric mixture, individual enantiomers thereof:

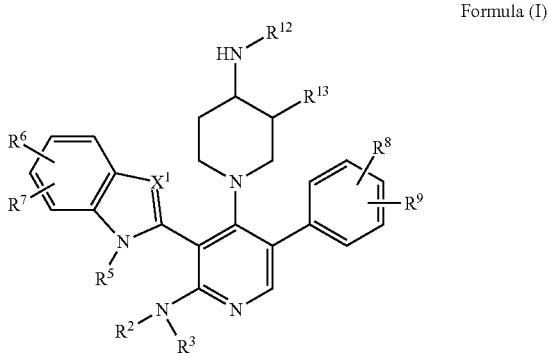

Formula (I)

wherein:
$R^2$ is hydrogen, substituted or unsubstituted $C_1$-$C_4$alkyl, substituted or unsubstituted $C_1$-$C_4$fluoroalkyl, substituted or unsubstituted $C_1$-$C_4$heteroalkyl, or substituted or unsubstituted $C_3$-$C_6$cycloalkyl;
$R^3$ is hydrogen, substituted or unsubstituted $C_1$-$C_4$alkyl, substituted or unsubstituted $C_1$-$C_4$fluoroalkyl, substituted or unsubstituted $C_1$-$C_4$heteroalkyl, or substituted or unsubstituted $C_3$-$C_6$cycloalkyl;
or $R^2$ and $R^3$ are taken together with the N atom to which they are attached to form a substituted or unsubstituted 4-membered, substituted or unsubstituted 5-membered or substituted or unsubstituted 6-membered N-containing heterocyclic ring;
$R^5$ is hydrogen, substituted or unsubstituted $C_1$-$C_4$alkyl, substituted or unsubstituted $C_1$-$C_4$fluoroalkyl, substituted or unsubstituted $C_2$-$C_4$alkenyl, or substituted or unsubstituted $C_3$-$C_6$cycloalkyl;
$R^6$ is substituted or unsubstituted $C_1$-$C_4$alkyl, substituted or unsubstituted $C_1$-$C_4$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted monocyclic carbocycle, substituted or unsubstituted monocyclic heterocycle, —CN, —$OR^{15}$, —$CO_2R^{15}$, —C(=O)N($R^{15}$)$_2$, —C(=O)N($R^{15}$)$OR^{15}$, —N($R^{15}$)$_2$, —$NR^{15}$C(=O)$R^{15}$, or —C($R^{15}$)=N—$OR^{15}$;
$R^7$ is —CN;
each $R^8$ and $R^9$ is independently hydrogen, halogen, substituted or unsubstituted $C_1$-$C_4$alkyl, substituted or unsubstituted $C_1$-$C_4$fluoroalkyl, substituted or unsubstituted $C_1$-$C_6$heteroalkyl, —CN, —OH, or substituted or unsubstituted $C_1$-$C_4$alkoxy;
$X^1$ is N or C—$R^{10}$;
$R^{10}$ is hydrogen, F, Cl, Br, —CN, —N($R^{15}$)$_2$, substituted or unsubstituted $C_1$-$C_4$alkyl, substituted or unsubstituted $C_1$-$C_4$alkoxy, substituted or unsubstituted $C_1$-$C_4$fluoroalkyl, substituted or unsubstituted $C_1$-$C_4$fluoroalkoxy, substituted or unsubstituted $C_1$-$C_4$heteroalkyl, or substituted or unsubstituted $C_3$-$C_6$cycloalkyl;
$R^{12}$ is hydrogen, or substituted or unsubstituted $C_1$-$C_6$alkyl;
$R^{13}$ is hydrogen, —N($R^{16}$)$_2$, —CN, —$CO_2R^{14}$, —C(=O)N($R^{15}$)$_2$, —$OR^{16}$, substituted or unsubstituted $C_1$-$C_6$alkyl, substituted or unsubstituted $C_1$-$C_6$fluoroalkyl, or substituted or unsubstituted $C_1$-$C_6$heteroalkyl;
or $R^{12}$ and $R^{13}$ are taken together with the intervening atoms to which they are attached to form a substituted or unsubstituted N-containing heterocyclic ring;
or $R^{12}$ and $R^{16}$ are taken together with the intervening atoms to which they are attached to form a substituted or unsubstituted N-containing heterocyclic ring;
each $R^{14}$ is independently selected from substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;
each $R^{15}$ is independently selected from hydrogen, substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;
or two $R^{15}$ on the same N atom are taken together with the N atom to which they are attached to form a substituted or unsubstituted N-containing heterocycle; and
$R^{16}$ is independently selected from hydrogen, substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;
or two $R^{16}$ on the same N atom are taken together with the N atom to which they are attached to form a substituted or unsubstituted N-containing heterocycle.

For any and all of the embodiments, substituents are selected from among a subset of the listed alternatives. For example, in some embodiments X is C—$R^1$ or N. In other embodiments, X is C—$R^1$. In some embodiments, X is N.

In some embodiments, $R^{12}$ is hydrogen or substituted or unsubstituted $C_1$-$C_6$alkyl. In some embodiments, $R^{12}$ is hydrogen. In some embodiments, $R^{12}$ is substituted or unsubstituted $C_1$-$C_6$alkyl.

In some embodiments, the compound of Formula (I) has the structure of Formula (Ia), or a pharmaceutically acceptable salt, pharmaceutically acceptable solvate, diastereomeric mixture, or individual enantiomer thereof:

Formula (Ia)

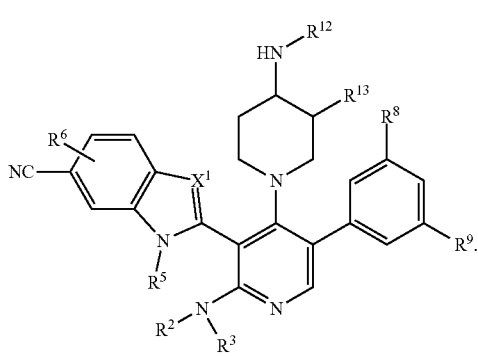

In some embodiments, the compound of Formula (I) has the structure of Formula (Ia-1), or a pharmaceutically acceptable salt, pharmaceutically acceptable solvate, diastereomeric mixture, or individual enantiomer thereof:

Formula (Ia-1)

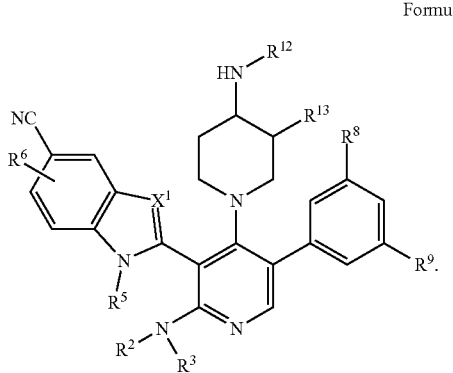

In some embodiments, the compound of Formula (I) has the structure of Formula (Ib), or a pharmaceutically acceptable salt, pharmaceutically acceptable solvate, diastereomeric mixture, or individual enantiomer thereof:

Formula (Ib)

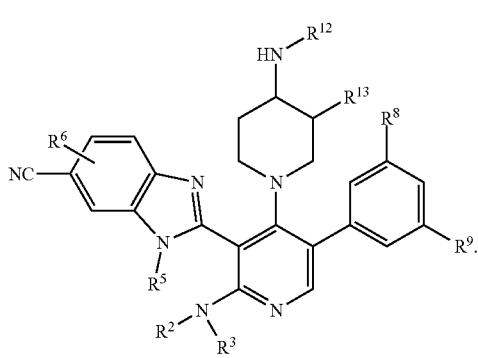

In some embodiments, the compound of Formula (I) has the structure of Formula (Ib-1), or a pharmaceutically acceptable salt, pharmaceutically acceptable solvate, diastereomeric mixture, or individual enantiomer thereof:

Formula (Ib-1)

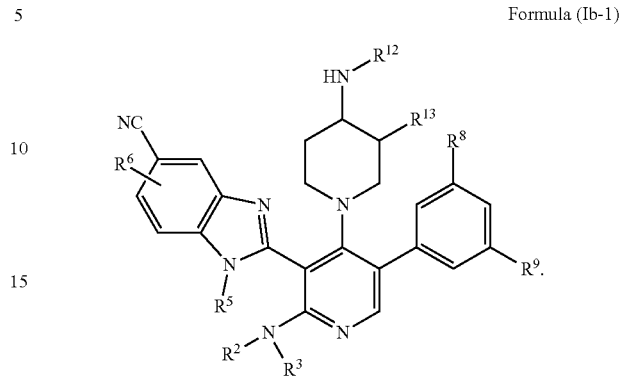

In some embodiments, $R^2$ is hydrogen, $C_1$-$C_4$alkyl, $C_1$-$C_4$fluoroalkyl, or $C_3$-$C_6$cycloalkyl; $R^3$ is hydrogen, $C_1$-$C_4$alkyl, $C_1$-$C_4$fluoroalkyl, or $C_3$-$C_6$cycloalkyl; or $R^2$ and $R^3$ are taken together with the N atom to which they are attached to form a substituted or unsubstituted 5-membered or substituted or unsubstituted 6-membered N-containing heterocyclic ring. In some embodiments, $R^2$ is hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)$ ($CH_2CH_3$), —$C(CH_3)_3$, —$CH_2CH_2OH$, or —$CH_2CH_2OCH_3$; $R^3$ is hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2CH_2OH$, —$CH_2CH_2OCH_3$, or —$CH_2CF_3$; or $R^2$ and $R^3$ are taken together with the N atom to which they are attached to form a substituted or unsubstituted azetidinyl, substituted or unsubstituted pyrrolidinyl, substituted or unsubstituted piperidinyl, substituted or unsubstituted morpholinyl, substituted or unsubstituted thiomorpholinyl, or substituted or unsubstituted piperazinyl. In some embodiments, $R^2$ is hydrogen, —$CH_3$, —$CH_2CH_3$, —$CH_2CH_2CH_3$, —$CH(CH_3)_2$, —$CH_2F$, —$CHF_2$, —$CF_3$, —$CH_2CH_2OH$, —$CH_2CH_2OCH_3$, or —$CH_2CH_2OCF_3$; $R^3$ is hydrogen, —$CH_3$, —$CH_2CH_3$, —$CH_2CH_2CH_3$, —$CH(CH_3)_2$, —$CH_2F$, —$CHF_2$, —$CF_3$, —$CH_2CF_3$, —$CH_2CH_2OH$, —$CH_2CH_2OCH_3$, or —$CH_2CH_2OCF_3$; or $R^2$ and $R^3$ are taken together with the N atom to which they are attached to form substituted or unsubstituted pyrrolidinyl, substituted or unsubstituted piperidinyl, substituted or unsubstituted morpholinyl, substituted or unsubstituted thiomorpholinyl, or substituted or unsubstituted piperazinyl. In some embodiments, $R^2$ is hydrogen, —$CH_3$, —$CH_2CH_3$, —$CH_2CH_2CH_3$, —$CH_2CH_2OH$, —$CH_2CH_2OCH_3$, or —$CH_2CH_2OCF_3$; $R^3$ is hydrogen, —$CH_3$, —$CH_2CH_3$, —$CH_2CH_2CH_3$, —$CH_2CF_3$, —$CH_2CH_2OH$, —$CH_2CH_2OCH_3$, or —$CH_2CH_2OCF_3$; or $R^2$ and $R^3$ are taken together with the N atom to which they are attached to form substituted or unsubstituted pyrrolidinyl, substituted or unsubstituted piperidinyl, substituted or unsubstituted morpholinyl, or substituted or unsubstituted piperazinyl. In some embodiments, $R^2$ is hydrogen, —$CH_3$, —$CH_2CH_2OH$, —$CH_2CH_2OCH_3$, or —$CH_2CH_2OCF_3$; $R^3$ is hydrogen, —$CH_3$, —$CH_2CF_3$, —$CH_2CH_2OH$, —$CH_2CH_2OCH_3$, or —$CH_2CH_2OCF_3$; or $R^2$ and $R^3$ are taken together with the N atom to which they are attached to form substituted or unsubstituted pyrrolidinyl, substituted or unsubstituted piperidinyl or substituted or unsubstituted morpholinyl. In some embodiments, $R^2$ is hydrogen or —$CH_3$; and $R^3$ is hydrogen or —$CH_3$.

In some embodiments, $R^5$ is hydrogen, substituted or unsubstituted $C_1$-$C_4$alkyl, substituted or unsubstituted $C_1$-$C_4$fluoroalkyl, or substituted or unsubstituted $C_3$-$C_6$cycloalkyl. In some embodiments, $R^5$ is hydrogen or substituted or unsubstituted $C_1$-$C_4$alkyl. In some embodiments, $R^5$ is hydrogen, —$CH_3$, —$CH_2CH_3$, or —$CH_2CH_2CH_3$. In some embodiments, $R^5$ is hydrogen.

In some embodiments, $R^6$ is substituted or unsubstituted $C_1$-$C_4$alkyl, substituted or unsubstituted $C_1$-$C_4$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted monocyclic carbocycle, substituted or unsubstituted monocyclic heterocycle, —CN, —$OR^{15}$, —$CO_2R^{15}$, —C(=O)N($R^{15}$)$_2$, —C(=O)N($R^{15}$)$OR^{15}$, —N($R^{15}$)$_2$, or —$NR^{15}$C(=O)$R^{15}$. In some embodiments, $R^6$ is substituted or unsubstituted $C_1$-$C_4$alkyl, substituted or unsubstituted $C_1$-$C_4$fluoroalkyl, substituted or unsubstituted $C_2$-$C_4$alkenyl, substituted or unsubstituted $C_2$-$C_4$alkynyl, —CN, or —$OR^{15}$. In some embodiments, $R^6$ is —$CH_3$, —$CF_3$, —CH=$CH_2$, —C≡CH, —CN, —OH, —$OCH_3$, or —$OCF_3$. In some embodiments, $R^6$ is —$CH_3$, —$CF_3$, —CN, —$OCH_3$, or —$OCF_3$. In some embodiments, $R^6$ is —$CH_3$, —CN, —$OCH_3$, or —$OCF_3$. In some embodiments, $R^6$ is —$OCH_3$.

In some embodiments, each $R^8$ and $R^9$ is independently hydrogen, halogen, $C_1$-$C_4$alkyl, $C_1$-$C_4$fluoroalkyl, or $C_1$-$C_4$alkoxy. In some embodiments, each $R^8$ and $R^9$ is independently hydrogen, F, Cl, Br, —$CH_3$, —$CH_2CH_3$, —$CH_2CH_2CH_3$, —CH($CH_3$)$_2$, —$CH_2CH_2CH_2CH_3$, —$CH_2$CH($CH_3$)$_2$, —CH($CH_3$)($CH_2CH_3$), —C($CH_3$)$_3$, —$CH_2$F, —$CHF_2$, —$CH_2CF_3$, —$OCH_3$, or —$OCH_2CH_3$. In some embodiments, each $R^8$ and $R^9$ is independently hydrogen, F, Cl, Br, —$CH_3$, —$CH_2$F, —$CHF_2$, —$CH_2CF_3$, or —$OCH_3$. In some embodiments, each $R^8$ and $R^9$ is independently F, Cl, Br, —$CH_3$, —$CH_2CH_3$, or —$OCH_3$. In some embodiments, each $R^8$ and $R^9$ is independently F, Cl, —$CH_3$, or —$OCH_3$.

In some embodiments, $R^{12}$ is hydrogen, —$CH_3$, —$CH_2CH_3$, —$CH_2CH_2CH_3$, or —CH($CH_3$)$_2$; $R^{13}$ is hydrogen, —N($R^{16}$)$_2$, —CN, —$CO_2R^{14}$, —C(=O)N($R^{15}$)$_2$, —$OR^{16}$, or substituted or unsubstituted $C_1$-$C_6$heteroalkyl; or $R^{12}$ and $R^{13}$ are taken together with the intervening atoms to which they are attached to form a substituted or unsubstituted N-containing heterocyclic ring; or $R^{12}$ and $R^{16}$ are taken together with the intervening atoms to which they are attached to form a substituted or unsubstituted N-containing heterocyclic ring; and each $R^{16}$ is independently selected from hydrogen, substituted or unsubstituted $C_1$-$C_6$alkyl. In some embodiments, $R^{12}$ is hydrogen, —$CH_3$, or —$CH_2CH_3$; $R^{13}$ is hydrogen, —N($R^{16}$)$_2$, —CN, —$CO_2R^{14}$, —C(=O)N($R^{15}$)$_2$, —$OR^{16}$, or substituted or unsubstituted $C_1$-$C_6$heteroalkyl; or $R^{12}$ and $R^{13}$ are taken together with the intervening atoms to which they are attached to form a substituted or unsubstituted N-containing 6-membered heterocyclic ring; or $R^{12}$ and $R^{16}$ are taken together with the intervening atoms to which they are attached to form a substituted or unsubstituted morpholinyl; and each $R^{16}$ is independently selected from hydrogen, substituted or unsubstituted $C_1$-$C_6$alkyl. In some embodiments, $R^{12}$ is hydrogen, —$CH_3$, or —$CH_2CH_3$; $R^{13}$ is hydrogen, —$OCH_3$, —$OCH_2CH_3$, or —$OCF_3$; or $R^{12}$ and $R^{13}$ are taken together with the intervening atoms to which they are attached to form a substituted or unsubstituted N-containing 6-membered heterocyclic ring; or $R^{12}$ and $R^{16}$ are taken together with the intervening atoms to which they are attached to form a substituted or unsubstituted morpholinyl. In some embodiments, $R^{12}$ is hydrogen; and $R^{13}$ is hydrogen.

In some embodiments, the compound of Formula (I), has the structure of Formula (Ic), or a pharmaceutically acceptable salt, pharmaceutically acceptable solvate, diastereomeric mixture, or individual enantiomer thereof:

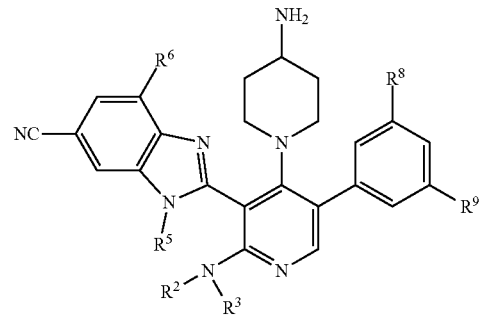

Formula (Ic)

wherein:
$R^2$ is hydrogen or substituted or unsubstituted $C_1$-$C_4$alkyl;
$R^3$ is hydrogen or substituted or unsubstituted $C_1$-$C_4$alkyl;
or $R^2$ and $R^3$ are taken together with the N atom to which they are attached to form a substituted or unsubstituted 5-membered or substituted or unsubstituted 6-membered N-containing heterocyclic ring;
$R^5$ is hydrogen or substituted or unsubstituted $C_1$-$C_4$alkyl;
$R^6$ is substituted or unsubstituted $C_1$-$C_4$alkyl, substituted or unsubstituted $C_1$-$C_4$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted monocyclic carbocycle, substituted or unsubstituted monocyclic heterocycle, —CN, —$OR^{15}$, —$CO_2R^{15}$, —C(=O)N($R^{15}$)$_2$, —C(=O)N($R^{15}$)$OR^{15}$, —N($R^{15}$)$_2$, —$NR^{15}$C(=O)$R^{15}$, or —C($R^{15}$)=N—$OR^{15}$;
each $R^8$ and $R^9$ is independently hydrogen, halogen, substituted or unsubstituted $C_1$-$C_4$alkyl, substituted or unsubstituted $C_1$-$C_4$fluoroalkyl, substituted or unsubstituted $C_1$-$C_6$heteroalkyl, —CN, —OH, or substituted or unsubstituted $C_1$-$C_4$alkoxy;
each $R^{15}$ is independently selected from hydrogen, substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;
or two $R^{15}$ on the same N atom are taken together with the N atom to which they are attached to form a substituted or unsubstituted N-containing heterocycle.

In some embodiments, $R^2$ is hydrogen, —$CH_3$, —$CH_2CH_3$, —$CH_2CH_2CH_3$, —CH($CH_3$)$_2$, —$CH_2$F, —$CHF_2$, —$CF_3$, —$CH_2CH_2$OH, —$CH_2CH_2OCH_3$, or —$CH_2CH_2OCF_3$; $R^3$ is hydrogen, —$CH_3$, —$CH_2CH_3$, —$CH_2CH_2CH_3$, —CH($CH_3$)$_2$, —$CH_2$F, —$CHF_2$, —$CF_3$, —$CH_2CF_3$, —$CH_2CH_2$OH, —$CH_2CH_2OCH_3$, or —$CH_2CH_2OCF_3$; or $R^2$ and $R^3$ are taken together with the N atom to which they are attached to form substituted or unsubstituted pyrrolidinyl, substituted or unsubstituted piperidinyl, substituted or unsubstituted morpholinyl, substituted or unsubstituted thiomorpholinyl, or substituted or unsubstituted piperazinyl; and $R^5$ is hydrogen, —$CH_3$, —CH$_2$CH$_3$, or —CH$_2$CH$_2$CH$_3$. In some embodiments, R$^2$ is hydrogen, —CH$_3$, —CH$_2$CH$_3$, —CH$_2$CH$_2$CH$_3$, or —CH(CH$_3$)$_2$; R$^3$ is hydrogen, —CH$_3$, —CH$_2$CH$_3$, —CH$_2$CH$_2$CH$_3$, or —CH(CH$_3$)$_2$; or R$^2$ and R$^3$ are taken together with the N atom to which they are attached to form substituted or unsubstituted pyrrolidinyl, substituted or unsubstituted piperidinyl, substituted or unsubstituted morpholinyl, substituted or unsubstituted thiomorpholinyl, or substituted or unsubstituted piperazinyl; and R$^5$ is hydrogen, —CH$_3$, —CH$_2$CH$_3$, or —CH$_2$CH$_2$CH$_3$. In some embodiments, R$^2$ is hydrogen or —CH$_3$; R$^3$ is hydrogen or —CH$_3$; and R$^5$ is hydrogen.

In some embodiments, R$^6$ is substituted or unsubstituted C$_1$-C$_4$alkyl, substituted or unsubstituted C$_1$-C$_4$fluoroalkyl, substituted or unsubstituted C$_2$-C$_4$alkenyl, substituted or unsubstituted C$_2$-C$_4$alkynyl, —CN, or —OR$^{15}$; and each R$^8$ and R$^9$ is independently hydrogen, halogen, C$_1$-C$_4$alkyl, C$_1$-C$_4$fluoroalkyl, or C$_1$-C$_4$alkoxy. In some embodiments, R$^6$ is —CH$_3$, —CF$_3$, —CH=CH$_2$, —C≡CH, —CN, —OH, —OCH$_3$, or —OCF$_3$; and each R$^8$ and R$^9$ is independently hydrogen, F, Cl, Br, —CH$_3$, —CH$_2$F, —CHF$_2$, —CH$_2$CF$_3$, or OCH$_3$. In some embodiments, R$^6$ is —CH$_3$, —CF$_3$, —CN, —OCH$_3$, or —OCF$_3$; and each R$^8$ and R$^9$ is independently F, Cl, Br, —CH$_3$, —CH$_2$CH$_3$, or —OCH$_3$. In some embodiments, R$^6$ is —CH$_3$, —CN, —OCH$_3$, or —OCF$_3$; and each R$^8$ and R$^9$ is independently F, Cl, —CH$_3$, or —OCH$_3$.

In some embodiments, the compound of Formula (I) has the structure of Formula (Ic-1), or a pharmaceutically acceptable salt, pharmaceutically acceptable solvate, diastereomeric mixture, or individual enantiomer thereof:

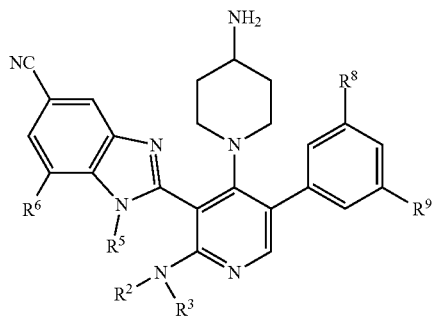

Formula (Ic-1)

wherein the variables are as defined for formula (Ic).

In some embodiments, the compound of Formula (I) has the following structure, or a pharmaceutically acceptable salt, pharmaceutically acceptable solvate, diastereomeric mixture, or individual enantiomer thereof:

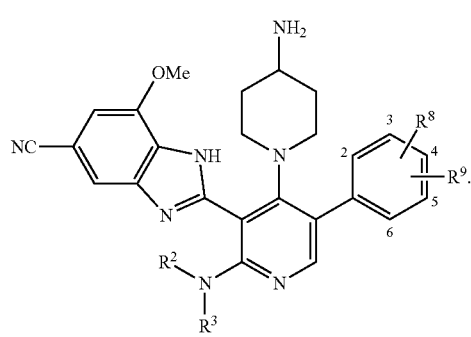

In some embodiments, R$^2$, R$^3$, R$^8$, and R$^9$ are as described in Table 1.

Any combination of the groups described above for the various variables is contemplated herein. Throughout the specification, groups and substituents thereof are chosen by one skilled in the field to provide stable moieties and compounds.

In some embodiments, the compound of Formula (I) could have the structure of Formula (Id) or (Ie). Formula (Id) and Formula (Ie) are tautomers. Formula (Id) and Formula (Ie) should be considered as identical structures even their names could be different:

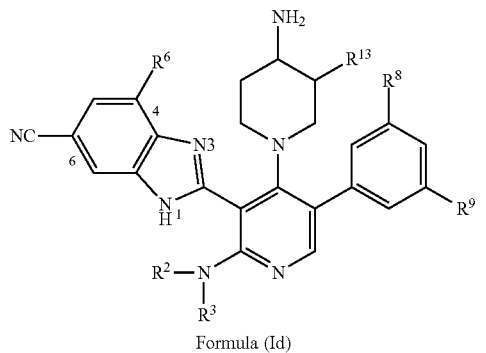

Formula (Id)

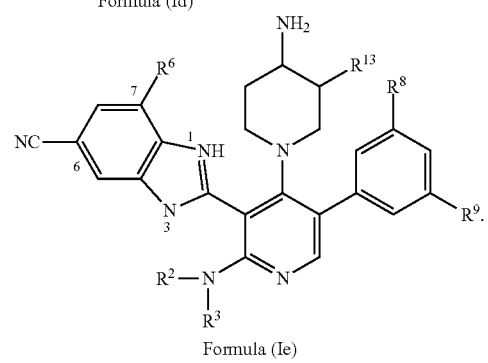

Formula (Ie)

Likewise, Formula (Ia) and Formula (Ia-1) are tautomers, Formula (Ib) and Formula (Ib-1) are tautomers, and Formula (Ic) and Formula (Ic-1) are tautomers.

Exemplary compounds described herein include the compounds described in the following Table 1.

TABLE 1

| Cpd No. | R$^2$ | R$^3$ | R$^8$ | R$^9$ |
|---|---|---|---|---|
| 1-1 | H | H | 3-F | 5-CH$_3$ |
| 1-2 | H | H | 3-F | 5-Cl |
| 1-3 | CH$_3$ | CH$_3$ | 3-F | 5-CH$_3$ |

Compounds in Table 1 are named:

1-1: 2-[2-amino-4-(4-aminopiperidin-1-yl)-5-(3-fluoro-5-methylphenyl)pyridin-3-yl]-4-methoxy-1H-1,3-benzodiazole-6-carbonitrile;

1-2: 2-[2-amino-4-(4-aminopiperidin-1-yl)-5-(3-chloro-5-fluorophenyl)pyridin-3-yl]-4-methoxy-1H-1,3-benzodiazole-6-carbonitrile; and 1-3: 2-[4-(4-aminopiperidin-1-yl)-2-(dimethylamino)-5-(3-fluoro-5-methylphenyl)pyridin-3-yl]-4-methoxy-1H-1,3-benzodiazole-6-carbonitrile.

In some embodiments, provided herein is a pharmaceutically acceptable salt of a compound that is described in Table 1.

In another aspect, provided herein is a compound of Formula (II), or a pharmaceutically acceptable salt, pharmaceutically acceptable solvate, diastereomeric mixture, or individual enantiomer thereof:

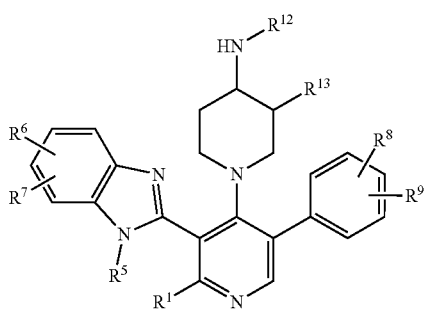

Formula (II)

wherein:

$R^1$ is —CN, —$CO_2R^{15}$, —C(=O)N($R^{15}$)$_2$, —S(=O)$_2R^{15}$, or —S(=O)$_2$N($R^{15}$)$_2$;

$R^5$ is hydrogen, substituted or unsubstituted $C_1$-$C_4$alkyl, substituted or unsubstituted $C_1$-$C_4$fluoroalkyl, substituted or unsubstituted $C_2$-$C_4$alkenyl, or substituted or unsubstituted $C_3$-$C_6$cycloalkyl;

each $R^6$ and $R^7$ is independently halogen, substituted or unsubstituted $C_1$-$C_4$alkyl, substituted or unsubstituted $C_1$-$C_4$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted monocyclic carbocycle, substituted or unsubstituted monocyclic heterocycle, —CN, —$OR^{15}$, —$CO_2R^{15}$, —C(=O)N($R^{15}$)$_2$, —C(=O)N($R^{15}$)$OR^{15}$, —N($R^{15}$)$_2$, —$NR^{15}$C(=O)$R^{15}$, or —C($R^{15}$)=N—$OR^{15}$;

each $R^8$ and $R^9$ is independently hydrogen, halogen, substituted or unsubstituted $C_1$-$C_4$alkyl, substituted or unsubstituted $C_1$-$C_4$fluoroalkyl, substituted or unsubstituted $C_1$-$C_6$heteroalkyl, —CN, —OH, or substituted or unsubstituted $C_1$-$C_4$alkoxy;

$X^1$ is N or C—$R^{10}$;

$R^{10}$ is hydrogen, F, Cl, Br, —CN, —N($R^{15}$)$_2$, substituted or unsubstituted $C_1$-$C_4$alkyl, substituted or unsubstituted $C_1$-$C_4$alkoxy, substituted or unsubstituted $C_1$-$C_4$fluoroalkyl, substituted or unsubstituted $C_1$-$C_4$fluoroalkoxy, substituted or unsubstituted $C_1$-$C_4$heteroalkyl, or substituted or unsubstituted $C_3$-$C_6$cycloalkyl;

$R^{12}$ is hydrogen, or substituted or unsubstituted $C_1$-$C_6$alkyl;

$R^{13}$ is hydrogen, —N($R^{16}$)$_2$, —CN, —$CO_2R^{14}$, —C(=O)N($R^{15}$)$_2$, —$OR^{16}$, substituted or unsubstituted $C_1$-$C_6$alkyl, substituted or unsubstituted $C_1$-$C_6$fluoroalkyl, or substituted or unsubstituted $C_1$-$C_6$heteroalkyl;

or $R^{12}$ and $R^{13}$ are taken together with the intervening atoms to which they are attached to form a substituted or unsubstituted N-containing heterocyclic ring;

or $R^{12}$ and $R^{16}$ are taken together with the intervening atoms to which they are attached to form a substituted or unsubstituted N-containing heterocyclic ring;

each $R^{14}$ is independently selected from substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;

each $R^{15}$ is independently selected from hydrogen, substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;

or two $R^{15}$ on the same N atom are taken together with the N atom to which they are attached to form a substituted or unsubstituted N-containing heterocycle;

each $R^{16}$ is independently selected from hydrogen, substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;

or two $R^{16}$ on the same N atom are taken together with the N atom to which they are attached to form a substituted or unsubstituted N-containing heterocycle.

In some embodiments, the compound of Formula (II) has the structure of Formula (IIa), or a pharmaceutically acceptable salt, pharmaceutically acceptable solvate, diastereomeric mixture, or individual enantiomer thereof:

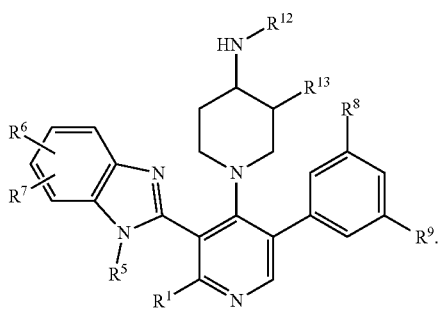

Formula (IIa)

In some embodiments, the compound of Formula (II) has the structure of Formula (IIb), or a pharmaceutically acceptable salt, pharmaceutically acceptable solvate, diastereomeric mixture, or individual enantiomer thereof:

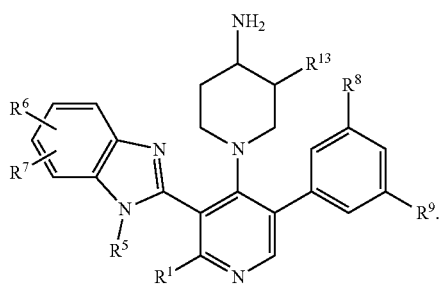

Formula (IIb)

In some embodiments, $R^1$ is —CN, —$CO_2R^{15}$, or —C(=O)N($R^{15}$)$_2$. In some embodiments, each $R^{15}$ is independently hydrogen or $C_1$-$C_4$alkyl.

In some embodiments, $R^5$ is hydrogen, substituted or unsubstituted $C_1$-$C_4$alkyl, substituted or unsubstituted $C_1$-$C_4$fluoroalkyl, or substituted or unsubstituted $C_3$-$C_6$cycloalkyl. In some embodiments, $R^5$ is hydrogen or substituted or unsubstituted $C_1$-$C_4$alkyl. In some embodiments, $R^5$ is hydrogen, —$CH_3$, —$CH_2CH_3$, or —$CH_2CH_2CH_3$. In some embodiments, $R^5$ is hydrogen.

In some embodiments, $R^6$ is halogen, substituted or unsubstituted $C_1$-$C_4$alkyl, substituted or unsubstituted $C_1$-$C_4$fluoroalkyl, substituted or unsubstituted $C_2$-$C_4$alkenyl, substituted or unsubstituted $C_2$-$C_4$alkynyl substituted or unsubstituted $C_1$-$C_6$heteroalkyl, substituted or unsubstituted monocyclic $C_2$-$C_6$heterocycloalkyl, substituted or unsubstituted monocyclic $C_1$-$C_5$heteroaryl, —CN, —$OR^{15}$, —$CO_2R^{15}$, —C(=O)N($R^{15}$)$_2$, —C(=O)N($R^{15}$)$OR^{15}$, —N($R^{15}$)$_2$, —$NR^{15}$C(=O)$R^{15}$, or —C($R^{15}$)=N—$OR^{15}$; and $R^7$ is halogen, substituted or unsubstituted $C_1$-$C_4$alkyl, substituted or unsubstituted $C_1$-$C_4$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, —CN, —OH, or —O-(substituted or unsubstituted $C_1$-$C_4$alkyl). In some embodiments, $R^6$ is F, Cl, Br, —$CH_3$, —$CH_2CH_3$, —$CH_2OH$, —$CH_2CH_2OH$, —$CH_2CN$, —$CH_2CO_2H$, —$CH_2CO_2CH_3$, —$CH_2CO_2CH_2CH_3$, —$CH_2C$(=O)$NH_2$, —$CH_2C$(=O)$NHCH_3$, —$CH_2C$(=O)N($CH_3$)$_2$, —$CH_2NH_2$, —$CH_2NHCH_3$, —$CH_2N$($CH_3$)$_2$, —$CH_2F$, —$CHF_2$, —$CF_3$, —CH=$CH_2$, —C≡CH, cyclopropyloxy, cyclobutyloxy, cyclopentyloxy, oxetanyloxy, tetrahydrofuranyloxy, tetrahydropyranyloxy, azetidinyl, pyrrolidinyl, tetrazolyl, —CN, —OH, —$OCH_3$, —$OCH_2CH_3$, —$OCH_2CH_2OH$, —$OCH_2CN$, —$OCF_3$, —$CO_2H$, —$CO_2CH_3$, —$CO_2CH_2CH_3$, —C(=O)$NH_2$, —C(=O)$NHCH_3$, —C(=O)N($CH_3$)$_2$, —C(=O)$NHOCH_3$, —C(=O)N($CH_3$)$OCH_3$, —$NH_2$, —$NHCH_3$, —N($CH_3$)$_2$, —NHC(=O)$CH_3$, —$NCH_3$C(=O)$CH_3$, —NHC(=O)$OCH_3$, —$NCH_3$C(=O)$OCH_3$, —CH=N—OH, or —CH=N—$OCH_3$; and $R^7$ is F, Cl, Br, —$CH_3$, —$CH_2CH_3$, —$CF_3$, —CH=$CH_2$, —C≡CH, —CN, —OH, —$OCH_3$, —$OCH_2CH_3$, or —$OCF_3$. In some embodiments, each $R^6$ and $R^7$ is independently substituted or unsubstituted $C_1$-$C_4$alkyl, substituted or unsubstituted $C_1$-$C_4$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted monocyclic carbocycle, substituted or unsubstituted monocyclic heterocycle, —CN, —$OR^{15}$, —$CO_2R^{15}$, —C(=O)N($R^{15}$)$_2$, —C(=O)N($R^{15}$)$OR^{15}$, —N($R^{15}$)$_2$, or —$NR^{15}$C(=O)$R^{15}$. In some embodiments, each $R^6$ and $R^7$ is independently substituted or unsubstituted $C_1$-$C_4$alkyl, substituted or unsubstituted $C_1$-$C_4$fluoroalkyl, substituted or unsubstituted $C_2$-$C_4$alkenyl, substituted or unsubstituted $C_2$-$C_4$alkynyl, —CN, or —$OR^{15}$. In some embodiments, each $R^6$ and $R^7$ is independently F, Cl, —$CH_3$, —$CF_3$, —CH=$CH_2$, —C≡CH, —CN, —OH, —$OCH_3$, or —$OCF_3$. In some embodiments, each $R^6$ and $R^7$ is independently F, Cl, —$CH_3$, —$CF_3$, —CN, —$OCH_3$, or —$OCF_3$. In some embodiments, each $R^6$ and $R^7$ is independently F, Cl, —CN, or —$OCH_3$. In some embodiments, each $R^6$ and $R^7$ is independently F, Cl, Br, —$CH_3$, —$CF_3$, —CN, —OH, —$OCH_3$, or —$OCF_3$. In some embodiments, each $R^6$ and $R^7$ is independently F, Cl, —CN or —$OCH_3$.

In some embodiments, each $R^8$ and $R^9$ is independently halogen, $C_1$-$C_4$alkyl, $C_1$-$C_4$fluoroalkyl, or $C_1$-$C_4$alkoxy. In some embodiments, each $R^8$ and $R^9$ is independently F, Cl, Br, —$CH_3$, —$CH_2CH_3$, —$CH_2CH_2CH_3$, —CH($CH_3$)$_2$, —$CH_2CH_2CH_2CH_3$, —$CH_2CH$($CH_3$)$_2$, —CH($CH_3$)($CH_2CH_3$), —C($CH_3$)$_3$, —$CH_2F$, —$CHF_2$, —$CH_2CF_3$, —$OCH_3$, or —$OCH_2CH_3$. In some embodiments, each $R^8$ and $R^9$ is independently hydrogen, F, Cl, Br, —$CH_3$, —$OCH_3$, —$CH_2F$, —$CHF_2$, or —$CH_2CF_3$. In some embodiments, each $R^8$ and $R^9$ is independently F, Cl, Br, —$CH_3$, or —$OCH_3$. In some embodiments, each $R^8$ and $R^9$ is independently F, Cl, —$CH_3$, or —$OCH_3$.

In some embodiments, $R^{12}$ is hydrogen, —$CH_3$, —$CH_2CH_3$, —$CH_2CH_2CH_3$, or —CH($CH_3$)$_2$; $R^{13}$ is hydrogen, —N($R^{16}$)$_2$, —CN, —$CO_2R^{14}$, —C(=O)N($R^{15}$)$_2$, —$OR^{16}$, or substituted or unsubstituted $C_1$-$C_6$heteroalkyl; or $R^{12}$ and $R^{13}$ are taken together with the intervening atoms to which they are attached to form a substituted or unsubstituted N-containing heterocyclic ring; or $R^{12}$ and $R^{16}$ are taken together with the intervening atoms to which they are attached to form a substituted or unsubstituted N-containing heterocyclic ring; each $R^{16}$ is independently selected from hydrogen, substituted or unsubstituted $C_1$-$C_6$alkyl.

In some embodiments, $R^{12}$ is hydrogen, —$CH_3$, or —$CH_2CH_3$; $R^{13}$ is hydrogen, —N($R^{16}$)$_2$, —CN, —$CO_2R^{14}$, —C(=O)N($R^{15}$)$_2$, —$OR^{16}$, or substituted or unsubstituted $C_1$-$C_6$heteroalkyl; or $R^{12}$ and $R^{13}$ are taken together with the intervening atoms to which they are attached to form a substituted or unsubstituted N-containing 6-membered heterocyclic ring; or $R^{12}$ and $R^{16}$ are taken together with the intervening atoms to which they are attached to form a substituted or unsubstituted morpholinyl; and each $R^{16}$ is independently selected from hydrogen, substituted or unsubstituted $C_1$-$C_6$alkyl.

In some embodiments, $R^{12}$ is hydrogen, —$CH_3$, or —$CH_2CH_3$; $R^{13}$ is hydrogen, —$OCH_3$, —$OCH_2CH_3$, or —$OCF_3$; or $R^{12}$ and $R^{13}$ are taken together with the intervening atoms to which they are attached to form a substituted or unsubstituted N-containing 6-membered heterocyclic ring; or $R^{12}$ and $R^{16}$ are taken together with the intervening atoms to which they are attached to form a substituted or unsubstituted morpholinyl.

In some embodiments, $R^{12}$ is hydrogen; and $R^{13}$ is hydrogen

In some embodiments, the compound of Formula (II) has the structure of Formula (IIc), or a pharmaceutically acceptable salt, pharmaceutically acceptable solvate, diastereomeric mixture, or individual enantiomer thereof:

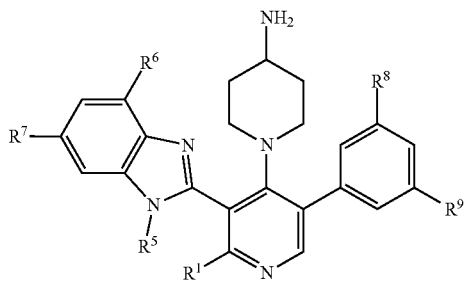

Formula (IIc)

wherein:
R¹ is —CN, —CO₂R¹⁵, or —C(=O)N(R¹⁵)₂;
R⁵ is hydrogen or substituted or unsubstituted C₁-C₄alkyl;
each R⁶ and R⁷ is independently halogen, substituted or unsubstituted C₁-C₄alkyl, substituted or unsubstituted C₁-C₄fluoroalkyl, substituted or unsubstituted C₂-C₄alkenyl, substituted or unsubstituted C₂-C₄alkynyl, substituted or unsubstituted C₁-C₆heteroalkyl, substituted or unsubstituted monocyclic carbocycle, substituted or unsubstituted monocyclic heterocycle, —CN, —OR¹⁵, —CO₂R¹⁵, —C(=O)N(R¹⁵)₂, —C(=O)N(R¹⁵)OR¹⁵, —N(R¹⁵)₂, —NR¹⁵C(=O)R¹⁵, or —C(R¹⁵)=N—OR¹⁵;
each R⁸ and R⁹ is independently hydrogen, halogen, substituted or unsubstituted C₁-C₄alkyl, substituted or unsubstituted C₁-C₄fluoroalkyl, substituted or unsubstituted C₁-C₆heteroalkyl, —CN, —OH, or substituted or unsubstituted C₁-C₄alkoxy;
each R¹⁵ is independently selected from hydrogen, substituted or unsubstituted C₁-C₆alkyl, substituted or unsubstituted C₁-C₆heteroalkyl, substituted or unsubstituted C₃-C₇cycloalkyl, substituted or unsubstituted monocyclic C₂-C₆heterocycloalkyl, substituted or unsubstituted phenyl, and substituted or unsubstituted monocyclic heteroaryl;
or two R¹⁵ on the same N atom are taken together with the N atom to which they are attached to form a substituted or unsubstituted N-containing heterocycle.

In some embodiments, R¹ is —CN, —CO₂CH₃, —CO₂CH₂CH₃, —C(=O)NH₂, —CONHCH₃, or —C(=O)N(CH₃)₂. In some embodiments, R¹ is —CO₂CH₃, —CO₂CH₂CH₃, —C(=O)NH₂, —CONHCH₃, or —C(=O)N(CH₃)₂. In some embodiments, R¹ is —CO₂CH₃, or —CO₂CH₂CH₃. In some embodiments, R¹ is —C(=O)NH₂, —CONHCH₃, or —C(=O)N(CH₃)₂.

In some embodiments, each R⁶ and R⁷ is independently halogen, substituted or unsubstituted C₁-C₄alkyl, substituted or unsubstituted C₁-C₄fluoroalkyl, substituted or unsubstituted C₂-C₄alkenyl, substituted or unsubstituted C₂-C₄alkynyl, —CN, or —OR¹⁵; and each R⁸ and R⁹ is independently hydrogen, halogen, C₁-C₄alkyl, C₁-C₄fluoroalkyl, or C₁-C₄alkoxy. In some embodiments, each R⁶ and R⁷ is independently F, Cl, Br, —CH₃, —CF₃, —CN, —OH, —OCH₃, or —OCF₃. In some embodiments, each R⁶ and R⁷ is independently F, Cl, —CN, or —OCH₃. In some embodiments, each R⁸ and R⁹ is independently hydrogen, halogen, C₁-C₄alkyl, C₁-C₄fluoroalkyl, or C₁-C₄alkoxy. In some embodiments, each R⁸ and R⁹ is independently hydrogen, F, Cl, Br, —CH₃, —CH₂CH₃, —CH₂CH₂CH₃, —CH(CH₃)₂, —CH₂CH₂CH₂CH₃, —CH₂CH(CH₃)₂, —CH(CH₃)(CH₂CH₃), —C(CH₃)₃, —CH₂F, —CHF₂, —CH₂CF₃, —OCH₃, or —OCH₂CH₃. In some embodiments, each R⁸ and R⁹ is independently hydrogen, F, Cl, —CH₃, or —OCH₃.

In some embodiments, the compound of Formula (II) has the structure of Formula (IIc-1), or a pharmaceutically acceptable salt, pharmaceutically acceptable solvate, diastereomeric mixture, or individual enantiomer thereof:

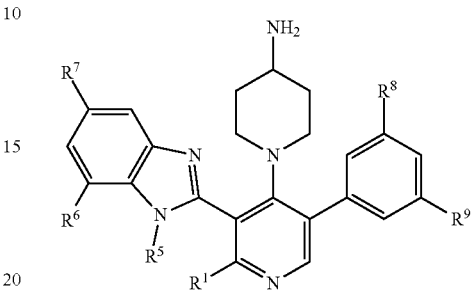

Formula (IIc-1)

wherein the variables are as defined for formula (IIc).

In some embodiments, the compound of Formula (II) has the following structure, or a pharmaceutically acceptable salt, pharmaceutically acceptable solvate, diastereomeric mixture, or individual enantiomer thereof:

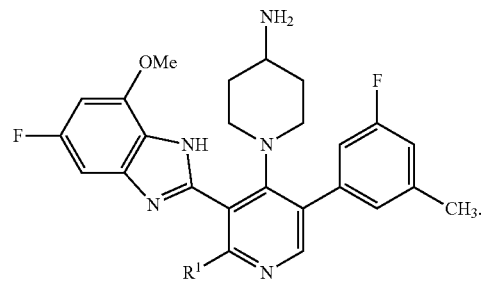

In some embodiments, R¹ is as described in Table 2.

Any combination of the groups described above for the various variables is contemplated herein. Throughout the specification, groups and substituents thereof are chosen by one skilled in the field to provide stable moieties and compounds.

In some embodiments, the compound of Formula (II) could have the structure of Formula (IId) or (IIe). Formula (IId) and Formula (IIe) are tautomers. Formula (IId) and Formula (IIe) should be considered as identical structures even their names could be different:

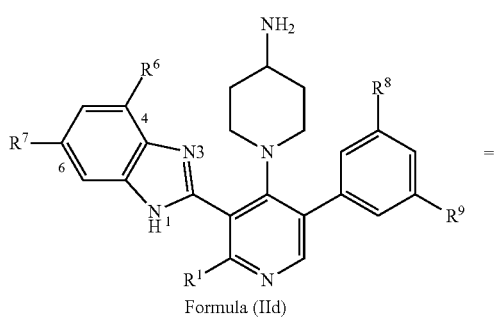

Formula (IId)

-continued

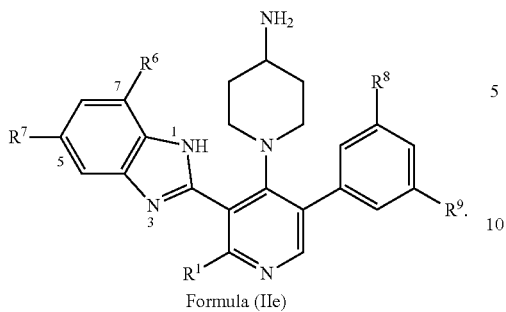

Formula (IIe)

Likewise, Formula (IIc) and Formula (IIc-1) are tautomers.

Exemplary compounds described herein include the compounds described in the following Table 2.

TABLE 2

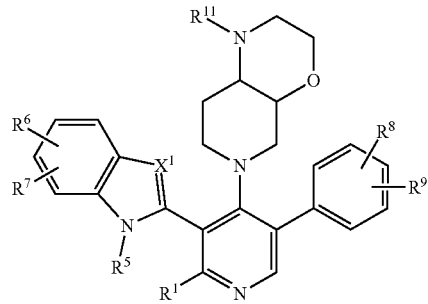

| Cpd No. | $R^1$ |
|---|---|
| 2-1 | —$CO_2CH_3$ |
| 2-2 | —CN |
| 2-3 | —$CONH_2$ |
| 2-4 | —$CONHCH_3$ |

Compounds in Table 2 are named:

2-1: methyl 4-(4-aminopiperidin-1-yl)-3-(6-fluoro-4-methoxy-1H-1,3-benzodiazol-2-yl)-5-(3-fluoro-5-methylphenyl)pyridine-2-carboxylate;

2-2: 4-(4-aminopiperidin-1-yl)-3-(6-fluoro-4-methoxy-1H-1,3-benzodiazol-2-yl)-5-(3-fluoro-5-methylphenyl)pyridine-2-carbonitrile;

2-3: 4-(4-aminopiperidin-1-yl)-3-(6-fluoro-4-methoxy-1H-1,3-benzodiazol-2-yl)-5-(3-fluoro-5-methylphenyl)pyridine-2-carboxamide;

2-4: 4-(4-aminopiperidin-1-yl)-3-(6-fluoro-4-methoxy-1H-1,3-benzodiazol-2-yl)-5-(3-fluoro-5-methylphenyl)-N-methylpyridine-2-carboxamide.

In some embodiments, provided herein is a pharmaceutically acceptable salt of a compound that is described in Table 2.

In another aspect, described herein is a compound of Formula (III), or a pharmaceutically acceptable salt, pharmaceutically acceptable solvate, diastereomeric mixture, or individual enantiomer thereof:

Formula (III)

wherein:

$R^1$ is —$NR^2R^3$, —$OR^2$, or $R^4$;

$R^2$ is hydrogen, substituted or unsubstituted $C_1$-$C_4$alkyl, substituted or unsubstituted $C_1$-$C_4$fluoroalkyl, substituted or unsubstituted $C_1$-$C_4$heteroalkyl, or substituted or unsubstituted $C_3$-$C_6$cycloalkyl;

$R^3$ is hydrogen, substituted or unsubstituted $C_1$-$C_4$alkyl, substituted or unsubstituted $C_1$-$C_4$fluoroalkyl, substituted or unsubstituted $C_1$-$C_4$heteroalkyl, or substituted or unsubstituted $C_3$-$C_6$cycloalkyl;

or $R^2$ and $R^3$ are taken together with the N atom to which they are attached to form a substituted or unsubstituted 4-membered, substituted or unsubstituted 5-membered or substituted or unsubstituted 6-membered N-containing heterocyclic ring;

$R^4$ is F, Cl, Br, —CN, substituted or unsubstituted $C_1$-$C_4$alkyl, substituted or unsubstituted $C_1$-$C_4$fluoroalkyl, substituted or unsubstituted $C_1$-$C_4$alkoxy, —$SC_1$-$C_4$alkyl, —$S(=O)C_1$-$C_4$alkyl, —$S(=O)_2$—$C_1$-$C_4$alkyl, substituted or unsubstituted $C_1$-$C_4$heteroalkyl, substituted or unsubstituted $C_3$-$C_6$cycloalkyl, —$CO_2R^{15}$, —$C(=O)N(R^{15})_2$;

$R^5$ is hydrogen, substituted or unsubstituted $C_1$-$C_4$alkyl, substituted or unsubstituted $C_1$-$C_4$fluoroalkyl, substituted or unsubstituted $C_2$-$C_4$alkenyl, or substituted or unsubstituted $C_3$-$C_6$cycloalkyl;

each $R^6$ and $R^7$ is independently halogen, substituted or unsubstituted $C_1$-$C_4$alkyl, substituted or unsubstituted $C_1$-$C_4$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted monocyclic carbocycle, substituted or unsubstituted monocyclic heterocycle, —CN, —$OR^{15}$, —$CO_2R^{15}$, —$C(=O)N(R^{15})_2$, —$C(=O)N(R^{15})OR^{15}$, —$N(R^{15})_2$, —$NR^{15}C(=O)R^{15}$, or —$C(R^{15})=N$—$OR^{15}$;

each $R^8$ and $R^9$ is independently hydrogen, halogen, substituted or unsubstituted $C_1$-$C_4$alkyl, substituted or unsubstituted $C_1$-$C_4$fluoroalkyl, substituted or unsubstituted $C_1$-$C_6$heteroalkyl, —CN, —OH, or substituted or unsubstituted $C_1$-$C_4$alkoxy;

$X^1$ is N or C—$R^{10}$;

$R^{10}$ is hydrogen, F, Cl, Br, —CN, —$N(R^{15})_2$, substituted or unsubstituted $C_1$-$C_4$alkyl, substituted or unsubstituted $C_1$-$C_4$alkoxy, substituted or unsubstituted $C_1$-$C_4$fluoroalkyl, substituted or unsubstituted $C_1$-$C_4$fluoroalkoxy, substituted or unsubstituted $C_1$-$C_4$heteroalkyl, or substituted or unsubstituted $C_3$-$C_6$cycloalkyl;

$R^{11}$ is hydrogen or substituted or unsubstituted $C_1$-$C_6$alkyl;

each $R^{15}$ is independently selected from hydrogen, substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;

or two $R^{15}$ on the same N atom are taken together with the N atom to which they are attached to form a substituted or unsubstituted N-containing heterocycle.

In some embodiments, $R^1$ is —$NR^2R^3$. In some embodiments, $R^2$ is hydrogen, $C_1$-$C_4$alkyl, $C_1$-$C_4$fluoroalkyl, $C_1$-$C_4$heteroalkyl, or $C_3$-$C_6$cycloalkyl; $R^3$ is hydrogen, $C_1$-$C_4$alkyl, $C_1$-$C_4$fluoroalkyl, $C_1$-$C_4$heteroalkyl, or $C_3$-$C_6$cycloalkyl; or $R^2$ and $R^3$ are taken together with the N atom to which they are attached to form a substituted or unsubstituted 4-membered, substituted or unsubstituted 5-membered or substituted or unsubstituted 6-membered N-containing heterocyclic ring. In some embodiments, $R^2$ is hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2CH_2OH$, —$CH_2CH_2OCH_3$, or —$CH_2CN$; $R^3$ is hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2CH_2OH$, —$CH_2CH_2OCH_3$, —$CH_2CN$, or —$CH_2CF_3$; or $R^2$ and $R^3$ are taken together with the N atom to which they are attached to form a substituted or unsubstituted azetidinyl, substituted or unsubstituted pyrrolidinyl, substituted or unsubstituted piperidinyl, substituted or unsubstituted morpholinyl, substituted or unsubstituted thiomorpholinyl, or substituted or unsubstituted piperazinyl.

In some embodiments, $R^3$ is hydrogen. In some embodiments, $R^2$ is —$CH_3$.

In some embodiments, $R^1$ is —$OR^2$. In some embodiments, $R^2$ is hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2CH_2OH$, —$CH_2CH_2OCH_3$, —$CH_2CN$, —$CH_2F$, —$CHF_2$, —$CF_3$, or —$CH_2CF_3$.

In some embodiments, $R^1$ is $R^4$; and $R^4$ is F, Cl, Br, —CN, $C_1$-$C_4$alkyl, —$SC_1$-$C_4$alkyl, —$S(=O)C_1$-$C_4$alkyl, —$S(=O)_2$—$C_1$-$C_4$alkyl, $C_1$-$C_4$fluoroalkyl, —$CO_2C_1$-$C_4$alkyl, or —$C(=O)N(R^{15})_2$. In some embodiments, $R^4$ is F, Cl, Br, —CN, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2F$, —$CHF_2$, —$CF_3$, or —$CH_2CF_3$;

In some embodiments, $R^1$ is —$NR^2R^3$, —$OR^2$, F, Cl, Br, —CN, $C_1$-$C_4$alkyl, or $C_1$-$C_4$fluoroalkyl.

In some embodiments, $R^5$ is hydrogen or substituted or unsubstituted $C_1$-$C_4$alkyl. In some embodiments, $R^5$ is hydrogen.

In some embodiments, $R^6$ is halogen, substituted or unsubstituted $C_1$-$C_4$alkyl, substituted or unsubstituted $C_1$-$C_4$fluoroalkyl, substituted or unsubstituted $C_2$-$C_4$alkenyl, substituted or unsubstituted $C_2$-$C_4$alkynyl substituted or unsubstituted $C_1$-$C_6$heteroalkyl, substituted or unsubstituted monocyclic $C_2$-$C_6$heterocycloalkyl, substituted or unsubstituted monocyclic $C_1$-$C_5$heteroaryl, —CN, —$OR^{15}$, —$CO_2R^{15}$, —$C(=O)N(R^{15})_2$, —$C(=O)N(R^{15})OR^{15}$, —$N(R^{15})_2$, —$NR^{15}C(=O)R^{15}$, or —$C(R^{15})=N$—$OR^{15}$; and $R^7$ is halogen, substituted or unsubstituted $C_1$-$C_4$alkyl, substituted or unsubstituted $C_1$-$C_4$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, —CN, —OH, or —O-(substituted or unsubstituted $C_1$-$C_4$alkyl). In some embodiments, $R^6$ is F, Cl, Br, —$CH_3$, —$CH_2CH_3$, —$CH_2OH$, —$CH_2CH_2OH$, —$CH_2CN$, —$CH_2CO_2H$, —$CH_2CO_2CH_3$, —$CH_2CO_2CH_2CH_3$, —$CH_2C(=O)NH_2$, —$CH_2C(=O)NHCH_3$, —$CH_2C(=O)N(CH_3)_2$, —$CH_2NH_2$, —$CH_2NHCH_3$, —$CH_2N(CH_3)_2$, —$CH_2F$, —$CHF_2$, —$CF_3$, —$CH=CH_2$, cyclopropyloxy, cyclobutyloxy, cyclopentyloxy, oxetanyloxy, tetrahydrofuranyloxy, tetrahydropyranyloxy, azetidinyl, pyrrolidinyl, tetrazolyl, —CN, —OH, —$OCH_3$, —$OCH_2CH_3$, —$OCH_2CH_2OH$, —$OCH_2CN$, —$OCF_3$, —$CO_2H$, —$CO_2CH_3$, —$CO_2CH_2CH_3$, —$C(=O)NH_2$, —$C(=O)NHCH_3$, —$C(=O)N(CH_3)_2$, —$C(=O)NHOCH_3$, —$C(=O)N(CH_3)OCH_3$, —$NH_2$, —$NHCH_3$, —$N(CH_3)_2$, —$NHC(=O)CH_3$, —$NCH_3C(=O)CH_3$, —$NHC(=O)OCH_3$, —$NCH_3C(=O)OCH_3$, —$CH=N$—OH, or —$CH=N$—$OCH_3$; and $R^7$ is F, Cl, Br, —$CH_3$, —$CH_2CH_3$, —$CF_3$, —$CH=CH_2$, —$C\equiv CH$, —CN, —OH, —$OCH_3$, —$OCH_2CH_3$, or —$OCF_3$. In some embodiments, each $R^6$ and $R^7$ is independently F, Cl, Br, —$CH_3$, —$CF_3$, —CN, —OH, —$OCH_3$, or —$OCF_3$. In some embodiments, each $R^6$ and $R^7$ is independently F, Cl, —CN, or —$OCH_3$.

In some embodiments, each $R^8$ and $R^9$ is independently hydrogen, halogen, $C_1$-$C_4$alkyl, $C_1$-$C_4$fluoroalkyl, or $C_1$-$C_4$alkoxy. In some embodiments, each $R^8$ and $R^9$ is independently hydrogen, F, Cl, Br, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2F$, —$CHF_2$, —$CH_2CF_3$, —$OCH_3$, or —$OCH_2CH_3$. In some embodiments, each $R^8$ and $R^9$ is independently hydrogen, F, Cl, —$CH_3$, or —$OCH_3$.

In some embodiments, $R^{11}$ is hydrogen or $C_1$-$C_4$alkyl. In some embodiments, $R^{11}$ is hydrogen.

In some embodiments, the compound of Formula (III) has the structure of Formula (IIIa), or a pharmaceutically acceptable salt, pharmaceutically acceptable solvate, diastereomeric mixture, or individual enantiomer thereof:

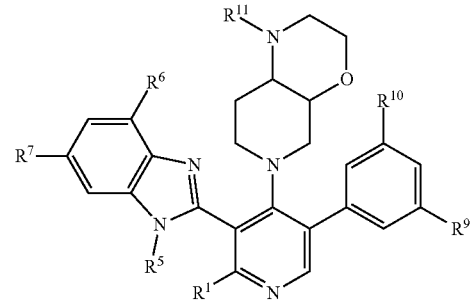

Formula (IIIa)

wherein:

$R^1$ is —$NR^2R^3$, —$OR^2$, F, Cl, Br, —CN, $C_1$-$C_4$alkyl, or $C_1$-$C_4$fluoroalkyl;

$R^2$ is hydrogen or substituted or unsubstituted $C_1$-$C_4$alkyl;

$R^3$ is hydrogen or substituted or unsubstituted $C_1$-$C_4$alkyl;

or $R^2$ and $R^3$ are taken together with the N atom to which they are attached to form a substituted or unsubstituted 5-membered or substituted or unsubstituted 6-membered N-containing heterocyclic ring;

$R^5$ is hydrogen or substituted or unsubstituted $C_1$-$C_4$alkyl;

each $R^6$ and $R^7$ is independently halogen, substituted or unsubstituted $C_1$-$C_4$alkyl, substituted or unsubstituted $C_1$-$C_4$fluoroalkyl, substituted or unsubstituted C$_2$-C$_4$alkenyl, substituted or unsubstituted C$_2$-C$_4$alkynyl, substituted or unsubstituted C$_1$-C$_6$heteroalkyl, substituted or unsubstituted monocyclic carbocycle, substituted or unsubstituted monocyclic heterocycle, —CN, —OR$^{15}$, —CO$_2$R$^{15}$, —C(=O)N(R$^{15}$)$_2$, —C(=O)N(R$^{15}$)OR$^{15}$, —N(R$^{15}$)$_2$, —NR$^{15}$C(=O)R$^{15}$, or —C(R$^{15}$)=N—OR$^{15}$;

each R$^8$ and R$^9$ is independently hydrogen, halogen, substituted or unsubstituted C$_1$-C$_4$alkyl, substituted or unsubstituted C$_1$-C$_4$fluoroalkyl, substituted or unsubstituted C$_1$-C$_6$heteroalkyl, —CN, —OH, or substituted or unsubstituted C$_1$-C$_4$alkoxy;

R$^{11}$ is hydrogen or substituted or unsubstituted C$_1$-C$_4$alkyl;

each R$^{15}$ is independently selected from hydrogen, substituted or unsubstituted C$_1$-C$_6$alkyl, substituted or unsubstituted C$_1$-C$_6$heteroalkyl, substituted or unsubstituted C$_3$-C$_7$cycloalkyl, substituted or unsubstituted monocyclic C$_2$-C$_6$heterocycloalkyl, substituted or unsubstituted phenyl, and substituted or unsubstituted monocyclic heteroaryl;

or two R$^{15}$ on the same N atom are taken together with the N atom to which they are attached to form a substituted or unsubstituted N-containing heterocycle.

In some embodiments, R$^2$ is hydrogen, —CH$_3$, —CH$_2$CH$_3$, —CH$_2$CH$_2$CH$_3$, —CH(CH$_3$)$_2$, —CH$_2$F, —CHF$_2$, —CF$_3$, —CH$_2$CH$_2$OH, —CH$_2$CH$_2$OCH$_3$, or —CH$_2$CH$_2$OCF$_3$; R$^3$ is hydrogen, —CH$_3$, —CH$_2$CH$_3$, —CH$_2$CH$_2$CH$_3$, —CH(CH$_3$)$_2$, —CH$_2$F, —CHF$_2$, —CF$_3$, —CH$_2$CF$_3$, —CH$_2$CH$_2$OH, —CH$_2$CH$_2$OCH$_3$, or —CH$_2$CH$_2$OCF$_3$; or R$^2$ and R$^3$ are taken together with the N atom to which they are attached to form substituted or unsubstituted pyrrolidinyl, substituted or unsubstituted piperidinyl, substituted or unsubstituted morpholinyl, substituted or unsubstituted thiomorpholinyl, or substituted or unsubstituted piperazinyl; and R$^5$ is hydrogen, —CH$_3$, —CH$_2$CH$_3$, or —CH$_2$CH$_2$CH$_3$. In some embodiments, R$^2$ is hydrogen, —CH$_3$, —CH$_2$CH$_3$, —CH$_2$CH$_2$CH$_3$, or —CH(CH$_3$)$_2$; R$^3$ is hydrogen, —CH$_3$, —CH$_2$CH$_3$, —CH$_2$CH$_2$CH$_3$, or —CH(CH$_3$)$_2$; or R$^2$ and R$^3$ are taken together with the N atom to which they are attached to form substituted or unsubstituted pyrrolidinyl, substituted or unsubstituted piperidinyl, substituted or unsubstituted morpholinyl, substituted or unsubstituted thiomorpholinyl, or substituted or unsubstituted piperazinyl; and R$^5$ is hydrogen, —CH$_3$, —CH$_2$CH$_3$, or —CH$_2$CH$_2$CH$_3$. In some embodiments, R$^2$ is hydrogen or —CH$_3$; R$^3$ is hydrogen; and R$^5$ is hydrogen.

In some embodiments, each R$^6$ and R$^7$ is independently halogen, substituted or unsubstituted C$_1$-C$_4$alkyl, substituted or unsubstituted C$_1$-C$_4$fluoroalkyl, substituted or unsubstituted C$_2$-C$_4$alkenyl, substituted or unsubstituted C$_2$-C$_4$alkynyl, —CN, or —OR$^{15}$; and each R$^8$ and R$^9$ is independently hydrogen, halogen, C$_1$-C$_4$alkyl, C$_1$-C$_4$fluoroalkyl, or C$_1$-C$_4$alkoxy. In some embodiments, each R$^6$ and R$^7$ is independently F, Cl, —CH$_3$, —CF$_3$, —CH=CH$_2$, —C≡CH, —CN, —OH, —OCH$_3$, or —OCF$_3$; and each R$^8$ and R$^9$ is independently hydrogen, F, Cl, Br, —CH$_3$, —CH$_2$F, —CHF$_2$, —CH$_2$CF$_3$, or —OCH$_3$. In some embodiments, each R$^6$ and R$^7$ is independently F, Cl, —CH$_3$, —CF$_3$, —CN, —OCH$_3$, or —OCF$_3$; and each R$^8$ and R$^9$ is independently hydrogen, F, Cl, Br, —CH$_3$, or —OCH$_3$. In some embodiments, each R$^6$ and R$^7$ is independently F, Cl, —CH$_3$, —CN, —OCH$_3$, or —OCF$_3$; and each R$^8$ and R$^9$ is independently hydrogen, F, Cl, —CH$_3$, or —OCH$_3$.

In some embodiments, the compound of Formula (III) has the structure of Formula (IIIa-1), or a pharmaceutically acceptable salt, pharmaceutically acceptable solvate, diastereomeric mixture, or individual enantiomer thereof:

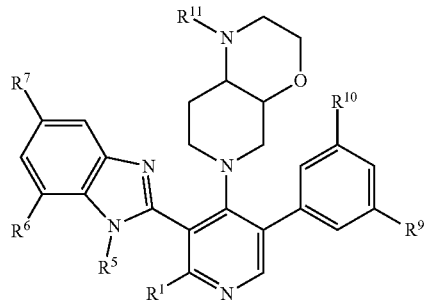

Formula (IIIa-1)

wherein the variables are as defined for formula (Ma).

In some embodiments, the compound of Formula (III) has the following structure, or a pharmaceutically acceptable salt, pharmaceutically acceptable solvate, diastereomeric mixture, or individual enantiomer thereof:

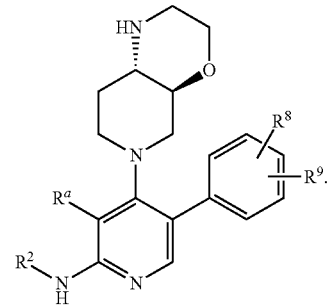

In some embodiments, R$^a$, R$^1$, R$^8$, and R$^9$ are as described in Table 3.

Any combination of the groups described above for the various variables is contemplated herein. Throughout the specification, groups and substituents thereof are chosen by one skilled in the field to provide stable moieties and compounds.

In some embodiments, the compound of Formula (III) could have the structure of Formula (IIIb) or (IIIc). Formula (IIIb) and Formula (IIIc) are tautomers. Formula (IIIb) and Formula (IIIc) should be considered as identical structures even their names could be different:

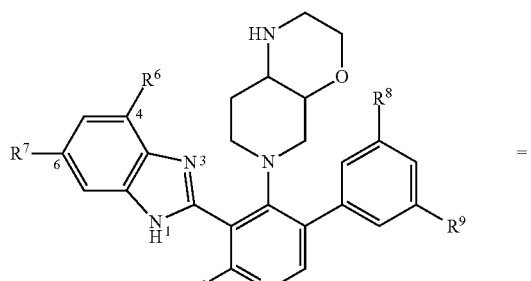

Formula (IIId)

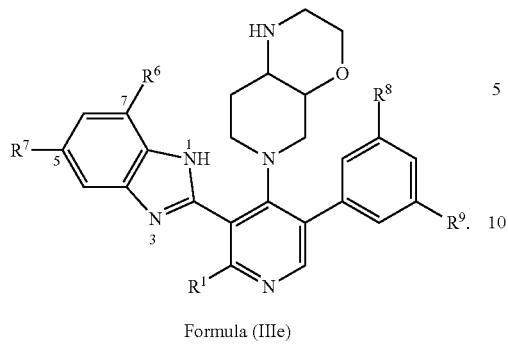

Formula (IIIe)

Likewise, Formula (IIIa) and Formula (IIIa-1) are tautomers.

Exemplary compounds described herein include the compounds described in the following Table 3.

TABLE 3

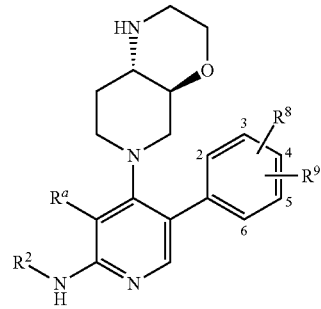

| Cpd No. | Rᵃ | R² | R⁸ | R⁹ |
|---|---|---|---|---|
| 3-1 | 4,6-difluorobenzimidazol-2-yl | —H | 3-F | 5-CH₃ |
| 3-2 | 4,6-difluorobenzimidazol-2-yl | —H | 3-F | 5-F |
| 3-3 | 4,6-difluorobenzimidazol-2-yl | —H | 3-F | 5-H |
| 3-4 | 4,6-difluorobenzimidazol-2-yl | —H | 3-F | 5-OMe |

TABLE 3-continued

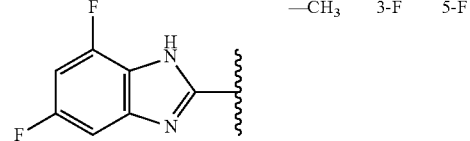

| Cpd No. | Rᵃ | R² | R⁸ | R⁹ |
|---|---|---|---|---|
| 3-5 | 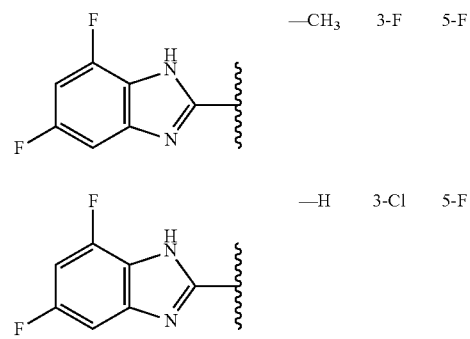 4,6-difluorobenzimidazol-2-yl | —CH₃ | 3-F | 5-OMe |
| 3-6 | 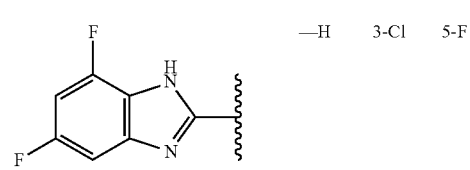 4,6-difluorobenzimidazol-2-yl | —CH₃ | 3-F | 5-F |
| 3-7 | 4,6-difluorobenzimidazol-2-yl | —H | 3-Cl | 5-F |
| 3-8 | 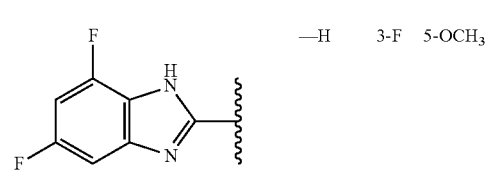 4,6-difluorobenzimidazol-2-yl | —H | 3-F | 5-OCH₃ |
| 3-9 | 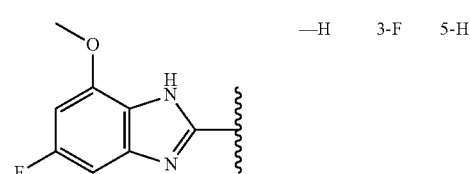 4-methoxy-6-fluorobenzimidazol-2-yl | —H | 3-F | 5-H |
| 3-10 | 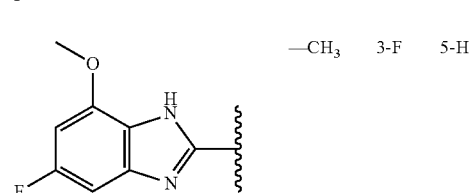 4-methoxy-6-fluorobenzimidazol-2-yl | —CH₃ | 3-F | 5-H |
| 3-11 | 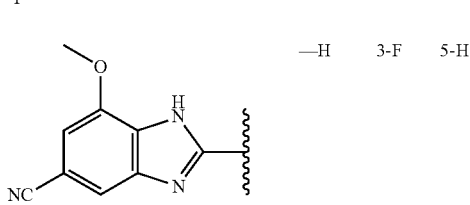 4-methoxy-6-cyanobenzimidazol-2-yl | —H | 3-F | 5-H |

TABLE 3-continued

| Cpd No. | $R^a$ | $R^2$ | $R^8$ | $R^9$ |
|---|---|---|---|---|
| 3-12 | 4-methoxy-6-cyano-benzimidazol-2-yl | —CH₃ | 3-F | 5-H |
| 3-13 | 4-methoxy-6-fluoro-benzimidazol-2-yl | —CH₃ | 3-Cl | 5-F |
| 3-14 | 4-methoxy-6-fluoro-benzimidazol-2-yl | —H | 3-F | 5-CH₃ |
| 3-15 | 4-methoxy-6-fluoro-benzimidazol-2-yl | —CH₃ | 3-F | 5-CH₃ |
| 3-16 | 4-methoxy-6-cyano-benzimidazol-2-yl | —H | 3-F | 5-CH₃ |
| 3-17 | 4-methoxy-6-fluoro-benzimidazol-2-yl | —H | 3-Cl | 5-F |
| 3-18 | 4-methoxy-6-cyano-benzimidazol-2-yl | —H | 3-F | 5-F |
| 3-19 | 4-fluoro-6-cyano-benzimidazol-2-yl | —H | 3-F | 5-F |

Compounds in Table 3 are named:

3-1: 4-[(4αS,8αS)-octahydro-1H-pyrido[3,4-b][1,4]oxazin-6-yl]-3-(4,6-difluoro-1H-1,3-benzodiazol-2-yl)-5-(3-fluoro-5-methylphenyl)pyridin-2-amine;

3-2: 4-[(4αS,8αS)-octahydro-1H-pyrido[3,4-b][1,4]oxazin-6-yl]-3-(4,6-difluoro-1H-1,3-benzodiazol-2-yl)-5-(3,5-difluorophenyl)pyridin-2-amine;

3-3: 4-[(4αS,8αS)-octahydro-1H-pyrido[3,4-b][1,4]oxazin-6-yl]-3-(4,6-difluoro-1H-1,3-benzodiazol-2-yl)-5-(3-fluorophenyl)pyridin-2-amine;

3-4: 4-[(4αS,8αS)-octahydro-1H-pyrido[3,4-b][1,4]oxazin-6-yl]-3-(4,6-difluoro-1H-1,3-benzodiazol-2-yl)-5-(3-fluoro-5-methoxyphenyl)pyridin-2-amine;

3-5: 4-[(4αS,8αS)-octahydro-1H-pyrido[3,4-b][1,4]oxazin-6-yl]-3-(4,6-difluoro-1H-1,3-benzodiazol-2-yl)-5-(3-fluoro-5-methoxyphenyl)-N-methylpyridin-2-amine;

3-6: 4-[(4αS,8αS)-octahydro-1H-pyrido[3,4-b][1,4]oxazin-6-yl]-3-(4,6-difluoro-1H-1,3-benzodiazol-2-yl)-5-(3,5-difluorophenyl)-N-methylpyridin-2-amine;

3-7: 4-[(4αS,8αS)-octahydro-1H-pyrido[3,4-b][1,4]oxazin-6-yl]-5-(3-chloro-5-fluorophenyl)-3-(4,6-difluoro-1H-1,3-benzodiazol-2-yl)pyridin-2-amine;

3-8: 4-[(4αS,8αS)-octahydro-1H-pyrido[3,4-b][1,4]oxazin-6-yl]-3-(4,6-difluoro-1H-1,3-benzodiazol-2-yl)-5-(3-fluoro-5-methoxyphenyl)pyridin-2-amine;

3-9: 4-[(4αS,8αS)-octahydro-1H-pyrido[3,4-b][1,4]oxazin-6-yl]-3-(6-fluoro-4-methoxy-1H-1,3-benzodiazol-2-yl)-5-(3-fluorophenyl)pyridin-2-amine:

3-10: 4-[(4αS,8αS)-octahydro-1H-pyrido[3,4-b][1,4]oxazin-6-yl]-3-(6-fluoro-4-methoxy-1H-1,3-benzodiazol-2-yl)-5-(3-fluorophenyl)-N-methylpyridin-2-amine;

3-11: 2-{4-[(4αS,8αS)-octahydro-1H-pyrido[3,4-b][1,4]oxazin-6-yl]-2-amino-5-(3-fluorophenyl)pyridin-3-yl}-4-methoxy-1H-1,3-benzodiazole-6-carbonitrile;

3-12: 2-[4-[(4αS,8αS)-octahydro-1H-pyrido[3,4-b][1,4]oxazin-6-yl]-5-(3-fluorophenyl)-2-(methylamino)pyridin-3-yl]-4-methoxy-1H-1,3-benzodiazole-6-carbonitrile;

3-13: 4-[(4αS,8αS)-octahydro-1H-pyrido[3,4-b][1,4]oxazin-6-yl]-5-(3-chloro-5-fluorophenyl)-3-(6-fluoro-4-methoxy-1H-1,3-benzodiazol-2-yl)-N-methylpyridin-2-amine;

3-14: 4-[(4αS,8αS)-octahydro-1H-pyrido[3,4-b][1,4]oxazin-6-yl]-3-(6-fluoro-4-methoxy-1H-1,3-benzodiazol-2-yl)-5-(3-fluoro-5-methylphenyl)pyridin-2-amine;
3-15: 4-[(4αS,8αS)-octahydro-1H-pyrido[3,4-b][1,4]oxazin-6-yl]-3-(6-fluoro-4-methoxy-1H-1,3-benzodiazol-2-yl)-5-(3-fluoro-5-methylphenyl)-N-methylpyridin-2-amine;
3-16: 4-[(4αS,8αS)-octahydro-1H-pyrido[3,4-b][1,4]oxazin-6-yl]-3-(6-fluoro-4-methoxy-1H-1,3-benzodiazol-2-yl)-5-(3-fluoro-5-methylphenyl)pyridin-2-amine;
3-17: 4-[(4αS,8αS)-octahydro-1H-pyrido[3,4-b][1,4]oxazin-6-yl]-5-(3-chloro-5-fluorophenyl)-3-(6-fluoro-4-methoxy-1H-1,3-benzodiazol-2-yl)pyridin-2-amine;
3-18: 2-{4-[(4αS,8αS)-octahydro-1H-pyrido[3,4-b][1,4]oxazin-6-yl]-2-amino-5-(3,5-difluorophenyl)pyridin-3-yl}-4-methoxy-1H-1,3-benzodiazole-6-carbonitrile;
3-19: 2-{4-[(4αS,8αS)-octahydro-1H-pyrido[3,4-b][1,4]oxazin-6-yl]-2-amino-5-(3,5-difluorophenyl)pyridin-3-yl}-4-fluoro-1H-1,3-benzodiazole-6-carbonitrile.

In some embodiments, provided herein is a pharmaceutically acceptable salt of a compound that is described in Table 3.

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCHNHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound of Formula (I), Formula (II), or Formula (III) with an acid. In some embodiments, the compound of Formula (I), Formula (II), or Formula (III) (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound of Formula (I), Formula (II), or Formula (III) is prepared as a chloride salt, sulfate salt, bromide salt, mesylate salt, maleate salt, citrate salt or phosphate salt.

In some embodiments, pharmaceutically acceptable salts are obtained by reacting a compound of Formula (I), Formula (II), or Formula (III) with a base. In some embodiments, the compound of Formula (I), Formula (II), or Formula (III) is acidic and is reacted with a base. In such situations, an acidic proton of the compound of Formula (I), Formula (II), or Formula (III) is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), or pharmaceutically acceptable salts of compounds having the structure of Formula (I), Formula (II), or Formula (III), as well as active metabolites of these compounds having the same type of activity.

In some embodiments, sites on the organic radicals (e.g. alkyl groups, aromatic rings) of compounds of Formula (I), Formula (II), or Formula (III) are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine chlorine, iodine, phosphorus, such as, for example, $^2H$, $^3H$, $^{13}C$, $^{14}C$, $^{15}N$, $^{18}O$, $^{17}O$, $^{35}S$, $^{18}F$, $^{36}Cl$, $^{123}I$, $^{124}I$, $^{125}I$, $^{131}I$, $^{32}P$ and $^{33}P$. In one aspect, isotopically-labeled compounds described herein, for example those into which radioactive isotopes such as $^3H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds of Formula (I), Formula (II), or Formula (III) possess one or more stereocenters and each stereocenter exists independently in either the R or S configuration. In some embodiments, the compound of Formula (I), Formula (II), or Formula (III) exists in the R configuration. In some embodiments, the compound of Formula (I), Formula (II), or Formula (III) exists in the S configuration. The compounds presented herein include all diastereomeric, individual enantiomers, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns or the separation of diastereomers by either non-chiral or chiral chromatographic columns or crystallization and recrystallization in a proper solvent or a mixture of solvents. In certain embodiments, compounds of Formula (I), Formula (II), or Formula (III) are prepared as their individual stereoisomers by reacting a racemic mixture of the compound with an optically active resolving agent to form a pair of diastereoisomeric compounds/salts, separating the diastereomers and recovering the optically pure individual enantiomers. In some embodiments, resolution of individual enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, N-alkyloxyacyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound of Formula (I), Formula (II), or Formula (III) as set forth herein are included within the scope of the claims. In some cases, some of the herein-described compounds is a prodrug for another derivative or active compound.

In some embodiments, any one of the hydroxyl group(s), amino group(s) and/or carboxylic acid group(s) are functionalized in a suitable manner to provide a prodrug moiety. In some embodiments, the prodrug moiety is as described above.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulfhydryl groups. Metabolites of the compounds disclosed herein are optionally identified either by administration of compounds to a host and analysis of tissue samples from the host, or by incubation of compounds with hepatic cells in vitro and analysis of the resulting compounds.

Synthesis of Compounds

Compounds of Formula (I), Formula (II), or Formula (III) described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, 6th Edition, John Wiley and Sons, Inc. Alternative reaction conditions for the synthetic transformations described herein may be employed such as variation of solvent, reaction temperature, reaction time, as well as different chemical reagents and other reaction conditions.

In some other embodiments, compounds described herein are prepared as described in Scheme A.

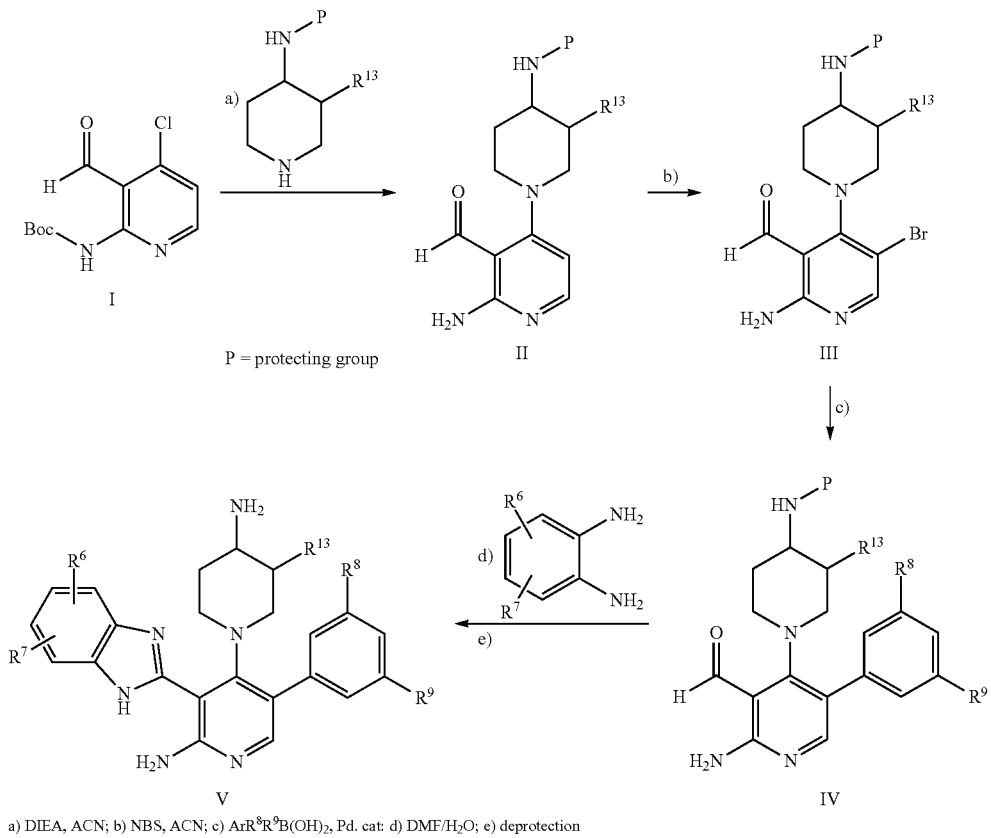

Nucleophilic substitution of I by 4-Boc aminopiperidine afforded intermediate II. Compound II was treated with NBS to yield intermediate III which was subsequently converted to intermediate IV by an organometallic coupling reaction such as Suzuki-Miyaura reaction with $ArR^8R^9B(OH)_2$. Benzimidazole formation between IV and corresponding 1,2-diaminobenzenes was achieved by heating in wet DMF or NMP or DMSO or other solvent with or without $Na_2S_2O_5$ under atmospheric oxygen. Subsequent removal of a protecting group using appropriate deprotection methods yielded the compound V. In some other embodiments, compounds described herein are prepared as described in Scheme B.

Scheme B

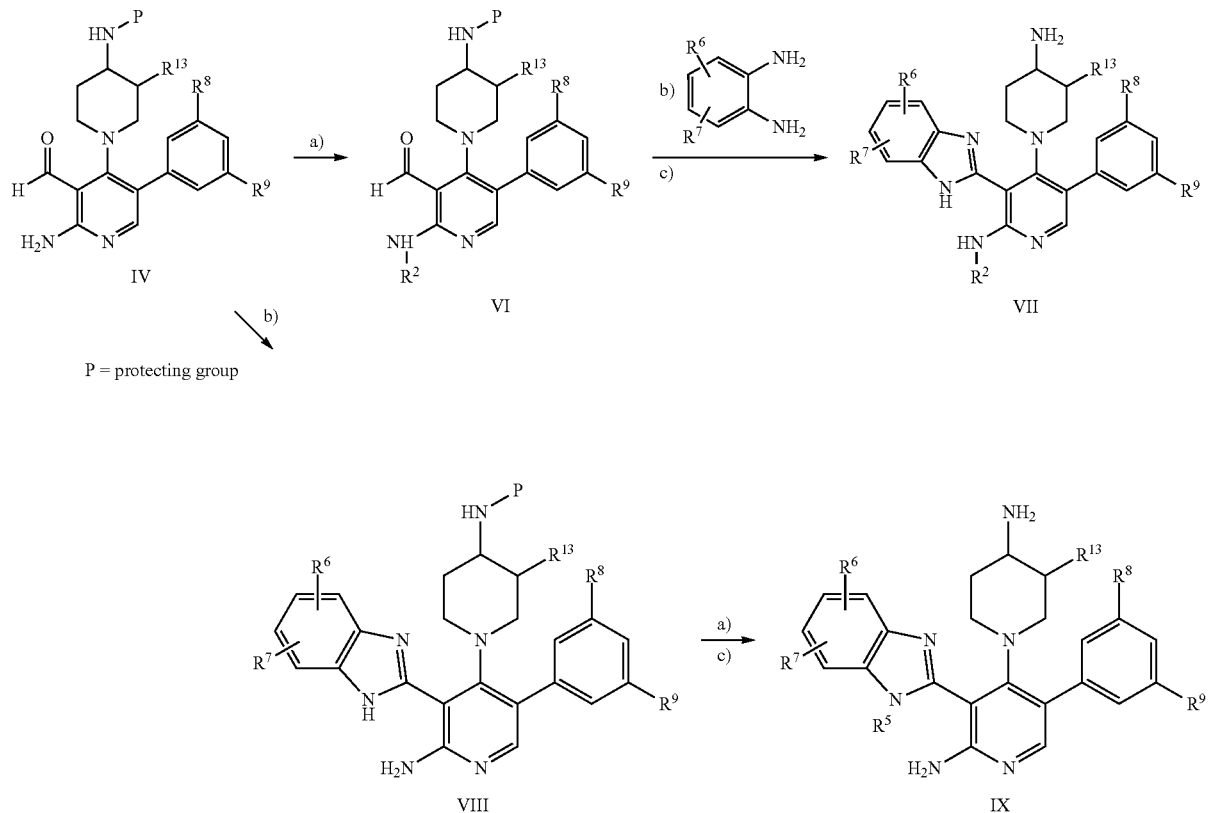

a) Alkyl halide, Base, b) DMF/H₂O, c) deprotection

The amino pyridine IV was alkylated to VI using the corresponding alkyl halide (R²—X) and a base. Benzimidazole formation and deprotection by a similar manner described in Scheme A gave compound VII. N-alkylation of VIII with an alkyl halide (R⁵—X) can be regioselectively achieved and deprotection of the amino protection group also produced compound IX.

In some other embodiments, compounds described herein are prepared as described in Scheme C.

Scheme C

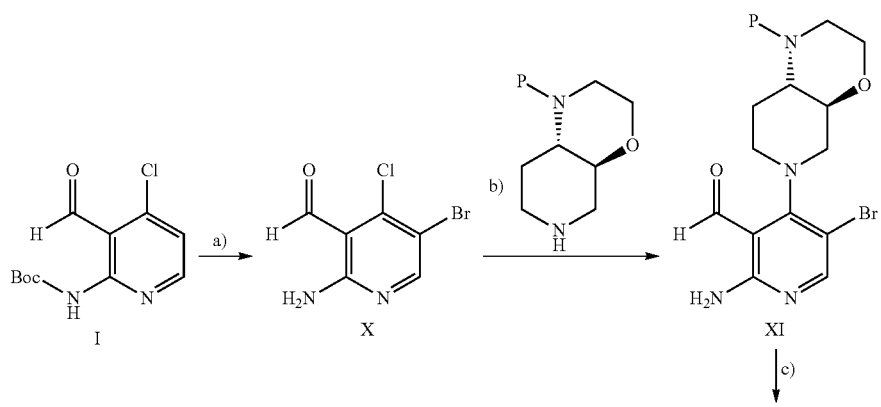

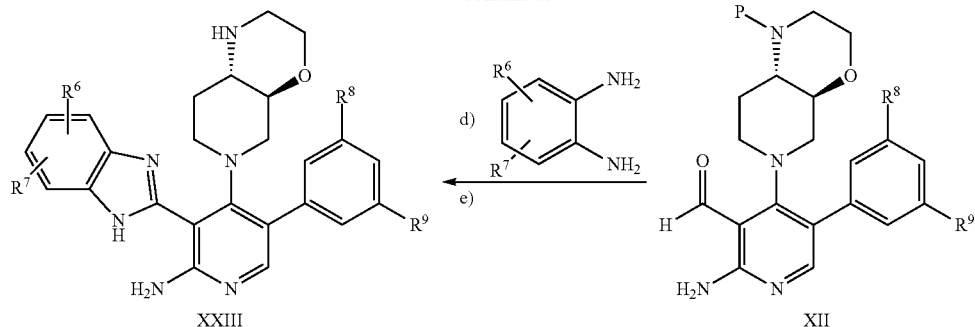
a) NBS, DCE; b) DIEA, ACN; c) ArR⁸R⁹B(OH)₂, Pd. cat; d) DMF/H₂O; e) deprotection
Regioselective bromination of I with NBS afforded intermediate X. The conversion of X to XXIII was completed by the similar manner described in Scheme A.
In some other embodiments, compounds described herein are prepared as described in Scheme D.
Scheme D
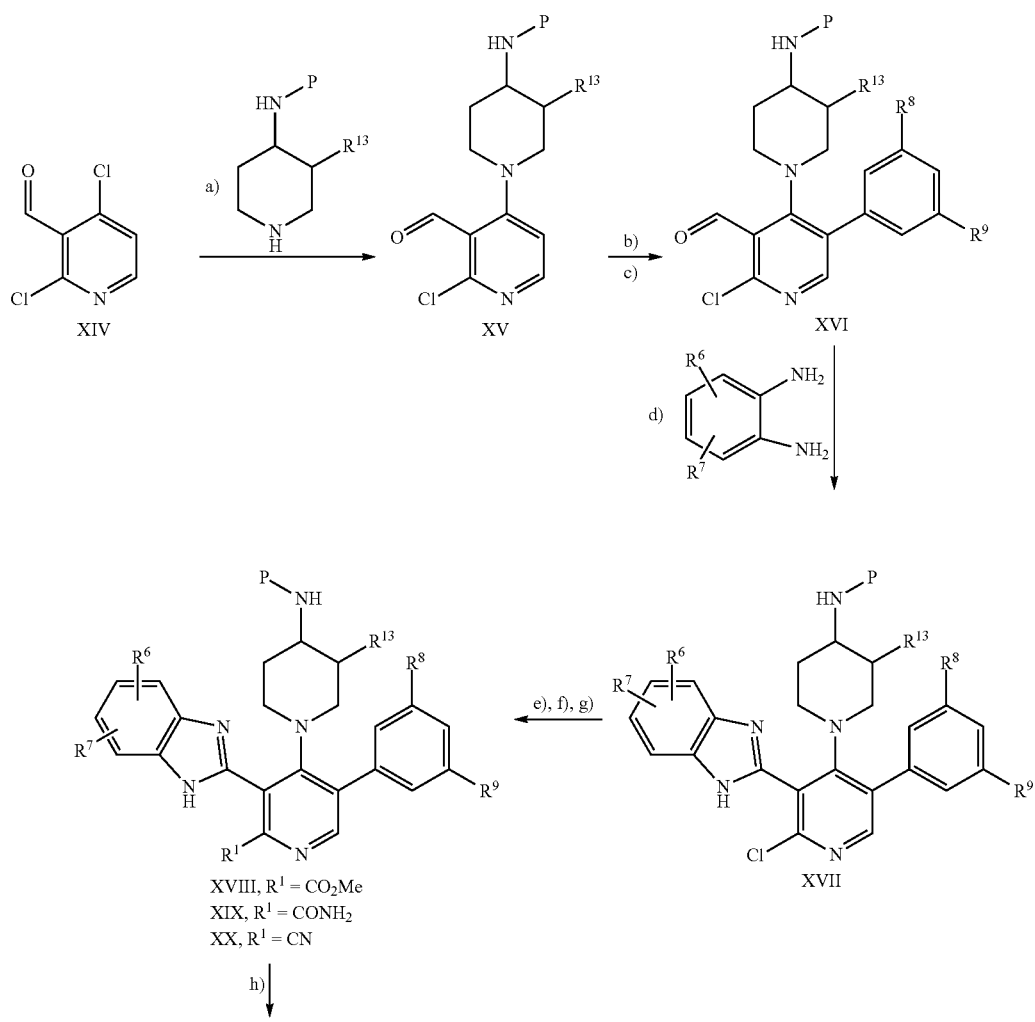

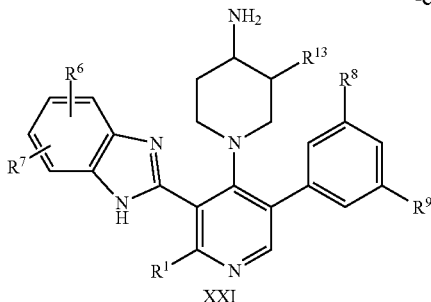

XXI a) DIEA, DMSO;
b) NBS, DMF;
c) Ar(R$^8$R$^9$)B(OH)$_2$, Pd. cat;
d) Na$_2$S$_2$O$_5$, DMSO;
e) Pd(0), CO, MeOH;
f) NH$_3$/MeOH;
g) TFAA, TEA, DCM;
h) TFA, DCM Compound XIV reacted with an amine to form XV. Bromination of XV and followed by Suzuki coupling reaction resulted in XVI, which was heated with a aryl-diamine to produce XVII. A carbon monoxide insertion in the presence of an alcohol led to formation of XVIII, which can be converted to XIX by ammonia, further dehydralation to afford XX. Deprotection of VIII or XIX or XX yielded XXI.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ ... $C_1$-$C_x$. By way of example only, a group designated as "$C_1$-$C_6$" indicates that there are one to six carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl radical. Any of the above mentioned monovalent alkyl groups may be an alkylene by abstraction of a second hydrogen atom from the alkyl. In some embodiments, an alkelene is a $C_1$-$C_6$alkylene. In other embodiments, an alkylene is a $C_1$-$C_4$alkylene. Typical alkylene groups include, but are not limited to, —CH$_2$—, —CH$_2$CH$_2$—, —CH$_2$CH$_2$CH$_2$—, —CH$_2$CH$_2$CH$_2$CH$_2$—, and the like. In some embodiments, an alkylene is —CH$_2$—.

An "alkoxy" group refers to a (alkyl)O-group, where alkyl is as defined herein.

The term "alkylamine" refers to the —N(alkyl)$_x$H$_y$ group, where x is 0 and y is 2, or where x is 1 and y is 1, or where x is 2 and y is 0.

An "hydroxyalkyl" refers to an alkyl in which one hydrogen atom is replaced by a hydroxyl. In some embodiments, a hydroxyalkyl is a $C_1$-$C_4$hydroxyalkyl. Typical hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, and the like.

An "aminoalkyl" refers to an alkyl in which one hydrogen atom is replaced by an amino. In some embodiments, aminoalkyl is a $C_1$-$C_4$aminoalkyl. Typical aminoalkyl groups include, but are not limited to, —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, and the like.

The term "alkenyl" refers to a type of alkyl group in which at least one carbon-carbon double bond is present. In one embodiment, an alkenyl group has the formula —C(R)=CR$_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH=CH$_2$, —C(CH$_3$)=CH$_2$, —CH=CHCH$_3$, —C(CH$_3$)=CHCH$_3$, and —CH$_2$CH=CH$_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡C—CH$_3$—C≡C—CH$_2$CH$_3$, —CH$_2$C≡CH.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "aromatic" refers to a planar ring having a delocalized π-electron system containing 4n+2π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycles include aryls and cycloalkyls.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a phenyl, naphthyl, indanyl, indenyl, or tetrahyodronaphthyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1] pentyl. In some embodiments, a cycloalkyl is a $C_3$-$C_6$cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoralkyl is a $C_1$-$C_6$fluoroalkyl.

The term "heterocycle" or "heterocyclic" refers to heteroaromatic rings (also known as heteroaryls) and heterocycloalkyl rings containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo [4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d] imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicycicic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heterocycloalkyl also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, —$NH_2$, —NH(alkyl), —N(alkyl)$_2$, —OH, —$CO_2$H, —$CO_2$alkyl, —C(=O)$NH_2$, —C(=O)NH(alkyl), —C(=O)N(alkyl)$_2$, —S(=O)$_2NH_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —$NH_2$, —NH($CH_3$), —N($CH_3$)$_2$, —OH, —$CO_2$H, —$CO_2$($C_1$-$C_4$alkyl), —C(=O)$NH_2$, —C(=O)NH($C_1$-$C_4$alkyl), —C(=O)N($C_1$-$C_4$alkyl)$_2$, —S(=O)$_2NH_2$, —S(=O)$_2$NH($C_1$-$C_4$alkyl), —S(=O)$_2$N($C_1$-$C_4$alkyl)$_2$, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, —S(=O)$C_1$-$C_4$alkyl, and —S(=O)$_2C_1$-$C_4$alkyl. In some embodiments, optional substituents are independently selected from halogen, —CN, —$NH_2$, —OH, —NH($CH_3$), —N($CH_3$)$_2$, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic) includes oxo (=O).

In some embodiments, each substituted alkyl, substituted fluoroalkyl, substituted heteroalkyl, substituted carbocycle, and substituted heterocycle is substituted with one or more $R^S$ groups independently selected from the group consisting of halogen, $C_1$-$C_6$alkyl, monocyclic carbocycle, monocyclic heterocycle, —CN, —$OR^{20}$, —$CO_2R^{20}$, —C(=O)N($R^{20}$)$_2$, —N($R^{20}$)$_2$, —$NR^{20}$C(=O)$R^{21}$, —$SR^{20}$, —S(O)$R^{21}$, —$SO_2R^{21}$, or —$SO_2$N($R^{20}$)$_2$; each $R^{20}$ is independently selected from hydrogen, $C_1$-$C_6$alkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl; or two $R^{20}$ groups are taken together with the N atom to which they are attached to form a N-containing heterocycle; each $R^{20}$ is independently selected from $C_1$-$C_6$alkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), Formula (II), or Formula (III), or a pharmaceutically acceptable salt thereof, and a co-agent, are both administered to a patient simultaneously in the form of a single entity or dosage. The term "non-fixed combination" means that the active ingredients, e.g. a compound of Formula (I), Formula (II), or Formula (III), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds of Formula (I), Formula (II), or Formula (III), or a pharmaceutically acceptable salt thereof, are used in the preparation of medicaments for the treatment of diseases or conditions in a mammal that would benefit from modulation of somatostatin activity. Methods for treating any of the diseases or conditions described herein in a mammal in need of such treatment, involves administration of pharmaceutical compositions that include at least one compound of Formula (I), Formula (II), or Formula (III) or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formula (I), Formula (II), or Formula (III), or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-2000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound of Formula (I), Formula (II), or Formula (III), or a pharmaceutically acceptable salt thereof, described herein are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound of Formula (I), Formula (II), or Formula (III), or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Combination Treatments

In certain instances, it is appropriate to administer at least one compound of Formula (I), Formula (II), or Formula (III), or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound of Formula (I), Formula (II), or Formula (III), or a pharmaceutically acceptable salt thereof, is co-administered with a second therapeutic agent, wherein the compound of Formula (I), Formula (II), or Formula (III), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds of Formula (I), Formula (II), or Formula (III), or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject.

EXAMPLES

As used above, and throughout the description of the invention, the following abbreviations, unless otherwise indicated, shall be understood to have the following meanings:

Abbreviations:
AcOH: acetic acid;
ACN or MeCN or $CH_3CN$: acetonitrile;
DCM: dichloromethane
DMF: dimethylformamide;
DMSO: dimethyl sulfoxide;
LC-MS: liquid chromatography-mass spectrometry;
MS: mass spectrometry;
NBS: N-bromosuccinimide;
NMP: N-Methyl-2-pyrrolidone;
NMR: nuclear magnetic resonance;
Prep-HPLC: preparative high performance liquid chromatography;
RP-HPLC: reverse phase high performance liquid chromatography;
SST: somatostatin;
SSTR: somatostatin receptor;
TEA: triethylamine;
TFA: trifluoroacetic acid;
TFAA: trifluoroacetic anhydride;
° C.: degree Celsius;
equiv: equivalent(s);
g: gram(s);
h or hr: hour;
hrs: hours;
mg: milligram(s);
MHz: megahertz;
min: minute;
mL or ml: milliliter(s);
mm: millimetre(s);
mmol: millimole(s);
μm or um: micrometre(s);
nm: nanometre;
rt: room temperature;
$CHCl_3$: chloroform;
CO: carbon monooxide;
$H_2O$: water;
$HBF_4$: tetrafluoroboric acid;
HCl: hydrochloric acid or hydrochloride;
$K_2CO_3$: potassium carbonate;
KOH: potassium hydroxide;
$K_3PO_4$: tripotassium phosphate;
MeOH: methanol;
$Me_2NH$: dimethylamine
$N_2$: nitrogen gas;
$NH_3$: ammonia
$Na_2SO_4$: sodium sulfate;
$Na_2S_2O_5$: sodium metabisulfite;
$P(t-Bu)_3$: tri-tert-buytlphosphine;
$Pd_2(dba)_3$: tris(dibenzylideneacetone)dipalladium(0);
$Pd(PPh_3)_2Cl_2$: bis(triphenylphosphine)palladium(II) dichloride;
$Pd(dppf)Cl_2$: [1,1'-bis(diphenylphosphino)ferrocene]palladium(II) dichloride;
Xantphos-4,5-bis(diphenylphosphino)-9,9-dimethylxanthene;
$Zn(CN)_2$: zinc cyanide.

The following examples are provided for illustrative purposes only and not to limit the scope of the claims provided herein.

Example 1: 2-[2-amino-4-(4-aminopiperidin-1-yl)-5-(3-fluoro-5-methylphenyl)pyridin-3-yl]-4-methoxy-1H-1,3-benzodiazole-6-carbonitrile (1-1)

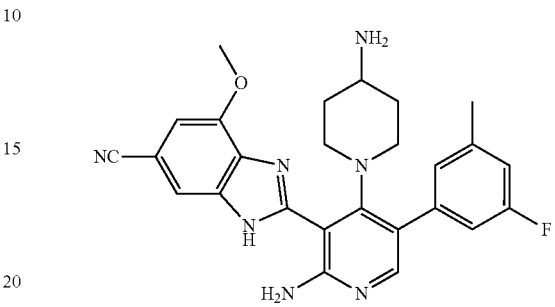

Step 1-1, preparation of 5-bromo-1-fluoro-3-methoxy-2-nitrobenzene: a mixture of 5-bromo-1,3-difluoro-2-nitrobenzene (10.0 g, 42.0 mmol, 1.0 equiv), KOH (3.1 g, 55.3 mmol, 1.3 equiv) in methanol (100 ml) was stirred at 40° C. for 3 hrs, then diluted with water (200 ml). The mixture was extracted with ethyl acetate (3×200 ml). The combined organic solution was washed with brine, dried and concentrated to yield the title compound (11.0 g) as a crude product. $^1$HNMR (300 MHz, DMSO-$d_6$): δ, 7.59 (d, 1H), 7.56 (s, 1H), 3.98 (s, 3H).

Step 1-2, preparation of 5-bromo-3-methoxy-2-nitroaniline: a mixture of 5-bromo-1-fluoro-3-methoxy-2-nitrobenzene (11 g, 20.0 mmol), ammonium hydroxide (30%, 100 ml) in NMP (100 ml) was heated with stirring at 50° C. for 2 days, then cooled to rt, diluted with water (300 ml). The mixture was then extracted with ethyl acetate (3×300 ml). The combined organic solution was then washed with brine, dried and concentrated after the solid was filtered out. The residue was concentrated to yield the title compound (10 g) as a yellow solid. MS [M+H]$^+$=247.1, 249.1.

Step 1-3, preparation of 5-bromo-3-methoxybenzene-1,2-diamine: a mixture of 5-bromo-3-methoxy-2-nitroaniline (10 g, 40.5 mmol, 1.0 equiv), $NH_4Cl$ (10.8 g, 201.9 mmol, 5.0 equiv), ethanol (100 ml), water (10 ml) and Fe power (11.4 g, 5.0 equiv) was stirred at 70° C. for 3 hrs. After cooling to rt, the mixture was diluted with ethyl acetate (200 ml) and the solid was then filtered out. The mixture was then further diluted with water (200 ml). Organic layer was separated and aqueous layer was further extracted with ethyl acetate (3×200 ml). The combined organic solution was washed with brine, dried and concentrated. The residue was purified by silica gel column chromatography, eluted with ethyl acetate/petroleum ether to afford the title compound (6.5 g) as an off-white solid. MS [M+H]$^+$=217.1, 219.1.

Step 1-4, preparation of tert-butyl N-[1-(2-amino-5-bromo-3-formylpyridin-4-yl)piperidin-4-yl]carbamate: a mixture of 2-amino-5-bromo-4-chloropyridine-3-carbaldehyde (25.0 g, 106.2 mmol, 1.0 equiv), tert-butyl N-(piperidin-4-yl)carbamate (21.2 g, 105.9 mmol, 1.0 equiv), TEA (32.1 g, 317.2 mmol, 3.0 equiv), N,N-dimethylformamide (120 mL) was stirred for 2 hrs at 80° C. The reaction was then quenched by the addition of 500 mL of water. The resulting solution was extracted with 3×500 mL of dichloromethane and the organic layers combined. The resulting mixture was washed with 5×200 mL of water. The mixture was dried over anhydrous sodium sulfate. The solids were filtered out and the liquid concentrated under vacuum. The residue was purified via a silica gel column eluted with dichloromethane/ethyl acetate (5:1) to give the title compound as a yellow solid (15 g). MS [M+H]=399.1, 401.1.

Step 1-5, preparation of tert-butyl N-{1-[2-amino-5-(3-fluoro-5-methylphenyl)-3-formylpyridin-4-yl]piperidin-4-yl}carbamate: into a 250-mL round-bottom flask purged and maintained with an inert atmosphere of nitrogen, was placed tert-butyl N-[1-(2-amino-5-bromo-3-formylpyridin-4-yl)piperidin-4-yl]carbamate (5.0 g, 12.5 mmol, 1.0 equiv), (3-fluoro-5-methylphenyl)boronic acid (2.9 g, 18.8 mmol, 1.5 equiv), $Pd_2(dba)_3HC\equiv Cl_3$ (1.3 g, 1.4 mmol, 0.10 equiv), $K_3PO_4$ (8.0 g, 37.7 mmol, 3.00 equiv), $P(t-Bu)_3$ $HBF_4$ (1.1 g, 0.3 equiv), toluene (50 mL), water (5 mL). The resulting solution was stirred for 2 hrs at 70° C., and then was concentrated under vacuum. The residue was chromatographied on a silica gel column eluted with ethyl acetate/petroleum ether (1:2) resulting in the title compound as a brown solid (5.0 g). MS [M+H]=429.2.

H-NMR (300 MHz, DMSO-$d_6$, ppm): δ 10.02 (s, 1H), 7.87 (s, 1H), 7.65 (br, 1H), 7.02 (d, J=9.6 Hz, 1H), 6.96-6.77 (m, 3H), 3.25 (s, 1H), 3.10 (d, J=12.5 Hz, 2H), 2.77 (t, J=11.6 Hz, 2H), 2.38 (s, 3H), 1.65-1.6 1(m, 2H), 1.44-1.37 (m, 11H).

Step 1-6, preparation of tert-butyl N-{1-[2-amino-3-(6-bromo-4-methoxy-1H-1,3-benzodiazol-2-yl)-5-(3-fluoro-5-methylphenyl)pyridin-4-yl]piperidin-4-yl}carbamate: A mixture of tert-butyl N-{1-[2-amino-5-(3-fluoro-5-methylphenyl)-3-formylpyridin-4-yl]piperidin-4-yl}carbamate (5 g, 11.7 mmol), 5-bromo-3-methoxybenzene-1,2-diamine (3.8 g, 17.5 mmol, 1.0 equiv), water (5 ml) in DMSO (50 ml) was heated at 120° C. for 16 hrs, cooled to rt, and then diluted with water (100 ml). The mixture was extract with ethyl acetate (3×200 ml). Combined organic solution was washed with brine, dried over anhydrous $Na_2SO_4$, filtered and then concentrated. The residue was purified by silica gel chromatography eluted with ethyl acetate/petroleum ether to afford the title compound as a brown solid (4.2 g). MS [M+H]$^+$=625.1,627.1.

Step 1-7, preparation of tert-butyl N-{1-[2-amino-3-(6-cyano-4-methoxy-1H-1,3-benzodiazol-2-yl)-5-(3-fluoro-5-methylphenyl)pyridin-4-yl]piperidin-4-yl}carbamate: to each of total four microwave tubes, purged and maintained under an inert atmosphere of N2, tert-butyl N-{1-[2-amino-3-(6-bromo-4-methoxy-1H-1,3-benzodiazol-2-yl)-5-(3-fluoro-5-methylphenyl)pyridin-4-yl]piperidin-4-yl}carbamate (1.1 g, 1.7 mmol), $Zn(CN)_2$ (600 mg, 5.1 mmol, 3.0 equiv), $Pd_2(dba)_3$ (53 mg, 0.06 mmol, 0.03 equiv), 4,5-bis(diphenylphosphino)-9,9-dimethylxanthene (105 mg, 0.18 mmol, 0.1 equiv) and DMF (10 ml) were added. Each tube was heated in microwave for 8 hrs at 120° C., then cooled to rt. The mixture from four tubes were combined and filtered to remove the solid and then diluted with water. Organics were extracted with ethyl acetate (3×100 ml). The combined organic solution was washed with brine, dried and concentrated. The residue was purified by RP-HPLC to afford the title compound (2.6 g) as off-white solid. MS [M+H]$^+$=572.6.

Step 1-8, preparation of 2-[2-amino-4-(4-aminopiperidin-1-yl)-5-(3-fluoro-5-methylphenyl)pyridin-3-yl]-4-methoxy-1H-1,3-benzodiazole-6-carbonitrile: a mixture of tert-butyl N-{1-[2-amino-3-(6-cyano-4-methoxy-1H-1,3-benzodiazol-2-yl)-5-(3-fluoro-5-methylphenyl)pyridin-4-yl]piperidin-4-yl}carbamate (80 mg, 0.14 mmol) and trifluoroacetic acid (1 mL) in dichloromethane (2 mL) was stirred for 2 hrs at rt and then concentrated, The crude product was purified by Prep-HPLC according to the following conditions (XBridge Prep C18): Column, 30×100 mm 5 μm; mobile phase, Water (0.05% TFA), ACN (26% up to 44% in 6 min); Detector, 220 nm. The fractions contained pure product were combined and lyophilized after addition of 1N HCl (0.1 ml), which resulted in the title compound as an off-white solid (HCl salt, 41.4 mg). MS [M+H]$^+$=472.3. $^1$HNMR (300 MHz, $CD_3OD$, ppm): δ, 7.83 (s, 1H), 7.70 (s, 1H), 7.25 (s, 1H), 7.17 (s, 1H), 7.10 (d, J=9.6 Hz, 2H), 4.11 (s, 3H), 3.26 (m, 2H), 3.02 (m, 1H), 2.55 (t, J=12.6 Hz, 2H), 2.48 (s, 3H), 1.61 (m, 2H), 1.23 (m, 2H).

The following compounds were prepared similarly to Example 1 with appropriate substituting reagents, solvents and substrates at different steps and they may require additional functional group modifications on benzimidazolyl side chain via well known chemistry with appropriate reagents, and different salt such as TFA or formic acid may be obtained.

| Compound no. | MS (M + H)$^+$ |
|---|---|
| 1-2 | 492.2 |

Example 2: 2-[4-(4-aminopiperidin-1-yl)-2-(dimethylamino)-5-(3-fluoro-5-methylphenyl)pyridin-3-yl]-4-methoxy-1H-1,3-benzodiazole-6-carbonitrile (Compound 1-3)

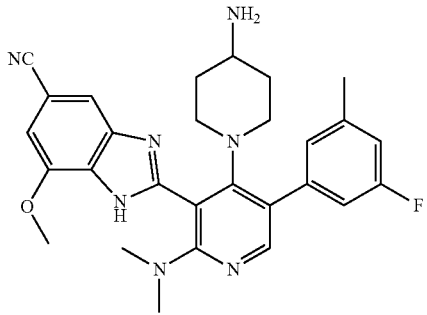 [SMILES: COc1cc(C#N)cc2nc(-c3c(N(C)C)ncc(-c4cc(C)cc(F)c4)c3N3CCC(N)CC3)[nH]c12]

Step 2-1, preparation of tert-butyl N-[1-(2-chloro-3-formylpyridin-4-yl)piperidin-4-yl]carbamate: into a 40-mL round-bottom flask, was placed 2,4-dichloropyridine-3-carbaldehyde (2.0 g, 11.36 mmol, 1.0 equiv), tert-butyl N-(piperidin-4-yl)carbamate (2.3 g, 11.48 mmol, 1.0 equiv), TEA (3.5 g, 34.59 mmol, 3.0 equiv), N,N-dimethylformamide (10 mL). The resulting solution was stirred for 1 h at 40° C. and then quenched with 50 mL water. The crude product was extracted out by 3×20 mL of ethyl acetate and ethyl acetate layer was washed with 4×20 mL of brine, then dried over anhydrous sodium sulfate. The solids were filtered out. The resulting mixture was concentrated and purified by silica gel column chromatography eluted with ethyl acetate/petroleum ether (1:3) to afford 3.2 g (83%) of the title compound as a yellow solid. MS (M+H)$^+$=340.1/342.1.

Step 2-2, preparation of tert-butyl N-{1-[2-(dimethylamino)-3-formylpyridin-4-yl]piperidin-4-yl}carbamate: into a 40-mL sealed tube, was placed tert-butyl N-[1-(2-chloro-3-formylpyridin-4-yl)piperidin-4-yl]carbamate (700 mg, 2.06 mmol, 1.0 equiv), tetrahydrofuran/$Me_2NH$(2 M) (10 mL). The resulting solution was sealed and stirred for 4 hrs at 70° C. The reaction mixture was cooled to rt and concentrated under vacuum. The remaining residue was applied onto a silica gel column with ethyl acetate/petroleum ether (1:1) resulting in 650 mg (91%) of the title compound as a light yellow solid. MS (M+H)+=349.2/351.2.

Step 2-3, preparation of tert-butyl N-{1-[5-bromo-2-(dimethylamino)-3-formylpyridin-4-yl]piperidin-4-yl}carbamate: to tert-butyl N-{1-[2-(dimethylamino)-3-formylpyridin-4-yl]piperidin-4-yl}carbamate (600 mg, 1.72 mmol, 1.0 equiv) in DCM (10 ml), NBS (306 mg, 1.72 mmol, 1.0 equiv) was added. The mixture was then stirred at 80° C. for 20 min. It was then cooled to rt, concentrated and purified by silica gel column chromatography, eluting with ethyl acetate/petroleum ether (2/3) to afford the title compound as a yellow solid (580 mg). MS (M+H)+=427.2/429.2.

Step 2-4, preparation of tert-butyl N-[1-[2-(dimethylamino)-5-(3-fluoro-5-methylphenyl}-3-formylpyridin-4-yl]piperidin-4-yl]carbamate: into a 100-mL round-bottom flask purged and maintained with an inert atmosphere of nitrogen, was placed tert-butyl N-[1-(5-bromo-2-(dimethylamino)-3-formylpyridin-4-yl]piperidin-4-yl]carbamate (550 mg, 1.29 mmol), (3-fluoro-5-methylphenyl)boronic acid (396 mg. 2.57 mmol, 2.0 equiv), Pd$_2$(dba)$_3$ (25 mg, 0.03 mmol. 0.02 equiv), P(t-Bu)$_3$ (50 mg), K$_3$PO$_4$ (817 mg, 3.85 mmol, 3.0 equiv), toluene (10 ml). water (1 mL). The resulting solution was stirred for 30 min at 70° C. The reaction mixture was cooled to rt, concentrated. The residue was chromatagraphied onto a silica gel column eluted with ethyl acetate/petroleum ether (1:1) to afford the title compound (560 mg) as a yellow solid. MS (M+H)+=457.3.

Step 2-5, preparation of tert-butyl N-{1-[3-(6-bromo-4-methoxy-1H-1,3-benzodiazol-2-yl)-2-(dimethylamino)-5-(3-fluoro-5-methylphenyl)pyridin-4-yl]piperidin-4-yl}carbamate: into a 10 ml sealed tube, was placed tert-butyl N-[1-[2-(dimethylamino)-5-(3-fluoro-5-methylphenyl}-3-formylpyridin-4-yl]piperidin-4-yl]carbamate (150 mg, 0.33 mol), 5-bromo-3-methoxybenzene-1,2-diamine (142 mg, 0.65 mmol, 2.0 equiv), NMP (2 ml), Na$_2$S$_2$O$_5$ (125 mg, 2.0 equiv). The mixture was sealed and heated with stirring at 120° C. for 8 hrs. After it was cooled to rt, water (50 ml) was added. The mixture was then extracted with ethyl acetate (3×50 ml). The combined organic layer was washed with water, brine and dried over anhydrous sodium sulfate. After filtration, the solution was concentrated and purified by silica gel chromatography eluted with ethyl acetate/petroleum ether (1/1) to afford the title compound (160 mg) as a brown solid. MS (M+H)+=653.2, 655.2.

Step 2-6, preparation of tert-butyl N-{1-[3-(6-cyano-4-methoxy-1H-1,3-benzodiazol-2-yl)-2-(dimethylamino)-5-(3-fluoro-5-methylphenyl)pyridin-4-yl]piperidin-4-yl}carbamate: into a 10-mL microwave tube purged and maintained with an inert atmosphere of nitrogen, was placed tert-butyl N-{1-[3-(6-bromo-4-methoxy-1H-1,3-benzodiazol-2-yl)-2-(dimethylamino)-5-(3-fluoro-5-methylphenyl)pyridin-4-yl]piperidin-4-yl}carbamate (150 mg, 0.23 mmol), Xantphos (30 mg, 0.05 mmol. 0.23 equiv), Pd$_2$(dba)$_3$ (15 mg), DMF (2 mL), Zn(CN)$_2$ (75 mg, 3.0 equiv). The reaction mixture was irradiated with microwave radiation for 2 hrs at 140° C. After cooled to rt, the mixture was diluted with water (50 ml). The resulting solution was extracted with ethyl acetate (3×50 ml). The organic layers were combined and washed with brine, then dried over anhydrous sodium sulfate. After the solids were filtered out, the solution was concentrated and the residue was chromatagrphied by a silica gel column eluted with ethyl acetate/petroleum ether (1/1) to afford the title compound as a brown solid (90 mg). MS (M+H)+=600.2.

Step 2-7, preparation of 2-[4-(4-aminopiperidin-1-yl)-2-(dimethylamino)-5-(3-fluoro-5-methylphenyl)pyridin-3-yl]-4-methoxy-1H-1,3-benzodiazole-6-carbonitrile: a mixture of tert-butyl N-{1-[3-(6-cyano-4-methoxy-1H-1,3-benzodiazol-2-yl)-2-(dimethylamino)-5-(3-fluoro-5-methylphenyl)pyridin-4-yl]piperidin-4-yl}carbamate (90 mg, 0.15 mmol), TFA (1 ml) in DCM (5 ml) was stirred at rt for 2 hrs. The mixture was concentrated and yielded the title compound as an off-white solid (84.1 mg). MS (M+H)+=500.3.

Example 3: 4-(4-aminopiperidin-1-yl)-3-(6-fluoro-4-methoxy-1H-1,3-benzodiazol-2-yl)-5-(3-fluoro-5-methylphenyl)pyridine-2-carbonitrile (Compound 2-2)

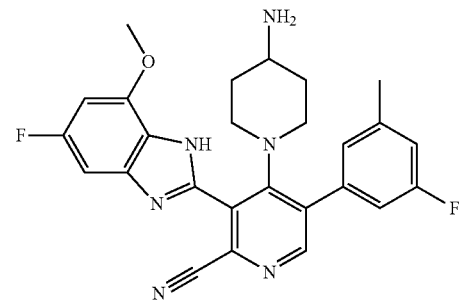 [SMILES: COc1cc(F)cc2nc(-c3c(C#N)ncc(-c4cc(C)cc(F)c4)c3N3CCC(N)CC3)[nH]c12]

Step 3-1, preparation of tert-butyl N-[1-(5-bromo-2-chloro-3-formylpyridin-4-yl)piperidin-4-yl]carbamate: a mixture of tert-butyl N-[1-(2-chloro-3-formylpyridin-4-yl)piperidin-4-yl]carbamate (500 mg, 1.47 mmol, Step 2-1) and NBS (290 mg, 1.63 mmol, 1.1 equiv) in DMF (10 ml) was stirred at rt for 16 hrs. The mixture was diluted with water (100 ml), and crude was extracted with ethyl acetate (3×100 ml). The organics were washed with brine, dried, and then concentrated. The crude was then purified by a silica gel column chromatography, elute with ethyl acetate/petroleum ether (2:3) to afford the title compound as a yellow solid (300 mg). MS [M+H]+=418.2/420.1.

Step 3-2, preparation of tert-butyl N-[1-[2-chloro-5-(3-fluoro-5-methylphenyl)-3-formylpyridin-4-yl]piperidin-4-yl]carbamate: Into a 50-mL round-bottom flask purged and maintained with an inert atmosphere of nitrogen, was placed tert-butyl N-[1-(5-bromo-2-chloro-3-formylpyridin-4-yl)piperidin-4-yl]carbamate (250 mg, 0.60 mmol), (3-fluoro-5-methylphenyl)boronic acid (92 mg, 0.60 mmol, 1.0 equiv), Pd(dppf)Cl$_2$ (50 mg, 0.07 mmol, 0.12 equiv), K$_2$CO$_3$ (165 mg, 1.2 mmol, 2.0 equiv), dioxane (5 mL), H$_2$O (0.5 mL). The resulting mixture was stirred for 2 hrs at 60° C. and then concentrated under vacuum. The residue was chromatographied on a silica gel column, eluted with ethyl acetate/petroleum ether to produce the title compound as a yellow solid (250 mg). MS [M+H]+=448.1.

Step 3-3, preparation of tert-butyl N-{1-[2-chloro-3-(6-fluoro-4-methoxy-1H-1,3-benzodiazol-2-yl)-5-(3-fluoro-5-methylphenyl)pyridin-4-yl]piperidin-4-yl}carbamate: using tert-butyl N-[1-[2-chloro-5-(3-fluoro-5-methylphenyl)-3-formylpyridin-4-yl]piperidin-4-yl]carbamate (230 mg, 0.51 mmol), 5-fluoro-3-methoxybenzene-1,2-diamine (160 mg, 1.02 mmol, 2.0 equiv), Na₂S₂O₅ (196 mg, 1.03 mmol, 2.0 equiv) in DMSO (5 mL), the title compound was obtained according to procedure described in Step 1-5 as a yellow solid (220 mg). MS [M+H]⁺=584.1.

Step 3-4, preparation of methyl 4-(4-{[(tert-butoxy)carbonyl]amino}piperidin-1-yl)-3-(6-fluoro-4-methoxy-1H-1,3-benzodiazol-2-yl)-5-(3-fluoro-5-methylphenyl)pyridine-2-carboxylate: into a pressure vessel (50 ml), purged and maintained with an inert atmosphere of CO (10 atm), was tert-butyl N-{1-[2-chloro-3-(6-fluoro-4-methoxy-1H-1,3-benzodiazol-2-yl)-5-(3-fluoro-5-methylphenyl)pyridin-4-yl]piperidin-4-yl}carbamate (180 mg, 0.31 mmol), Pd(dppf)Cl₂ (18 mg, 0.02 mmol), TEA (94 mg, 0.93 mmol), MeOH (15 mL). The resulting mixture was stirred for 8 hrs at 120° C., cooled to rt and concentrated. The residue was purified via a silica gel column, eluted with ethyl acetate/petroleum ether (5:4) to give the title compound as a light yellow solid (160 mg). MS [M+H]⁺=608.5.

Step 3-5, preparation of tert-butyl N-{1-[2-carbamoyl-3-(6-fluoro-4-methoxy-1H-1,3-benzodiazol-2-yl)-5-(3-fluoro-5-methylphenyl)pyridin-4-yl]piperidin-4-yl}carbamate: into a 40-mL sealed tube, was placed methyl 4-(4-{[(tert-butoxy)carbonyl]amino}piperidin-1-yl)-3-(6-fluoro-4-methoxy-1H-1,3-benzodiazol-2-yl)-5-(3-fluoro-5-methylphenyl)pyridine-2-carboxylate (150 mg, 0.25 mmol), MeOH/NH₃ (10 mL, 7 mol/L). The resulting solution was stirred for 5 hrs at 80° C., then concentrated resulting in the title compound as a brown solid (140 mg). MS [M+H]⁺=593.1.

Step 3-6, preparation of tert-butyl N-{1-[2-cyano-3-(6-fluoro-4-methoxy-1H-1,3-benzodiazol-2-yl)-5-(3-fluoro-5-methylphenyl)pyridin-4-yl]piperidin-4-yl}carbamate: into a 8-mL round-bottom flask, was placed tert-butyl N-{1-[2-carbamoyl-3-(6-fluoro-4-methoxy-1H-1,3-benzodiazol-2-yl)-5-(3-fluoro-5-methylphenyl]pyridin-4-yl}piperidin-4-yl carbamate (20 mg, 0.03 mmol), TEA (10 mg, 0.10 mmol, 3.3 equiv), DCM (1 mL), trifluoroacetic anhydride (14 mg, 0.07 mmol, 2.3 equiv). The resulting solution was stirred for 2 hrs at rt, and then concentrated. The crude was purified by Prep-HPLC to yield the title compound as off-white solid (10 mg). MS [M+H]⁺=575.3.

Step 3-7, preparation of 4-(4-aminopiperidin-1-yl)-3-(6-fluoro-4-methoxy-1H-1,3-benzodiazol-2-yl)-5-(3-fluoro-5-methylphenyl)pyridine-2-carbonitrile: into a 100-mL round-bottom flask, was placed yield tert-butyl N-{1-[2-cyano-3-(6-fluoro-4-methoxy-1H-1,3-benzodiazol-2-yl)-5-(3-fluoro-5-methylphenyl)pyridin-4-yl]piperidin-4-yl}carbamate (10 mg, 0.02 mmol), DCM (5 mL), TFA (1 mL). The resulting solution was stirred for 2 hrs at rt and then concentrated. The residue was diluted with water (5 mL) and CH₃CN (1 mL) and then lyophilized to yield the title compound as TFA salt (off-white solid, 7.8 mg). MS [M+H]⁺=475.2. ¹HNMR (300 MHz, CD₃OD): (δ, 8.47 (s, 1H), 7.19-7.08 (m, 3H), 7.02-6.99 (m, 2H), 6.85-6.73 (m, 2H), 4.05 (s, 3H), 3.3.21-3.12 (m, 2H), 2.94-2.92 (m, 1H), 2.59-2.42 (m, 5H), 1.64-1.54 (m, 2H), 1.25-1.19 (m, 2H).

Example 4: 4-(4-aminopiperidin-1-yl)-3-(6-fluoro-4-methoxy-1H-1,3-benzodiazol-2-yl)-5-(3-fluoro-5-methylphenyl)pyridine-2-carboxamide (Compound 2-3)

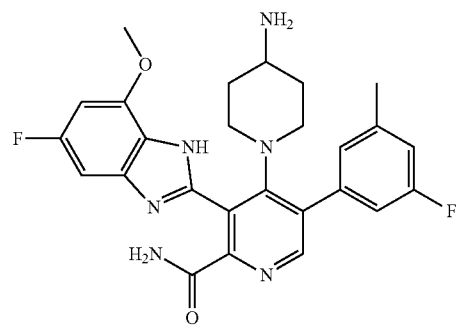 [SMILES: COc1cc(F)cc2nc(-c3c(C(N)=O)ncc(-c4cc(C)cc(F)c4)c3N3CCC(N)CC3)[nH]c12]

Step 4-1: Preparation of 4-(4-aminopiperidin-1-yl)-3-(6-fluoro-4-methoxy-1H-1,3-benzodiazol-2-yl)-5-(3-fluoro-5-methylphenyl)pyridine-2-carboxamide: a mixture of tert-butyl N-{1-[2-carbamoyl-3-(6-fluoro-4-methoxy-1H-1,3-benzodiazol-2-yl)-5-(3-fluoro-5-methylphenyl)pyridin-4-yl]piperidin-4-yl}carbamate (20 mg, 0.04 mmol, Step 3-5), DCM (5 mL) and TFA (1 mL) was stirred for 2 hrs at rt and concentrated. The crude product was purified by Prep-HPLC to afford the title compound as an off-white solid (TFA salt, 6.7 mg). MS [M+H]⁺=493.2. ¹HNMR (300 MHz, CD₃OD): (δ, 8.56 (s, 1H), 7.13-7.06 (m, 4H), 6.90 (d, J=11.7 Hz, 1H), 4.06 (s, 3H), 3.18-3.08 (m, 2H), 2.87-2.80 (m, 1H), 2.48-2.42 (m, 5H), 1.63-1.60 (m, 2H), 1.04-0.99 (m, 2H).

Example 5: methyl 4-(4-aminopiperidin-1-yl)-3-(6-fluoro-4-methoxy-1H-1,3-benzodiazol-2-yl)-5-(3-fluoro-5-methylphenyl)pyridine-2-carboxylate (Compound 2-1)

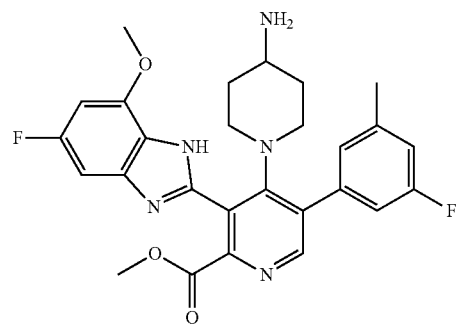 [SMILES: COC(=O)c1ncc(-c2cc(C)cc(F)c2)c(N2CCC(N)CC2)c1-c1nc2cc(F)cc(OC)c2[nH]1]

Step 5-1: Preparation of methyl 4-(4-aminopiperidin-1-yl)-3-(6-fluoro-4-methoxy-1H-1,3-benzodiazol-2-yl)-5-(3-fluoro-5-methylphenyl)pyridine-2-carboxylate: a mixture of methyl 4-(4-{[(tert-butoxy)carbonyl]amino}piperidin-1-yl)-3-(6-fluoro-4-methoxy-1H-1,3-benzodiazol-2-yl)-5-(3-fluoro-5-methylphenyl)pyridine-2-carboxylate from Step 3-4 (20 mg) in TFA/DCM (1 ml, 1:1) for 1 h and concentrated. The crude was purified by RP HPLC to afford the title compound (13.7 mg) as an off-white solid. MS [M+H]⁺=508.2.

Example 6: 2-{4-[(4αS,8αS)-octahydro-1H-pyrido[3,4-b][1,4]oxazin-6-yl]-2-amino-5-(3-fluoro-5-methylphenyl)pyridin-3-yl}-4-methoxy-1H-1,3-benzodiazole-6-carbonitrile (Compound 3-16)

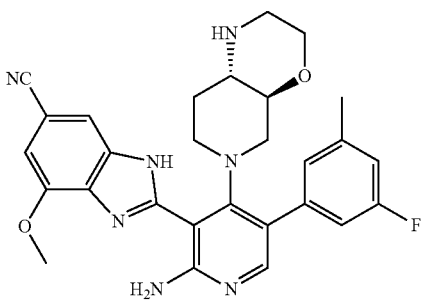 [SMILES: COc1cc(C#N)cc2[nH]c(-c3c(N)ncc(-c4cc(C)cc(F)c4)c3N3CC[C@@H]4NCCO[C@H]4C3)nc12]

Step 6-1, preparation of 2-amino-5-bromo-4-chloropyridine-3-carbaldehyde: into a 1 L round-bottom flask, was placed tert-butyl N-(4-chloro-3-formylpyridin-2-yl)carbamate (30.0 g, 117 mmol, 1.00 equiv), DCE (400 mL), NBS (42.0 g, 236 mmol, 2.0 equiv). The resulting solution was stirred for 16 hrs at 80° C. and then concentrated under vacuum. The residue was stirred with 200 mL of ethyl acetate to form a precipitate. The precipitated solids were then collected by filtration and dried in an oven under reduced pressure resulting in the title compound as a red solid (17.0 g). MS [M+H]$^+$=236.9.

Step 6-2, preparation of benzyl (4αS,8αS) 6-(2-amino-5-bromo-3-formyl-pyridin-4-yl)-octahydro-pyrido[3,4-b][1,4]oxazine-1-carboxylate: into a 100-mL round-bottom flask, was placed 2-amino-5-bromo-4-chloropyridine-3-carbaldehyde (2 g, 8.5 mmol, 1.5 equiv), benzyl (4αS,8αS)-octahydro-1H-pyrido[3,4-b]morpholine-1-carboxylate (1.57 g, 5.7 mmol, 1.0 equiv), TEA (1.72 g, 17.00 mmol, 3.0 equiv), N,N-dimethylformamide (20 mL). The resulting solution was stirred overnight at 80° C., then cooled to rt and diluted with water (50 ml). The mixture was extracted with ethyl acetate (3×100 ml) and the organic layers combined, washed with brine (3×100 ml) and then concentrated under vacuum which resulted in the title compound as a yellow solid (1.2 g). MS [M+H]$^+$=475.1.

Step 6-3, preparation of benzyl (4αS,8αS)-6-[2-amino-5-(3-fluoro-5-methylphenyl)-3-formylpyridin-4-yl]-octahydro-1H-pyrido[3,4-b]morpholine-1-carboxylate: into a 50-mL 3-necked round-bottom flask purged and maintained with nitrogen, was placed benzyl (4αS,8αS)-6-(2-amino-5-bromo-3-formylpyridin-4-yl)-octahydro-1H-pyrido[3,4-b]morpholine-1-carboxylate (300 mg, 0.63 mmol, 1.0 equiv), (3-fluoro-5-methylphenyl)boronic acid (192 mg, 1.25 mmol, 2.0 equiv), Pd$_2$(dba)$_3$·CHCl$_3$ (65 mg, 0.06 mmol, 0.10 equiv), P(t-Bu)$_3$·HBF$_4$ (37 mg, 0.13 mmol, 0.2 equiv), toluene (3 mL), water (0.3 mL), K$_3$PO$_4$ (402 mg, 3.0 equiv). The resulting mixture was stirred for 2 hrs at 70° C., and concentrated under vacuum after cooling to rt. The residue was chromatographied by a silica gel column eluted with ethyl acetate/petroleum ether to give the title compound as a yellow solid (200 mg). MS [M+H]$^+$=505.2.

Step 6-4, preparation of benzyl (4αS,8αS)-6-[2-amino-3-(6-bromo-4-methoxy-1H-1,3-benzodiazol-2-yl)-5-(3-fluoro-5-methylphenyl)pyridin-4-yl]-octahydro-1H-pyrido[3,4-b]morpholine-1-carboxylate: into a 50-mL round-bottom flask was placed benzyl (4αS,8αS)-6-[2-amino-5-(3-fluoro-5-methylphenyl)-3-formylpyridin-4-yl]-octahydro-1H-pyrido[3,4-b]morpholine-1-carboxylate (100 mg, 0.20 mmol, 1.00 equiv), 5-bromo-3-methoxybenzene-1,2-diamine (65 mg, 0.30 mmol, 1.50 equiv), Na$_2$S$_2$O$_5$ (75 mg, 0.39 mmol, 2.00 equiv), DMSO (2 mL). The resulting mixture was stirred for 16 hrs at 100° C., then cooled to rt and diluted with water (50 ml). The mixture was extracted with ethyl acetate (3×50 ml) and the organic layers combined and washed with brine (3×50 ml), and then concentrated under vacuum. The residue was chromatographied by a silica gel column eluted with ethyl acetate/petroleum ether to give the title compound (120 mg) as a yellow solid. MS [M+H]$^+$=701.2.

Step 6-5, preparation of benzyl (4αS,8αS)-6-[2-amino-3-(6-cyano-4-methoxy-1H-1,3-benzodiazol-2-yl)-5-(3-fluoro-5-methylphenyl)pyridin-4-yl]-octahydro-1H-pyrido[3,4-b]morpholine-1-carboxylate: into a 10-mL vial purged and maintained with nitrogen, was placed benzyl (4αS,8αS)-6-[2-amino-3-(6-bromo-4-methoxy-1H-1,3-benzodiazol-2-yl)-5-(3-fluoro-5-methylphenyl)pyridin-4-yl]-octahydro-1H-pyrido[3,4-b]morpholine-1-carboxylate (120 mg, 0.17 mmol, 1.00 equiv), N,N-dimethylformamide (2 mL), Pd$_2$(dba)$_3$ (18 mg, 0.02 mmol, 0.10 equiv), Xantphos (20 mg, 0.03 mmol, 0.20 equiv), zinc dicarbonitrile (40 mg, 0.34 mmol, 2.00 equiv). The mixture was irradiated with microwave radiation for 2 hrs at 120° C., then cooled to rt and diluted with water (5 ml). The crude was extracted with ethyl acetate (3×50 ml). The organic layers were combined, washed with brine (3×50 ml) and concentrated under vacuum. The residue was purified by a silica gel column chromatography eluted with ethyl acetate/petroleum ether to give the title compound (70 mg) as yellow oil. MS [M+H]$^+$=648.3.

Step 6-6, preparation of 2-[4-[(4αS,8αS)-octahydro-1H-pyrido[3,4-b]morpholin-6-yl]-2-amino-5-(3-fluoro-5-methylphenyl)pyridin-3-yl]-4-methoxy-1H-1,3-benzodiazole-6-carbonitrile: a mixture of benzyl (4αS,8αS)-6-[2-amino-3-(6-cyano-4-methoxy-1H-1,3-benzodiazol-2-yl)-5-(3-fluoro-5-methylphenyl)pyridin-4-yl]-octahydro-1H-pyrido[3,4-b]morpholine-1-carboxylate (70 mg, 0.11 mmol, 1.00 equiv), trifluoroacetic acid (2 mL) was stirred for 3 hrs at 60° C. The reaction mixture was cooled to rt. The resulting mixture was concentrated under vacuum. The residue was dissolved in DMF (4 mL) and further purified by Prep-HPLC to give the title compound as trifluoroacetic acid salt (49.6 mg, a white solid). MS [M+H]$^+$=514.4. $^1$HNMR (300 MHz, CD$_3$OD): δ, 7.83 (s, 1H), 7.72 (s, 1H), 7.25 (s, 1H), 7.15-7.07 (m, 3H), 4.10 (s, 3H), 3.96-3.87 (m, 1H), 3.62-3.48 (m, 1H), 3.41-3.35 (m, 1H), 3.26-3.05 (m, 4H), 2.93-2.85 (m, 1H), 2.65-2.55 (m, 1H), 2.48 (s, 3H), 2.33-2.26 (m, 1H), 1.59-1.56 (m, 1H), 1.31-1.19 (m, 1H).

The following compounds were prepared similarly to Example 6 with appropriate substituting reagents and substrates at different steps or without the step that converting bromo group to cyano group:

| Compound No. | MS (M + H)$^+$ |
|---|---|
| 3-1 | 495.2 |
| 3-2 | 499.2 |
| 3-3 | 481.2 |
| 3-6 | 513.2 |
| 3-7 | 515.2 |
| 3-8 | 511.3 |
| 3-9 | 493.2 |
| 3-10 | 507.3 |
| 3-11 | 500.3 |
| 3-12 | 514.3 |

-continued

| Compound No. | MS (M + H)+ |
|---|---|
| 3-13 | 541.3 |
| 3-14 | 507.3 |
| 3-15 | 521.3 |
| 3-17 | 527.1 |
| 3-18 | 518.2 |
| 3-19 | 506.2 |

Example A-1: Parenteral Pharmaceutical Composition

To prepare a parenteral pharmaceutical composition suitable for administration by injection (subcutaneous, intravenous), 1-100 mg of a water-soluble salt of a compound Formula (I), Formula (II), or Formula (III), or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection Example A-2: Oral Solution To prepare a pharmaceutical composition for oral delivery, a sufficient amount of a compound of Formula (I), Formula (II), or Formula (III), or a pharmaceutically acceptable salt thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound of Formula (I), Formula (II), or Formula (III), or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 10-500 mg of a compound of Formula (I), Formula (II), or Formula (III), or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound of Formula (I), Formula (II), or Formula (III), or a pharmaceutically acceptable salt thereof, is placed into Size 4 capsule, or size 1 capsule (hypromellose or hard gelatin) and the capsule is closed.

Example A-5: Topical Gel Composition

To prepare a pharmaceutical topical gel composition, a compound of Formula (I), Formula (II), or Formula (III), or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

Example B: SSTR Assays

Membrane Preparation

Crude membrane fractions are prepared from Chinese hamster ovary (CHO) cells stably expressing one of the five human or rodent somatostatin receptor subtypes. The cells are grown to 85-100% confluence on standard tissue culture dishes in DM-MEM growth media (Gibco) with following additives: 10% fetal bovine serum (Gibco), 100 U/mL penicillin (Gibco), 100 ug/mL streptomycin (Gibco), 10 mM HEPES (Gibco), 0.5 mg/mL G-418 (Gibco). To prepare membranes, cells are washed once with 1× Dulbecco's phosphate buffered saline (Gibco) containing 10 mM HEPES (Gibco) then once with sodium free binding buffer (50 mM Tris Base, 5 mM $MgCl_2$-$6H_2O$ and 1 mM EGTA adjusted to pH 7.8). The cells are then scraped into binding buffer containing a protease inhibitor cocktail (100 ug/mL pepstatin A (Sigma), 50 ug/mL leupeptin (Sigma), 25 ug/mL aprotinin (Sigma) and 10 mg/mL Bacitracin (USB Corporation)). The cells are centrifuged at 43,500×g, homogenized, and the resulting membranes are collected by centrifugation at 67,000×g. The membranes are then resuspended in binding buffer containing the protease inhibitor cocktail using a glass dounce homogenizer.

Functional Assay for SSTR2 Agonists

General overview: All five SSTR subtypes are Gi coupled G-protein coupled receptors (GPCRs) that lead to decreases in intracellular cyclic AMP (cAMP) when activated by an agonist. Therefore, measurement of intracellular cAMP levels can be used to assess whether compounds of the invention are agonists of SSTR subtypes (John Kelly, Troy Stevens, W. Joseph Thompson, and Roland Seifert, Current Protocols in Pharmacology, 2005, 2.2.1-2.2). One example of an intracellular cAMP assay is described below.

cAMP Assay Protocol

Four days prior to the assay, 5,000 Chinese hamster ovary cells (CHO-K1, ATCC #CCL-61) stably expressing the human somatostatin receptor subtype 2 are plated in each well of a 96-well tissue culture-treated plate in Ham's F12 growth media (ThermoFisher #10-080-CM) supplemented with 10% donor bovine serum (Gemini Bio-Products #100-506), 100 U/mL penicillin; 100 ug/mL streptomycin; 2 mM L-glutamine (Gemini Bio-Products #400-110) and 0.2 mg/mL hygromycin B (GoldBio #31282-04-9). The cells are cultured at 37° C., 5% $CO_2$ and 95% humidity. On the day of the assay, the media is aspirated and the cells are treated with 50 μL of 1.6 μM NKH477 (Sigma #N3290) plus various dilutions of compounds of the invention in assay buffer [1× Hank's Balanced Salt Solution (ThermoFisher #SH3058802), 0.5 mM HEPES pH 7.4, 0.1% bovine serum albumin, 0.2 mM 3-Isobutyl-1-methylxanthine (IBMX, VWR #200002-790)]. The cells are incubated for 20 minutes at 37° C. (the final concentration of the compounds of the invention are typically 0-10,000 nM). The cells are treated with 50 μL of lysis buffer (HRTF cAMP kit, Cisbio). The lysate is transferred to 384-well plates and cAMP detection and visualization antibodies are added and incubated for 1-24 hours at room temperature. The time-resolved fluorescent signal is read with a Tecan M1000Pro multiplate reader. The intracellular cAMP concentrations are calculated by regression to a standard curve and are plotted vs. the concentration of the compounds of the invention and the $EC_{50}$ of the compounds are calculated using standard methods. All data manipulations are in GraphPad Prism v6.

Illustrative biological activity of compounds is demonstrated in the following Table (Table A) by evaluating the inhibition of cAMP activities via human SST2 receptor (SSTR2):

TABLE A

| Cpd No. | $EC_{50}$ |
|---|---|
| 1-1 | A |
| 1-2 | B |
| 1-3 | C |
| 2-1 | B |
| 2-2 | B |
| 2-3 | B |
| 3-1 | A |
| 3-2 | B |
| 3-3 | B |
| 3-6 | B |
| 3-7 | A |
| 3-8 | A |
| 3-9 | B |
| 3-10 | B |
| 3-11 | B |
| 3-12 | C |
| 3-13 | B |
| 3-14 | A |
| 3-15 | A |
| 3-16 | A |
| 3-17 | A |
| 3-18 | B |
| 3-19 | B |

A = $EC_{50}$ < 0.1 nM; B = $EC_{50}$ between >0.1 nM and <1 nM; C = $EC_{50}$ ≥ 1 nM The following Table (Table B) demonstrates improved selectivity of exemplary compounds for inhibition of cAMP via hSSTR2 vs. hSSTR4.

TABLE B

[Structure of compound with $R^6$, OMe, $R^1$, NH$_2$, benzimidazole core, pyridine, and fluorophenyl group]

| Cpd No. | $R^1$ | $R^6$ | hSST4/hSST2 (ratio) |
|---|---|---|---|
|  | H | CN | d |
| 1-1 | NH$_2$ | CN | a |
|  | H | F | f |
| 2-1 | CO$_2$Me | F | d |
| 2-2 | CN | F | e |
| 2-3 | CONH$_2$ | F | b | a = above 50, b = between 15 and 50; c = between 2.5 and 15; d = between 1 and 2.5; e = between 1 and 0.5; f = below 0.5.

The following Table (Table C) further demonstrates improved selectivity for inhibition of cAMP via hSSTR2 vs. hSSTR4 of additional exemplary compounds.

TABLE C

[Structure of compound with $R^6$, $R^7$, $R^1$, $R^9$, benzimidazole, pyridine, fluorophenyl, and morpholine-piperidine bicyclic amine]

| Cpd No. | $R^1$ | $R^6$ | $R^7$ | $R^9$ | hSST4/hSST2 (ratio) |
|---|---|---|---|---|---|
|  | H | F | F | H | f |
| 3-3 | NH$_2$ | F | F | H | c |
|  | H | OMe | F | H | f |
| 3-9 | NH$_2$ | OMe | F | H | c |
| 3-10 | CH$_3$NH— | OMe | F | H | a |
|  | H | OMe | CN | H | d |
| 3-11 | NH$_2$ | OMe | CN | H | a |
| 3-12 | CH$_3$NH— | OMe | CN | H | a |
|  | H | OMe | F | Cl | d |
| 3-17 | NH2 | OMe | F | Cl | c |
| 3-13 | CH$_3$NH— | OMe | F | Cl | a |
|  | H | OMe | CN | F | d |
| 3-18 | NH$_2$ | OMe | CN | F | b |
|  | H | F | CN | F | d |
| 3-19 | NH$_2$ | F | CN | F | b | a = above 50, b = between 15 and 50; c = between 2.5 and 15; d = between 1 and 2.5; e = between 1 and 0.5; f = below 0.5

Example C: Liver Microsomal Stability Assay Protocol

The in vitro stabilities of compounds of interest were determined for various species using pooled male and female human, pooled male Sprague-Dawley rat, pooled male Cynomolgus monkey, and pooled male Beagle dog liver microsomes at microsomal protein concentrations of 0.5 mg/mL. Incubations were carried out in a potassium phosphate buffer (50 mM). The NADPH-generating system was composed of NADP+ (1 mM), magnesium chloride (3 mM), EDTA (1 mM), glucose-6-phosphate (5 mM) and glucose-6-phosphate dehydrogenase (1 Unit/mL) for all experiments. Compounds of interest in DMSO were added to achieve a final incubation concentration of 1 M (final DMSO content was 0.1% v/v and final acetonitrile content was 0.9%). The final incubation volume was 400 µL. Incubations were conducted at 37° C. for 0, 5, 10, 20, 40 and 60 minutes in a shaking water bath and terminated by removing 50 L of incubation mixture and adding to 100 µL of ice cold acetonitrile containing internal standard. Following precipitation by centrifugation at 3500 rpm and 4° C. for 30 minutes, compounds of interest and internal standard were analyzed in the resultant supernatant using a multiple reaction monitoring (MRM) LC-MS/MS method. MS conditions were optimized for each analyte. Depletion rates of compounds of interest were measured and half-life, scaled intrinsic clearance, and predicted scaled systemic clearance calculations were made using this data.

The following Table (Table D) illustrates human liver microsomal stability of exemplary compounds.

TABLE D

[Structure with R⁶, R⁷ on benzimidazole, morpholine-fused piperidine, pyridine with R¹, and phenyl with R⁹, F]

| Cpd No. | R¹ | R⁶ | R⁷ | R⁹ | HLM t1/2 (min) |
|---|---|---|---|---|---|
| | H | F | F | H | 41 |
| 3-3 | NH₂ | F | F | H | 231 |
| | H | OMe | CN | H | 115 |
| 3-11 | NH₂ | OMe | CN | H | >693 |
| | H | OMe | CN | F | 58 |
| 3-18 | NH₂ | OMe | CN | F | 99 |
| | H | F | CN | F | 144 |
| 3-19 | NH₂ | F | CN | F | 347 |

The examples and embodiments described herein are for illustrative purposes only and various modifications or changes suggested to persons skilled in the art are to be included within the spirit and purview of this application and scope of the appended claims.

What is claimed is:

1. A method of treating acromegaly, a neuroendocrine tumor, or a combination thereof in a mammal comprising administering a therapeutically effective amount of a compound that has one of the following structures:

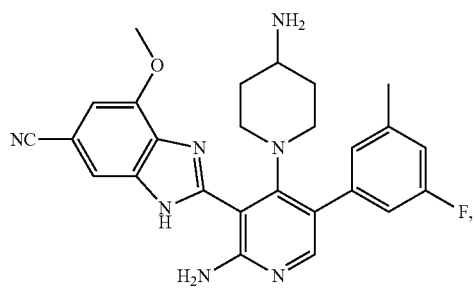 [SMILES: COc1cc(C#N)cc2[nH]c(-c3c(N)ncc(-c4cc(C)cc(F)c4)c3N3CCC(N)CC3)nc12]

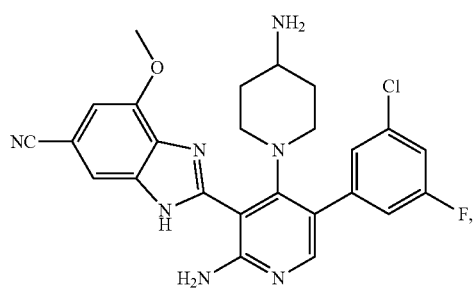 [SMILES: COc1cc(C#N)cc2[nH]c(-c3c(N)ncc(-c4cc(F)cc(Cl)c4)c3N3CCC(N)CC3)nc12]

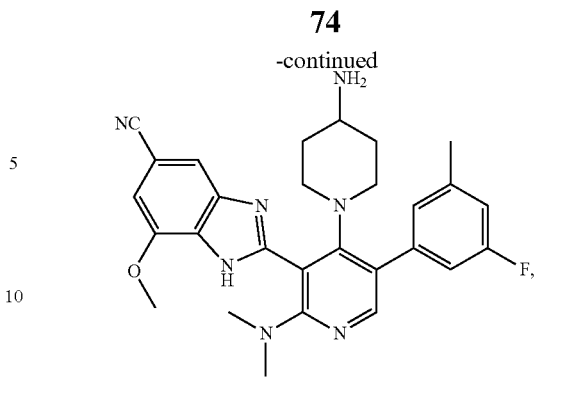

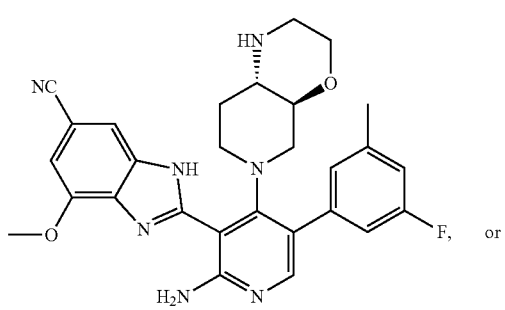

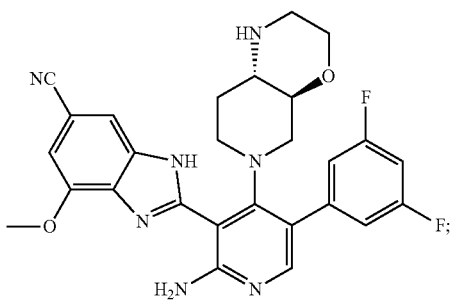

or a pharmaceutically acceptable salt, pharmaceutically acceptable solvate, diastereomeric mixture, or individual enantiomers thereof, to the mammal in need thereof.

2. The method of claim 1, wherein the compound has the following structure:

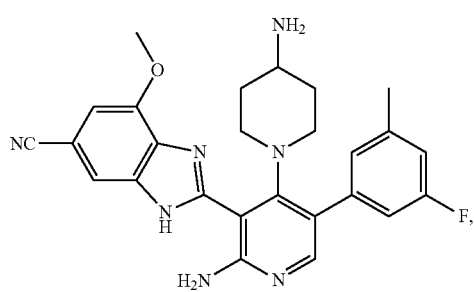

or a pharmaceutically acceptable salt, or solvate thereof.

3. The method of claim 1, wherein the compound has the following structure:

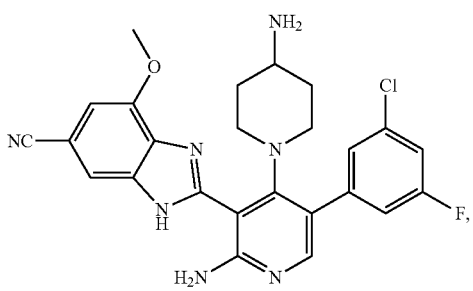

or a pharmaceutically acceptable salt, or solvate thereof.

4. The method of claim 1, wherein the compound has the following structure:

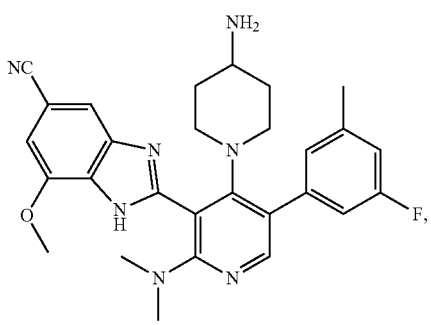 [SMILES: COc1cc(C#N)cc2nc(-c3c(N(C)C)ncc(-c4cc(C)cc(F)c4)c3N3CCC(N)CC3)[nH]c12]

or a pharmaceutically acceptable salt, or solvate thereof.

5. The method of claim 1, wherein the compound has the following structure:

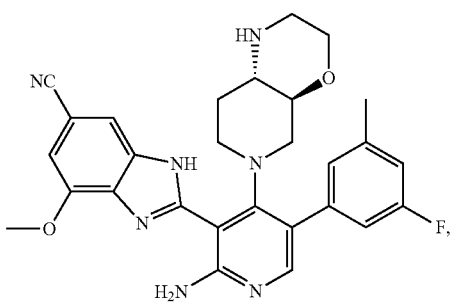 [SMILES: COc1cc(C#N)cc2[nH]c(-c3c(N)ncc(-c4cc(C)cc(F)c4)c3N3CC[C@@H]4NCCO[C@H]4C3)nc12]

or a pharmaceutically acceptable salt, or solvate thereof.

6. The method of claim 1, wherein the compound has the following structure:

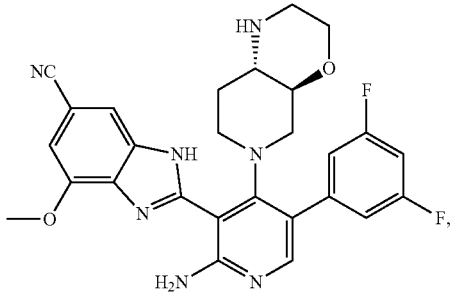 [SMILES: COc1cc(C#N)cc2[nH]c(-c3c(N)ncc(-c4cc(F)cc(F)c4)c3N3CC[C@@H]4NCCO[C@H]4C3)nc12]

or a pharmaceutically acceptable salt, or solvate thereof.

7. The method of claim 1 for treating acromegaly.

8. The method of claim 1 for treating neuroendocrine tumor.

9. A method of treating acromegaly, a neuroendocrine tumor, or a combination thereof, comprising administering a therapeutically effective amount of a compound having the following structure:

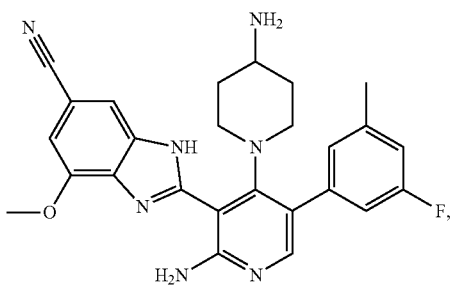 [SMILES: COc1cc(C#N)cc2[nH]c(-c3c(N)ncc(-c4cc(C)cc(F)c4)c3N3CCC(N)CC3)nc12]

or a pharmaceutically acceptable salt, or pharmaceutically acceptable solvate, thereof, to the mammal in need thereof.

10. The method of claim 9 for treating acromegaly.

11. The method of claim 9 for treating neuroendocrine tumor.

* * * * *

UNITED STATES PATENT AND TRADEMARK OFFICE
CERTIFICATE OF CORRECTION

| | | |
|---|---|---|
| PATENT NO. | : 11,186,590 B2 | Page 1 of 1 |
| APPLICATION NO. | : 16/877947 | |
| DATED | : November 30, 2021 | |
| INVENTOR(S) | : Sangdon Han et al. | |

It is certified that error appears in the above-identified patent and that said Letters Patent is hereby corrected as shown below:

In the Specification

Column 1, Lines 15-17:
"This invention was made with government support under NS092231 awarded by the National Institutes of Health. The government has certain rights in this invention." should read --This invention was made with government support under grant number NS092231 awarded by the National Institute of Health. The government has certain rights in the invention.--.

Signed and Sealed this
Thirty-first Day of December, 2024

Derrick Brent
*Acting Director of the United States Patent and Trademark Office*